(12) United States Patent
Chun et al.

(10) Patent No.: US 12,054,507 B2
(45) Date of Patent: Aug. 6, 2024

(54) ANTIVIRAL COMPOUNDS

(71) Applicant: Gilead Sciences, Inc., Foster City, CA (US)

(72) Inventors: Byoung-Kwon Chun, Pleasanton, CA (US); Edward Doerffler, Reno, NV (US); Dustin S. Siegel, Half Moon Bay, CA (US); Andrew C. Stevens, Edmonton (CA); Tiago Vieira, Edmonton (CA)

(73) Assignee: GILEAD SCIENCES, INC., Foster City, CA (US)

( * ) Notice: Subject to any disclaimer, the term of this patent is extended or adjusted under 35 U.S.C. 154(b) by 120 days.

(21) Appl. No.: 17/178,156

(22) Filed: Feb. 17, 2021

(65) Prior Publication Data
US 2021/0284669 A1    Sep. 16, 2021

Related U.S. Application Data

(60) Provisional application No. 62/977,969, filed on Feb. 18, 2020.

(51) Int. Cl.
| | | |
|---|---|---|
| *A01N 43/00* | (2006.01) | |
| *A01N 43/46* | (2006.01) | |
| *A61K 31/55* | (2006.01) | |
| *A61P 31/14* | (2006.01) | |
| *A61P 31/16* | (2006.01) | |
| *C07D 487/04* | (2006.01) | |
| *C07F 9/6561* | (2006.01) | |

(52) U.S. Cl.
CPC ............ *C07F 9/6561* (2013.01); *A61P 31/14* (2018.01); *A61P 31/16* (2018.01); *C07D 487/04* (2013.01)

(58) Field of Classification Search
CPC .......................... C07F 9/6561; C07D 487/04
See application file for complete search history.

(56) References Cited

U.S. PATENT DOCUMENTS

| | | | |
|---|---|---|---|
| 4,707,540 A | 11/1987 | Manser et al. | |
| 5,446,137 A | 8/1995 | Maag et al. | |
| 6,699,994 B1 | 3/2004 | Babu et al. | |
| 8,101,745 B2 | 1/2012 | Hostetler et al. | |
| 8,119,607 B2 | 2/2012 | Francom et al. | |
| 8,242,085 B2 | 8/2012 | Babu et al. | |
| 8,318,700 B2 | 11/2012 | Hostetler et al. | |
| 8,440,813 B2 | 5/2013 | Babu et al. | |
| 9,370,528 B2 | 6/2016 | Schentag et al. | |
| 9,388,208 B2 | 7/2016 | Clarke et al. | |
| 9,701,682 B2 | 7/2017 | Clarke et al. | |
| 9,724,360 B2 | 8/2017 | Chun et al. | |
| 9,777,035 B2 | 10/2017 | Girijavallabhan et al. | |
| 9,815,864 B2 | 11/2017 | Beigelman et al. | |
| 10,004,719 B1 | 6/2018 | Hsu et al. | |
| 10,059,716 B2 | 8/2018 | Clarke et al. | |
| 10,251,904 B2 | 4/2019 | Clarke et al. | |
| 10,377,761 B2 | 8/2019 | Clarke et al. | |
| 10,682,368 B2 | 6/2020 | Perron et al. | |
| 2002/0035082 A1 | 3/2002 | Grinstaff et al. | |
| 2002/0188137 A1 | 12/2002 | Dershem et al. | |
| 2003/0170891 A1 | 9/2003 | McSwiggen | |
| 2003/0175950 A1 | 9/2003 | McSwiggen | |
| 2003/0199516 A1 | 10/2003 | Moser et al. | |
| 2004/0009959 A1 | 1/2004 | Potter et al. | |
| 2004/0157838 A1 | 8/2004 | Griffith | |
| 2004/0157839 A1 | 8/2004 | Griffith | |
| 2004/0214837 A1 | 10/2004 | Griffith et al. | |
| 2004/0229839 A1 | 11/2004 | Babu et al. | |
| 2004/0229840 A1 | 11/2004 | Bhat et al. | |

(Continued)

FOREIGN PATENT DOCUMENTS

| | | |
|---|---|---|
| CN | 102000103 A | 4/2011 |
| CN | 102286047 A | 12/2011 |

(Continued)

OTHER PUBLICATIONS

CDC "Dengue" ( https://www.cdc.gov/dengue/healthcare-providers/treatment.html ) (Year: 2023).*
Wikipedia, "Pneumoviridae" (Year: 2023).*
Rueckert, (Chapter 21, Picornaviridae: The viruses and their replication. pp. 609-610. Fields Virology, vol. 1. Third Edition, Bernard Field, 1995). (Year: 2023).*
Wikipedia, "Flaviviridae". (Year: 2023).*
CDC "Human metapneumovirus" (https://www.cdc.gov/ncird/human-metapneumovhuman irus.html (Year: 2023).*
Krilov ("Respiratory Syncytial virus infection Medication" Medscape https://emedicine.medscape.com/article/971488-medication?form=fpf , 2023). (Year: 2023).*

(Continued)

*Primary Examiner* — Layla Soroush
(74) *Attorney, Agent, or Firm* — Mintz, Levin, Cohn, Ferris, Glovsky and Popeo, P.C.

(57) ABSTRACT

The present disclosure provides a compound of Formula I:

Formula I

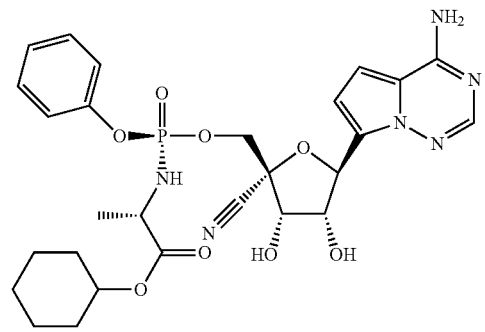

which is useful in treating a variety of diseases, such as diseases caused by respiratory syncytial virus (RSV), HRV, hMPV, ebola, Zika, West Nile, Dengue, HCV and/or HBV infections.

8 Claims, 3 Drawing Sheets

Specification includes a Sequence Listing.

(56) References Cited

U.S. PATENT DOCUMENTS

| | | |
|---|---|---|
| 2006/0121312 A1 | 6/2006 | Yamada et al. |
| 2006/0194144 A1 | 8/2006 | Sooriyakumaran et al. |
| 2006/0281922 A1 | 12/2006 | Gao et al. |
| 2007/0232635 A1 | 10/2007 | Chelliah et al. |
| 2009/0318380 A1 | 12/2009 | Sofia et al. |
| 2009/0323011 A1 | 12/2009 | He et al. |
| 2009/0323012 A1 | 12/2009 | He et al. |
| 2010/0035836 A1 | 2/2010 | Francom et al. |
| 2010/0040804 A1 | 2/2010 | Zhang |
| 2010/0096603 A1 | 4/2010 | Wang et al. |
| 2010/0184942 A1 | 7/2010 | Chen et al. |
| 2010/0186626 A1 | 7/2010 | Shin et al. |
| 2011/0212994 A1 | 9/2011 | Clem et al. |
| 2011/0216273 A1 | 9/2011 | He et al. |
| 2011/0287927 A1 | 11/2011 | Grasset et al. |
| 2011/0319459 A1 | 12/2011 | Gupta et al. |
| 2012/0009147 A1 | 1/2012 | Cho et al. |
| 2012/0020921 A1 | 1/2012 | Cho et al. |
| 2012/0035115 A1 | 2/2012 | Manoharan et al. |
| 2012/0070411 A1 | 3/2012 | Beigelman et al. |
| 2012/0070415 A1 | 3/2012 | Beigelman et al. |
| 2012/0071434 A1 | 3/2012 | Smith et al. |
| 2012/0214735 A1 | 8/2012 | Bhuniya et al. |
| 2012/0214762 A1 | 8/2012 | Staben et al. |
| 2012/0219568 A1 | 8/2012 | Liu et al. |
| 2012/0264649 A1 | 10/2012 | Bazan et al. |
| 2013/0303669 A1 | 11/2013 | Morimoto et al. |
| 2014/0038991 A1 | 2/2014 | Yu et al. |
| 2014/0200215 A1 | 7/2014 | Buckman et al. |
| 2014/0309413 A1 | 10/2014 | Rose et al. |
| 2015/0011497 A1 | 1/2015 | Beigelman et al. |
| 2015/0051167 A1 | 2/2015 | Wang et al. |
| 2015/0105341 A1 | 4/2015 | Beigelman et al. |
| 2015/0252265 A1 | 9/2015 | Archetti et al. |
| 2015/0274767 A1 | 10/2015 | Girijavallabhan et al. |
| 2015/0366887 A1 | 12/2015 | Blatt et al. |
| 2015/0366888 A1 | 12/2015 | Blatt et al. |
| 2016/0024107 A1 | 1/2016 | Clarke et al. |
| 2016/0053175 A1 | 2/2016 | Song et al. |
| 2016/0122374 A1 | 5/2016 | Chun et al. |
| 2016/0244668 A1 | 8/2016 | Saito et al. |
| 2016/0257657 A1 | 9/2016 | Wipf et al. |
| 2017/0071964 A1 | 3/2017 | Clarke et al. |
| 2017/0186964 A1 | 6/2017 | Cho et al. |
| 2018/0002366 A1 | 1/2018 | Girijavallabhan et al. |
| 2018/0044369 A1 | 2/2018 | Beigelman et al. |
| 2018/0079774 A1 | 3/2018 | Beigelman et al. |
| 2018/0226580 A1 | 8/2018 | Fitzgerald et al. |
| 2019/0185748 A1 | 6/2019 | Liao |
| 2019/0185754 A1 | 6/2019 | Archetti et al. |
| 2019/0241807 A1 | 8/2019 | Mizusaki et al. |
| 2021/0060051 A1 | 3/2021 | Schinazi et al. |
| 2021/0284670 A1 | 9/2021 | Chin et al. |
| 2021/0292348 A1 | 9/2021 | Byun et al. |
| 2023/0295201 A1 | 9/2023 | Byun |

FOREIGN PATENT DOCUMENTS

| | | |
|---|---|---|
| CN | 102603836 A | 7/2012 |
| CN | 103709220 A | 4/2014 |
| CN | 104086612 A | 10/2014 |
| CN | 105646629 A | 6/2016 |
| CN | 105777580 A | 7/2016 |
| CN | 106518766 A | 3/2017 |
| CN | 106518767 A | 3/2017 |
| CN | 106892920 A | 6/2017 |
| CN | 107286190 A | 10/2017 |
| CN | 108276352 A | 7/2018 |
| CN | 109748921 A | 5/2019 |
| CN | 109748943 A | 5/2019 |
| CN | 109748944 A | 5/2019 |
| CN | 110215456 A | 9/2019 |
| CN | 110330540 A | 10/2019 |
| CN | 110724174 A | 1/2020 |
| CN | 110776512 A | 2/2020 |
| CN | 111620909 A | 9/2020 |
| DE | 2626792 A1 | 12/1977 |
| DE | 3528753 A1 | 2/1987 |
| DE | 4232852 A1 | 3/1994 |
| DE | 19934799 A1 | 2/2001 |
| DE | 10064823 A1 | 6/2002 |
| EP | 0284952 A2 | 10/1988 |
| EP | 0419944 A2 | 4/1991 |
| EP | 0458214 A1 | 11/1991 |
| EP | 0682098 A2 | 11/1995 |
| EP | 0924265 A2 | 6/1999 |
| EP | 1046631 A1 | 10/2000 |
| EP | 1170353 A2 | 1/2002 |
| EP | 1593713 A1 | 11/2005 |
| EP | 1975718 A2 | 10/2008 |
| EP | 1978077 A1 | 10/2008 |
| EP | 2098226 A1 | 9/2009 |
| EP | 2388069 A1 | 11/2011 |
| EP | 2778169 A1 | 9/2014 |
| EP | 2896678 A1 | 7/2015 |
| EP | 2980182 A1 | 2/2016 |
| FR | 2354774 A1 | 1/1978 |
| FR | 2669639 A1 | 5/1992 |
| IN | 167775 B | 12/1990 |
| JP | S6286363 A | 4/1987 |
| JP | H0931092 A | 2/1997 |
| JP | H09328497 A | 12/1997 |
| JP | 2002326995 A | 11/2002 |
| JP | 2002326996 A | 11/2002 |
| JP | 2003246770 A | 9/2003 |
| JP | 2004315613 A | 11/2004 |
| JP | 2005120172 A | 5/2005 |
| JP | 2006232875 A | 9/2006 |
| JP | 2008007634 A | 1/2008 |
| JP | 2012216832 A | 11/2012 |
| JP | 5295692 B2 | 9/2013 |
| JP | 2014145852 A | 8/2014 |
| JP | 2016132779 A | 7/2016 |
| JP | 2018044028 A | 3/2018 |
| JP | 2018203945 A | 12/2018 |
| KR | 20120135501 A | 12/2012 |
| KR | 20160098975 A | 8/2016 |
| KR | 20160110899 A | 9/2016 |
| KR | 20160110900 A | 9/2016 |
| KR | 20190041918 A | 4/2019 |
| KR | 20190076339 A | 7/2019 |
| NL | 7606413 A | 12/1977 |
| WO | 8807043 A | 9/1988 |
| WO | 9110671 A1 | 7/1991 |
| WO | 9201695 A1 | 2/1992 |
| WO | 9201696 A1 | 2/1992 |
| WO | 9214805 A1 | 9/1992 |
| WO | 9316075 A1 | 8/1993 |
| WO | 9614329 A1 | 5/1996 |
| WO | 9640705 A1 | 12/1996 |
| WO | 9816184 A2 | 4/1998 |
| WO | 9900399 A1 | 1/1999 |
| WO | 9914226 A2 | 3/1999 |
| WO | 9926933 A1 | 6/1999 |
| WO | 9926941 A1 | 6/1999 |
| WO | 9951565 A1 | 10/1999 |
| WO | 9961583 A2 | 12/1999 |
| WO | 0001381 A1 | 1/2000 |
| WO | 0032152 A2 | 6/2000 |
| WO | 0034276 A1 | 6/2000 |
| WO | 0063154 A1 | 10/2000 |
| WO | 0066604 A1 | 11/2000 |
| WO | 0100197 A2 | 1/2001 |
| WO | 0110842 A2 | 2/2001 |
| WO | 0114320 A1 | 3/2001 |
| WO | 0119841 A1 | 3/2001 |
| WO | 0121577 A2 | 3/2001 |
| WO | 0123357 A2 | 4/2001 |
| WO | 0147862 A1 | 7/2001 |
| WO | 0164642 A2 | 9/2001 |
| WO | 0177091 A2 | 10/2001 |
| WO | 0207516 A2 | 1/2002 |
| WO | 0234711 A1 | 5/2002 |
| WO | 0234736 A1 | 5/2002 |

(56) References Cited

FOREIGN PATENT DOCUMENTS

| | | |
|---|---|---|
| WO | 0239987 A2 | 5/2002 |
| WO | 02062766 A2 | 8/2002 |
| WO | 02094185 A2 | 11/2002 |
| WO | 02100415 A2 | 12/2002 |
| WO | 03039523 A2 | 5/2003 |
| WO | 03041649 A2 | 5/2003 |
| WO | 03049772 A2 | 6/2003 |
| WO | 03088908 A2 | 10/2003 |
| WO | 03090748 A1 | 11/2003 |
| WO | 03091262 A1 | 11/2003 |
| WO | 2004002999 A2 | 1/2004 |
| WO | 2004007472 A1 | 1/2004 |
| WO | 2004014312 A2 | 2/2004 |
| WO | 2004037159 A2 | 5/2004 |
| WO | 2004041752 A2 | 5/2004 |
| WO | 2004080966 A1 | 9/2004 |
| WO | 2004083177 A2 | 9/2004 |
| WO | 2004083263 A1 | 9/2004 |
| WO | 2004087153 A2 | 10/2004 |
| WO | 2004091499 A2 | 10/2004 |
| WO | 2004106356 A1 | 12/2004 |
| WO | 2004110350 A2 | 12/2004 |
| WO | 2005020885 A2 | 3/2005 |
| WO | 2005021568 A2 | 3/2005 |
| WO | 2005023771 A1 | 3/2005 |
| WO | 2005025515 A2 | 3/2005 |
| WO | 2005040135 A1 | 5/2005 |
| WO | 2005058832 A1 | 6/2005 |
| WO | 2005093476 A1 | 10/2005 |
| WO | 2005095544 A1 | 10/2005 |
| WO | 2005097052 A1 | 10/2005 |
| WO | 2005111099 A1 | 11/2005 |
| WO | 2006001463 A1 | 1/2006 |
| WO | 2006006490 A1 | 1/2006 |
| WO | 2006008438 A1 | 1/2006 |
| WO | 2006016101 A1 | 2/2006 |
| WO | 2006030193 A1 | 3/2006 |
| WO | 2006038594 A1 | 4/2006 |
| WO | 2006048634 A1 | 5/2006 |
| WO | 2006061094 A1 | 6/2006 |
| WO | 2006063717 A2 | 6/2006 |
| WO | 2006066074 A2 | 6/2006 |
| WO | 2006094347 A1 | 9/2006 |
| WO | 2006098380 A1 | 9/2006 |
| WO | 2006105440 A2 | 10/2006 |
| WO | 2006110656 A2 | 10/2006 |
| WO | 2006119800 A1 | 11/2006 |
| WO | 2006130217 A2 | 12/2006 |
| WO | 2007007588 A1 | 1/2007 |
| WO | 2007011759 A2 | 1/2007 |
| WO | 2007024021 A1 | 3/2007 |
| WO | 2007031185 A1 | 3/2007 |
| WO | 2007056143 A2 | 5/2007 |
| WO | 2007056170 A2 | 5/2007 |
| WO | 2007076034 A2 | 7/2007 |
| WO | 2007084667 A2 | 7/2007 |
| WO | 2007095188 A2 | 8/2007 |
| WO | 2007125320 A1 | 11/2007 |
| WO | 2007130783 A2 | 11/2007 |
| WO | 2008001195 A2 | 1/2008 |
| WO | 2008011557 A2 | 1/2008 |
| WO | 2008012555 A2 | 1/2008 |
| WO | 2008021388 A1 | 2/2008 |
| WO | 2008024364 A2 | 2/2008 |
| WO | 2008082601 A2 | 7/2008 |
| WO | 2008092006 A2 | 7/2008 |
| WO | 2008095040 A2 | 8/2008 |
| WO | 2008109177 A2 | 9/2008 |
| WO | 2008109180 A2 | 9/2008 |
| WO | 2008109181 A2 | 9/2008 |
| WO | 2008117047 A1 | 10/2008 |
| WO | 2008121360 A1 | 10/2008 |
| WO | 2008133966 A1 | 11/2008 |
| WO | 2008151437 A1 | 12/2008 |
| WO | 2009001097 A2 | 12/2008 |
| WO | 2009009951 A1 | 1/2009 |
| WO | 2009011228 A1 | 1/2009 |
| WO | 2009011229 A1 | 1/2009 |
| WO | 2009067409 A1 | 5/2009 |
| WO | 2009069095 A2 | 6/2009 |
| WO | 2009076593 A1 | 6/2009 |
| WO | 2009076618 A2 | 6/2009 |
| WO | 2009086192 A1 | 7/2009 |
| WO | 2009086201 A1 | 7/2009 |
| WO | 2009111653 A2 | 9/2009 |
| WO | 2009132123 A1 | 10/2009 |
| WO | 2009132135 A1 | 10/2009 |
| WO | 2009151921 A1 | 12/2009 |
| WO | 2009152095 A2 | 12/2009 |
| WO | 2010001174 A1 | 1/2010 |
| WO | 2010007116 A2 | 1/2010 |
| WO | 2010026153 A1 | 3/2010 |
| WO | 2010036407 A2 | 4/2010 |
| WO | 2010060952 A1 | 6/2010 |
| WO | 2010073126 A2 | 7/2010 |
| WO | 2010084115 A2 | 7/2010 |
| WO | 2010091386 | 8/2010 |
| WO | 2010108135 A1 | 9/2010 |
| WO | 2010108140 A1 | 9/2010 |
| WO | 2010145778 A1 | 12/2010 |
| WO | 2011005860 A2 | 1/2011 |
| WO | 2011015037 A1 | 2/2011 |
| WO | 2011016430 A1 | 2/2011 |
| WO | 2011031896 A2 | 3/2011 |
| WO | 2011032169 A2 | 3/2011 |
| WO | 2011035231 A1 | 3/2011 |
| WO | 2011035250 A1 | 3/2011 |
| WO | 2011035842 A1 | 3/2011 |
| WO | 2011036557 A1 | 3/2011 |
| WO | 2011038207 A1 | 3/2011 |
| WO | 2011057214 A2 | 5/2011 |
| WO | 2011086075 A1 | 7/2011 |
| WO | 2011097300 A1 | 8/2011 |
| WO | 2011100131 A2 | 8/2011 |
| WO | 2011109799 A1 | 9/2011 |
| WO | 2011119869 A1 | 9/2011 |
| WO | 2011146401 A1 | 11/2011 |
| WO | 2011150288 A1 | 12/2011 |
| WO | 2011156632 A2 | 12/2011 |
| WO | 2012012465 A1 | 1/2012 |
| WO | 2012012776 A1 | 1/2012 |
| WO | 2012031539 A1 | 3/2012 |
| WO | 2012034626 A1 | 3/2012 |
| WO | 2012037038 A1 | 3/2012 |
| WO | 2012040124 A1 | 3/2012 |
| WO | 2012040126 A1 | 3/2012 |
| WO | 2012040127 A1 | 3/2012 |
| WO | 2012068340 A2 | 5/2012 |
| WO | 2012083048 A2 | 6/2012 |
| WO | 2012087596 A1 | 6/2012 |
| WO | 2012088155 A1 | 6/2012 |
| WO | 2012088438 A1 | 6/2012 |
| WO | 2012092471 A2 | 7/2012 |
| WO | 2012121973 A1 | 9/2012 |
| WO | 2012128944 A1 | 9/2012 |
| WO | 2012139028 A2 | 10/2012 |
| WO | 2012142075 A1 | 10/2012 |
| WO | 2012142085 A1 | 10/2012 |
| WO | 2012142523 A2 | 10/2012 |
| WO | 2012160392 A1 | 11/2012 |
| WO | 2012168348 | 12/2012 |
| WO | 2013000855 A1 | 1/2013 |
| WO | 2013007586 A1 | 1/2013 |
| WO | 2013030288 A1 | 3/2013 |
| WO | 2013033270 A2 | 3/2013 |
| WO | 2013040492 A2 | 3/2013 |
| WO | 2013040568 A1 | 3/2013 |
| WO | 2013044030 A1 | 3/2013 |
| WO | 2013056132 A2 | 4/2013 |
| WO | 2013072466 A1 | 5/2013 |
| WO | 2013087765 A1 | 6/2013 |
| WO | 2013090420 A2 | 6/2013 |
| WO | 2013096679 A1 | 6/2013 |
| WO | 2013096680 A1 | 6/2013 |

(56) References Cited

FOREIGN PATENT DOCUMENTS

| | | |
|---|---|---|
| WO | 2013101552 A1 | 7/2013 |
| WO | 2013135339 A2 | 9/2013 |
| WO | 2013138236 A1 | 9/2013 |
| WO | 2013142124 A1 | 9/2013 |
| WO | 2013142157 A1 | 9/2013 |
| WO | 2013142159 A1 | 9/2013 |
| WO | 2013142525 A1 | 9/2013 |
| WO | 2013147795 A1 | 10/2013 |
| WO | 2013151975 A1 | 10/2013 |
| WO | 2013182262 A1 | 12/2013 |
| WO | 2014005125 A2 | 1/2014 |
| WO | 2014008236 A1 | 1/2014 |
| WO | 2014015936 A1 | 1/2014 |
| WO | 2014026198 A1 | 2/2014 |
| WO | 2014031872 A2 | 2/2014 |
| WO | 2014035140 A2 | 3/2014 |
| WO | 2014048998 A1 | 4/2014 |
| WO | 2014057095 A1 | 4/2014 |
| WO | 2014058801 A1 | 4/2014 |
| WO | 2014059901 A1 | 4/2014 |
| WO | 2014059902 A1 | 4/2014 |
| WO | 2014090369 A1 | 6/2014 |
| WO | 2014100498 A1 | 6/2014 |
| WO | 2014100505 A1 | 6/2014 |
| WO | 2014102077 A1 | 7/2014 |
| WO | 2014124458 A1 | 8/2014 |
| WO | 2014134127 A1 | 9/2014 |
| WO | 2014134251 A1 | 9/2014 |
| WO | 2014149164 A1 | 9/2014 |
| WO | 2014160012 A2 | 10/2014 |
| WO | 2014209979 A1 | 12/2014 |
| WO | 2015003146 A1 | 1/2015 |
| WO | 2015006280 A1 | 1/2015 |
| WO | 2015016187 A1 | 2/2015 |
| WO | 2015024120 A1 | 2/2015 |
| WO | 2015031710 A1 | 3/2015 |
| WO | 2015038596 A1 | 3/2015 |
| WO | 2015046827 A1 | 4/2015 |
| WO | 2015051169 A2 | 4/2015 |
| WO | 2015061742 A2 | 4/2015 |
| WO | 2015069939 A1 | 5/2015 |
| WO | 2015089511 A2 | 6/2015 |
| WO | 2015118898 A1 | 8/2015 |
| WO | 2015120237 A2 | 8/2015 |
| WO | 2015129672 A1 | 9/2015 |
| WO | 2015143712 A1 | 10/2015 |
| WO | 2015148746 A1 | 10/2015 |
| WO | 2015148869 A1 | 10/2015 |
| WO | 2015160251 A1 | 10/2015 |
| WO | 2015196118 A1 | 12/2015 |
| WO | 2015196128 A2 | 12/2015 |
| WO | 2015196130 A2 | 12/2015 |
| WO | 2015198915 A1 | 12/2015 |
| WO | 2015200205 A1 | 12/2015 |
| WO | 2015200219 A1 | 12/2015 |
| WO | 2016010026 A1 | 1/2016 |
| WO | 2016018697 A1 | 2/2016 |
| WO | 2016029186 A1 | 2/2016 |
| WO | 2016031406 A1 | 3/2016 |
| WO | 2016041877 A1 | 3/2016 |
| WO | 2016066582 A1 | 5/2016 |
| WO | 2016069825 | 5/2016 |
| WO | 2016069826 | 5/2016 |
| WO | 2016069827 A1 | 5/2016 |
| WO | 2016069975 A1 | 5/2016 |
| WO | 2016070952 A1 | 5/2016 |
| WO | 2016074762 A1 | 5/2016 |
| WO | 2016096076 A1 | 6/2016 |
| WO | 2016100441 A1 | 6/2016 |
| WO | 2016100569 A1 | 6/2016 |
| WO | 2016107664 A1 | 7/2016 |
| WO | 2016115222 A1 | 7/2016 |
| WO | 2016116124 A1 | 7/2016 |
| WO | 2016116254 A1 | 7/2016 |
| WO | 2016116508 A1 | 7/2016 |
| WO | 2016117271 A1 | 7/2016 |
| WO | 2016145142 A1 | 9/2016 |
| WO | 2016148170 A1 | 9/2016 |
| WO | 2016152340 A1 | 9/2016 |
| WO | 2016161176 A1 | 10/2016 |
| WO | 2016162644 A1 | 10/2016 |
| WO | 2016170948 A1 | 10/2016 |
| WO | 2016172631 A2 | 10/2016 |
| WO | 2016178876 A2 | 11/2016 |
| WO | 2016184361 A1 | 11/2016 |
| WO | 2016192902 A1 | 12/2016 |
| WO | 2017005673 A1 | 1/2017 |
| WO | 2017019817 A1 | 2/2017 |
| WO | 2017019822 A1 | 2/2017 |
| WO | 2017019830 A1 | 2/2017 |
| WO | 2017023894 A1 | 2/2017 |
| WO | 2017024310 A1 | 2/2017 |
| WO | 2017027646 A1 | 2/2017 |
| WO | 2017032840 A1 | 3/2017 |
| WO | 2017041893 A1 | 3/2017 |
| WO | 2017045612 A1 | 3/2017 |
| WO | 2017045615 A1 | 3/2017 |
| WO | 2017045616 A1 | 3/2017 |
| WO | 2017045740 A1 | 3/2017 |
| WO | 2017049060 A1 | 3/2017 |
| WO | 2017058807 A1 | 4/2017 |
| WO | 2017059357 A1 | 4/2017 |
| WO | 2017066781 A1 | 4/2017 |
| WO | 2017066782 A1 | 4/2017 |
| WO | 2017066791 A1 | 4/2017 |
| WO | 2017066793 A1 | 4/2017 |
| WO | 2017066797 A1 | 4/2017 |
| WO | 2017068875 A1 | 4/2017 |
| WO | 2017073931 A1 | 5/2017 |
| WO | 2017073932 A1 | 5/2017 |
| WO | 2017073933 A1 | 5/2017 |
| WO | 2017091767 A2 | 6/2017 |
| WO | 2017093214 A1 | 6/2017 |
| WO | 2017097401 A1 | 6/2017 |
| WO | 2017153186 A1 | 9/2017 |
| WO | 2017156262 A1 | 9/2017 |
| WO | 2017161028 A1 | 9/2017 |
| WO | 2017165489 A1 | 9/2017 |
| WO | 2017184668 A1 | 10/2017 |
| WO | 2017205980 A1 | 12/2017 |
| WO | 2017207993 A1 | 12/2017 |
| WO | 2018015323 A2 | 1/2018 |
| WO | 2018031818 A2 | 2/2018 |
| WO | 2018065356 A1 | 4/2018 |
| WO | 2018067615 A1 | 4/2018 |
| WO | 2018098206 A1 | 5/2018 |
| WO | 2018106818 A1 | 6/2018 |
| WO | 2018106820 A1 | 6/2018 |
| WO | 2018110529 A1 | 6/2018 |
| WO | 2018116901 A1 | 6/2018 |
| WO | 2018119263 A1 | 6/2018 |
| WO | 2018138685 A2 | 8/2018 |
| WO | 2018169946 A1 | 9/2018 |
| WO | 2018175746 A1 | 9/2018 |
| WO | 2018183635 A1 | 10/2018 |
| WO | 2018184590 A1 | 10/2018 |
| WO | 2018189134 A1 | 10/2018 |
| WO | 2018204198 A1 | 11/2018 |
| WO | 2018208667 A1 | 11/2018 |
| WO | 2018213185 A1 | 11/2018 |
| WO | 2018218171 A1 | 11/2018 |
| WO | 2018218281 A1 | 12/2018 |
| WO | 2018222172 A1 | 12/2018 |
| WO | 2018226976 A1 | 12/2018 |
| WO | 2018237194 A1 | 12/2018 |
| WO | 2019014247 A1 | 1/2019 |
| WO | 2019018185 A1 | 1/2019 |
| WO | 2019051269 A1 | 3/2019 |
| WO | 2019052935 A1 | 3/2019 |
| WO | 2019053696 A1 | 3/2019 |
| WO | 2019084271 A1 | 5/2019 |
| WO | 2019086400 A1 | 5/2019 |
| WO | 2019092171 A1 | 5/2019 |
| WO | 2019098109 A1 | 5/2019 |

(56) References Cited

FOREIGN PATENT DOCUMENTS

| WO | 2019125974 A1 | 6/2019 |
|---|---|---|
| WO | 2019129059 A1 | 7/2019 |
| WO | 2019133712 A1 | 7/2019 |
| WO | 2019154953 A1 | 8/2019 |
| WO | 2019154956 A1 | 8/2019 |
| WO | 2019173682 A1 | 9/2019 |
| WO | 2019195056 A1 | 10/2019 |
| WO | 2019215076 A1 | 11/2019 |
| WO | 2019218797 A1 | 11/2019 |
| WO | 2020032152 A1 | 2/2020 |
| WO | 2020033413 A2 | 2/2020 |
| WO | 2021167882 A1 | 8/2021 |
| WO | 2021168004 A1 | 8/2021 |
| WO | 2021168038 A1 | 8/2021 |

OTHER PUBLICATIONS

U.S. Appl. No. 17/176,497, filed Feb. 16, 2021, Byun et al.
International Preliminary Report on Patentability received for PCT Application No. PCT/US2021/018169, mailed on Dec. 15, 2021, 20 pages.
International Search Report and Written Opinion received for PCT Application No. PCT/US2021/018169, mailed on Apr. 26, 2021, 19 pages.
International Search Report and Written Opinion received for PCT Application No. PCT/US2021/018410, mailed on May 10, 2021, 11 pages.
International Search Report and Written Opinion received for PCT Application No. PCT/US2021/018415, mailed on May 11, 2021, 14 pages.
International Search Report and Written Opinion received for PCT Application No. PCT/US2021/018458, mailed on May 18, 2021, 17 pages.
Cockerill et al. (2019) "State of the Art in Respiratory Syncytial Virus Drug Discovery and Development", Journal of Medicinal Chemistry, 62(7):3206-3227.
Colombo et al. (1985) "Asymetric Dihydroxylations via Chiral Oxazolidines", Tetrahedron Letters, 26(44):5459-5462.
Griffon et al. (2001) "Synthesis And Antiproliferative Activity Of Some 4'-C-Hydroxymethyl-A- And -B-D-Arabino-Pentofuranosyl Pyrimidine Nucleosides", Nucleosides, Nucleotides & Nucleic Acids, 20(4-7):649-652.
Griffon et al. (2006) "Synthesis and Biological Evaluation of Some 4'-C-(Hydroxymethyl)-α- and -β-D-Arabinofuranosyl Pyrimidine and Adenine Nucleosides", Collection of Czechoslovak Chemical Communications, 71(7):1063-1087.
Koshkin et al. (Apr. 2, 1998) "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition", Tetrahedron, 54(14):3607-3630.
Leisvuori Anna (Sep. 2015) "Prodrug Strategies of Antiviral Nucleotides: Studies on Enzymatically And Thermally Removable Phosphate Protecting Groups", University of Turku, Turku, Finland, 86 pages.
Musich et al. (1978) "Synthesis of Anthopleurine, The Alarm Pheromone from Anthopleura Elegantissima", Journal of the American Chemical Society, 100(15):4865-4872.
Overend et al. (1970) "Branched Chain Sugars Part 12 Branched Sugars Derived from Methyl 2, 3-O-Isopropylidene-β-L-erythro-Pentopyranosid-4-Ulose and a Synthesis of L-Apiose", Carbohydrate Research, 15(2):185-195.

Patil et al. (1994) "4-Aza-7,9-Dideazaadenosine, a New Cytotoxic Synthetic C-Nucleoside Analogue of Adenosine", Tetrahedron Letters, 35(30):5339-5342.
Patil et al. (1994) "Synthesis of Pyrrolo[2,1-f][1,2,4]triazine Congeners of Nucleic Acid Purines via the N-Amination of 2-Substituted Pyrroles", Journal of Heterocyclic Chemistry, 31(4):781-786.
Shrestha et al. (2011) "Synthesis and Properties of a Bridged Nucleic Acid with a Perhydro-1,2-oxazin-3-one Ring", Journal of Organic Chemistry, 76(24):9891-9899.
Timpe et al. (Jan. 1975) "3-desoxyhex-2-enono-1,4-lactone aus D-hexofuran(osid)-urono-6,3-lactonen", Carbohydrate Research, 39(1):53-60.
Waga et al. (Jan. 26, 1993) "Synthesis of 4'-C-Methylnucleosides", Bioscience, Biotechnology, Biochemistry, 57(9):1433-1438.
Wenska et al. (2007) "Synthesis of Conformationally Constrained 2'-N,4'-C-Ethylene-Bridged Adenosine (aza-ENA-A)", Heterocycles, 73(1):303-324.
Youssefyeh et al. (1977) "Synthetic Routes to 4'-hydroxymethylnucleosides", Tetrahedron Letters, 18(5):435-438.
Feng et al. (Apr. 2014) "Inhibition of Hepatitis C Virus Replication by GS-6620, a Potent C-Nucleoside Monophosphate Prodrug", Antimicrobial Agents and Chemotherapy, 58(4):1930-1942.
Office Action and Search Report in Taiwan Application No. 110105140, mailed on Dec. 7, 2021, 7 pages (3 pages of English Translation and 4 pages of Taiwan Office Action).
Office Action and Search Report in Taiwan Application No. 110105397, mailed on Dec. 3, 2021, 11 pages (5 pages of English Translation and 6 pages of Taiwan Office Action).
First Office Action and Search Report in Taiwan (ROC) Application 110104869 mailed on Jan. 24, 2022, 7 pages (3 pages of English Translation and 4 pages of Taiwan Office Action).
First Office Action and Search Report in Taiwan (ROC) Application 110105126 mailed on Jan. 6, 2022, 7 pages (3 pages of English Translation and 4 pages of Taiwan Office Action).
Non-Final Office Action in U.S. Appl. No. 17/176,497 dated Jul. 27, 2022, 7 pages.
International Preliminary Report on Patentability for PCT Application No. PCT/US2021/018458 dated Sep. 1, 2022, 12 pages.
International Preliminary Report on Patentability for PCT Application No. PCT/US2021/018415 dated Sep. 1, 2022, 9 pages.
European Patent Office Communication for EP Application No. 21710378.7 dated Sep. 27, 2022, 3 pages.
European Patent Office Communication for EP Application No. 21712279.5 dated Sep. 28, 2022, 3 pages.
CAPLUS Chem Abs Acc. No. 2015:832846 Document 162:643613.
Notice of Allowance in Taiwan (ROC) Application No. 110104869, dated Sep. 30, 2022, 3 pages.
Notice of Allowance in Taiwan (ROC) Application No. 110105126, dated Nov. 22, 2022, 3 pages.
Non Final Office Action for U.S. Appl. No. 17/178,463 dated Jan. 18, 2023, 11 pages.
"Clinical Pharmacotherapeutics", edited by Yaocheng Rui et al., published on Apr. 30, 2001, p. 337, "Chronic Obstructive Pulmonary Disease".
1st Examination Report in Australia Appl. No. 2021221980, Aug. 4, 2023.
Office Action in Canada Appl. No. 3172629, mailed Oct. 11, 2023.
Office Action in India Appl. No. 202217052438, dated Oct. 27, 2023.
Office Action in Japan Appl. No. 2022-549448, Aug. 9, 2023.

\* cited by examiner

ANTIVIRAL COMPOUNDS

CROSS-REFERENCES TO RELATED APPLICATIONS

This application claims the benefit of priority to U.S. Provisional Patent Application No. 62/977,969, filed 18 Feb. 2020 and titled "Antiviral Compounds," the entirety of which is incorporated by reference herein.

SEQUENCE LISTING

The instant application contains a Sequence Listing which has been submitted electronically in ASCII format and is hereby incorporated by reference in its entirety. Said ASCII copy, created on Feb. 17, 2021, is named 1307-US—NP_SL.txt and is 1,448 bytes in size.

BACKGROUND OF THE INVENTION

Pneumoviridae viruses are negative-sense, single-stranded, RNA viruses that are responsible for many prevalent human and animal diseases. The Pneumoviridae family of viruses includes human respiratory syncytial virus (HRSV) and human metapneumovirus. Almost all children will have had an HRSV infection by their second birthday. HRSV is the major cause of lower respiratory tract infections in infancy and childhood with 0.5% to 2% of those infected requiring hospitalization.

No vaccine to prevent HRSV infection is currently available. The monoclonal antibody palivizumab is available for immunoprophylaxis, but its use is restricted to infants at high risk, e.g., premature infants or those with either congenital heart or lung disease, and the cost for general use is often prohibitive. In addition, nucleoside analog ribavirin has been approved as the only antiviral agent to treat HRSV infections but has limited efficacy. Therefore, there is a need for anti-Pneumoviridae therapeutics.

The elderly and adults with chronic heart, lung disease or those that are immunosuppressed also have a high risk for developing severe HRSV disease (http://www.cdc.gov/rsv/index.html). In particular, patients with chronic respiratory diseases, such as chronic obstructive pulmonary disorder (COPD), are at high risk for developing acute respiratory exacerbations. Acute respiratory exacerbations are a major cause of morbidity, mortality, and reduced quality of life for COPD patients (Frickmann, Eur. J. Microbiol. Immun. 2012 Sep. 2(3): 176-185).

About one-half to two-thirds of respiratory exacerbations in COPD patients are due to viral infections. Some common viral pathogens responsible for such respiratory exacerbations include but are not limited to HRSV, human metapneumovirus (HMPV), and human rhinovirus (HRV). COPD patients with infectious exacerbations generally undergo longer hospitalization periods and suffer greater lung impairment than those with non-infectious exacerbations (Frickmann, Eur. J. Microbiol. Immun. 2012 Sep. 2(3): 176-185).

There remains a need for new antiviral agents useful in treating Pneumoviridae viral infections, such as HRSV infections, that are effective and have acceptable toxicity profiles.

WO2015/069939, published May 14, 2015, discloses compounds useful for treating Pneumovirinae viral infections. WO2015/069939 relates, among other things, to compounds of the following formula, or a pharmaceutically acceptable salt thereof:

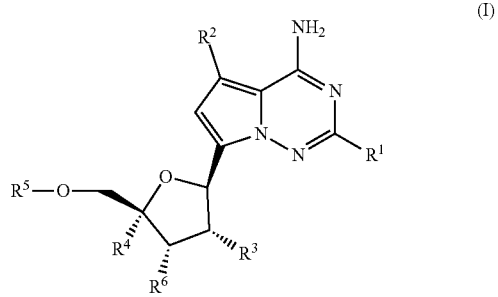

wherein:
$R^1$ is H or F;
$R^2$ is H or F;
$R^3$ is OH or F;
$R^4$ is CN, $C_1$-$C_4$ alkyl, $C_2$-$C_4$ alkenyl, $C_2$-$C_4$ alkynyl, $C_3$-$C_4$ cycloalkyl, azido, halogen, or $C_1$-$C_2$ haloalkyl;
$R^6$ is OH;
$R^5$ is selected from the group of H and:

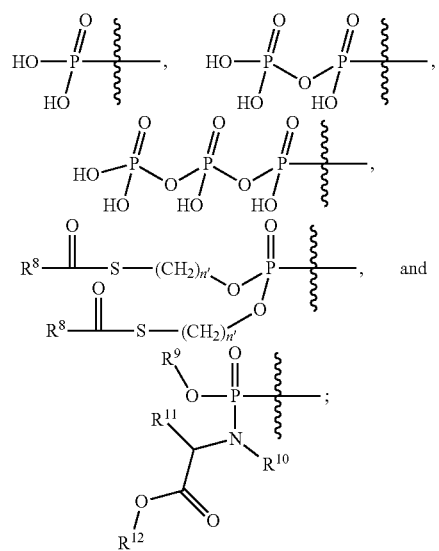

wherein:
n' is selected from 1, 2, 3, and 4;
$R^8$ is selected from $C_1$-$C_8$ alkyl, —O—$C_1$-$C_8$ alkyl, benzyl, —O-benzyl, —$CH_2$—$C_3$-$C_6$ cycloalkyl, —O—$CH_2$—$C_3$-$C_6$ cycloalkyl, and $CF_3$;
$R^9$ is selected from phenyl, 1-naphthyl, 2-naphthyl,

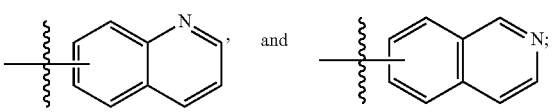

$R^{10}$ is selected from H and $CH_3$;
$R^{11}$ is selected from H or $C_1$-$C_6$ alkyl;
$R^{12}$ is selected from H, $C_1$-$C_6$ alkyl, benzyl, $C_3$-$C_6$ cycloalkyl, and —$CH_2$—$C_3$-$C_6$ cycloalkyl.

BRIEF SUMMARY OF THE INVENTION

In one embodiment, the present disclosure provides a compound of Formula I:

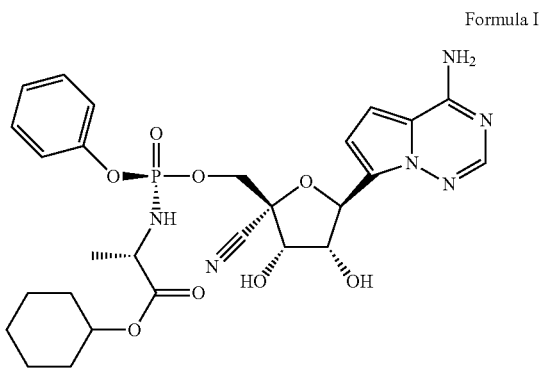 [SMILES: C[C@H](N[P@](=O)(OC[C@@]1(C#N)O[C@@H](c2ccc3c(N)ncnn23)[C@H](O)[C@@H]1O)Oc1ccccc1)C(=O)OC1CCCCC1]

Formula I or a pharmaceutically acceptable salt thereof.

In another embodiment, the present disclosure provides a pharmaceutical formulation comprising a therapeutically effective amount of the compound of the present disclosure, or a pharmaceutically acceptable salt thereof, and a pharmaceutically acceptable carrier or excipient.

In another embodiment, the present disclosure provides a method for treatment or prophylaxis of a Pneumoviridae virus infection in a human in need thereof, the method comprising administering to the human a therapeutically effective amount of the compound of the present disclosure, or a pharmaceutically acceptable salt thereof.

In another embodiment, the present disclosure provides a method for treatment or prophylaxis of a Picornaviridae virus infection in a human in need thereof, the method comprising administering to the human a therapeutically effective amount of the compound of the present disclosure, or a pharmaceutically acceptable salt thereof.

In another embodiment, the present disclosure provides a method for treatment or prophylaxis of a Flaviviridae virus infection in a human in need thereof, the method comprising administering to the human a therapeutically effective amount of the compound of the present disclosure, or a pharmaceutically acceptable salt thereof.

In another embodiment, the present disclosure provides a method for treatment or prophylaxis of a Filoviridae virus infection in a human in need thereof, the method comprising administering to the human a therapeutically effective amount of the compound of the present disclosure, or a pharmaceutically acceptable salt thereof.

In another embodiment, the present disclosure provides a method for manufacturing a medicament for treatment or prophylaxis of a Pneumoviridae virus infection in a human in need thereof, characterized in that the compound of the present disclosure, or a pharmaceutically acceptable salt thereof, is used.

In another embodiment, the present disclosure provides a method for manufacturing a medicament for treatment or prophylaxis of a Picornaviridae virus infection in a human in need thereof, characterized in that the compound of the present disclosure, or a pharmaceutically acceptable salt thereof, is used.

In another embodiment, the present disclosure provides a method for manufacturing a medicament for treatment or prophylaxis of a Flaviviridae virus infection in a human in need thereof, characterized in that the compound of the present disclosure, or a pharmaceutically acceptable salt thereof, is used.

In another embodiment, the present disclosure provides a method for manufacturing a medicament for treatment or prophylaxis of a Filoviridae virus infection in a human in need thereof, characterized in that the compound of the present disclosure, or a pharmaceutically acceptable salt thereof, is used.

In another embodiment, the present disclosure provides use of the compound of the present disclosure, or a pharmaceutically acceptable salt thereof, for the manufacture of a medicament for the treatment or prophylaxis in a human of a Pneumoviridae virus infection.

In another embodiment, the present disclosure provides use of the compound of the present disclosure, or a pharmaceutically acceptable salt thereof, for the manufacture of a medicament for the treatment or prophylaxis in a human of a Picornaviridae virus infection.

In another embodiment, the present disclosure provides use of the compound of the present disclosure, or a pharmaceutically acceptable salt thereof, for the manufacture of a medicament for the treatment or prophylaxis in a human of a Flaviviridae virus infection.

In another embodiment, the present disclosure provides use of the compound of the present disclosure, or a pharmaceutically acceptable salt thereof, for the manufacture of a medicament for the treatment or prophylaxis in a human of a Filoviridae virus infection.

In another embodiment, the present disclosure provides the compound of the present disclosure, or a pharmaceutically acceptable salt thereof, for use in the treatment or prophylaxis of a Pneumoviridae virus infection in a human in need thereof.

In another embodiment, the present disclosure provides the compound of the present disclosure, or a pharmaceutically acceptable salt thereof, for use in the treatment or prophylaxis of a Picornaviridae virus infection in a human in need thereof.

In another embodiment, the present disclosure provides the compound of the present disclosure, or a pharmaceutically acceptable salt thereof, for use in the treatment or prophylaxis of a Flaviviridae virus infection in a human in need thereof.

In another embodiment, the present disclosure provides the compound of the present disclosure, or a pharmaceutically acceptable salt thereof, for use in the treatment or prophylaxis of a Filoviridae virus infection in a human in need thereof.

In another embodiment, the present disclosure provides a method for the treatment or prophylaxis of an exacerbation of a respiratory condition by a viral infection in a human in need thereof, the method comprising administering to the human a therapeutically effective amount of the compound of the present disclosure, or a pharmaceutically acceptable salt thereof, wherein the respiratory condition is chronic obstructive pulmonary disease.

In another embodiment, the present disclosure provides a method for the treatment or prophylaxis of an exacerbation of a respiratory condition by a viral infection in a human in need thereof, the method comprising administering to the human a therapeutically effective amount of the compound of the present disclosure, or a pharmaceutically acceptable salt thereof, wherein the respiratory condition is asthma.

In another embodiment, the present disclosure provides a method for manufacturing a medicament for the treatment or prophylaxis of an exacerbation of a respiratory condition by a viral infection in a human in need thereof, characterized in that the compound of the present disclosure, or a pharmaceutically acceptable salt thereof, is used, wherein the respiratory condition is chronic obstructive pulmonary disease.

In another embodiment, the present disclosure provides a method for manufacturing a medicament for the treatment or prophylaxis of an exacerbation of a respiratory condition by a viral infection in a human in need thereof, characterized in that the compound of the present disclosure, or a pharmaceutically acceptable salt thereof, is used, wherein the respiratory condition is asthma.

In another embodiment, the present disclosure provides use of the compound of the present disclosure, or a pharmaceutically acceptable salt thereof, for the manufacture of a medicament for the treatment or prophylaxis in a human of an exacerbation of a respiratory condition by a viral infection, wherein the respiratory condition is chronic obstructive pulmonary disease.

In another embodiment, the present disclosure provides use of the compound of the present disclosure, or a pharmaceutically acceptable salt thereof, for the manufacture of a medicament for the treatment or prophylaxis in a human of an exacerbation of a respiratory condition by a viral infection, wherein the respiratory condition is asthma.

In another embodiment, the present disclosure provides the compound of the present disclosure, or a pharmaceutically acceptable salt thereof, for use in the treatment or prophylaxis of an exacerbation of a respiratory condition by a viral infection in a human in need thereof, wherein the respiratory condition is chronic obstructive pulmonary disease.

In another embodiment, the present disclosure provides the compound of the present disclosure, or a pharmaceutically acceptable salt thereof, for use in the treatment or prophylaxis of an exacerbation of a respiratory condition by a viral infection in a human in need thereof, wherein the respiratory condition is asthma.

In another embodiment, the present disclosure provides the compound of the present disclosure, or a pharmaceutically acceptable salt thereof, for use in medical therapy.

In another embodiment, the disclosure provides a method of making a compound of formula I-11:

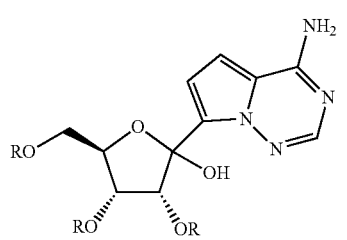

wherein the method comprises reacting:
(i) a compound of formula I-7:

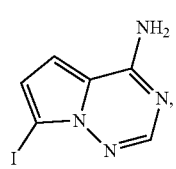

and
(ii) a compound of formula I-12:

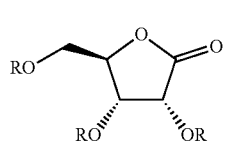

in presence of NdCl$_3$ and tetrabutylammonium chloride; wherein R is a hydroxyl protecting group. In some embodiments R is a benzyl group. In some embodiments R is a silyl protecting group. In some embodiments R is a tert-butyldimethylsilyl (TBS) group.

In another embodiment, the disclosure provides a method of making a compound of formula I-6:

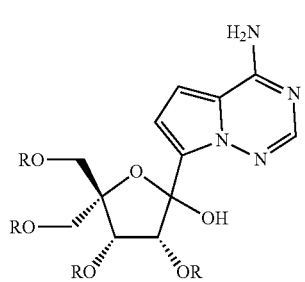

wherein the method comprises reacting:
(i) a compound of formula I-7:

and
(ii) a compound of formula I-5:

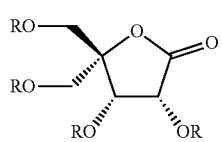

in presence of NdCl$_3$ and tetrabutylammonium chloride; wherein R is a hydroxyl protecting group. In some embodiments R is a benzyl group. In some embodiments R is a silyl protecting group. In some embodiments R is a tert-butyldimethylsilyl (TBS) group.

DETAILED DESCRIPTION OF THE INVENTION

Figure 1:
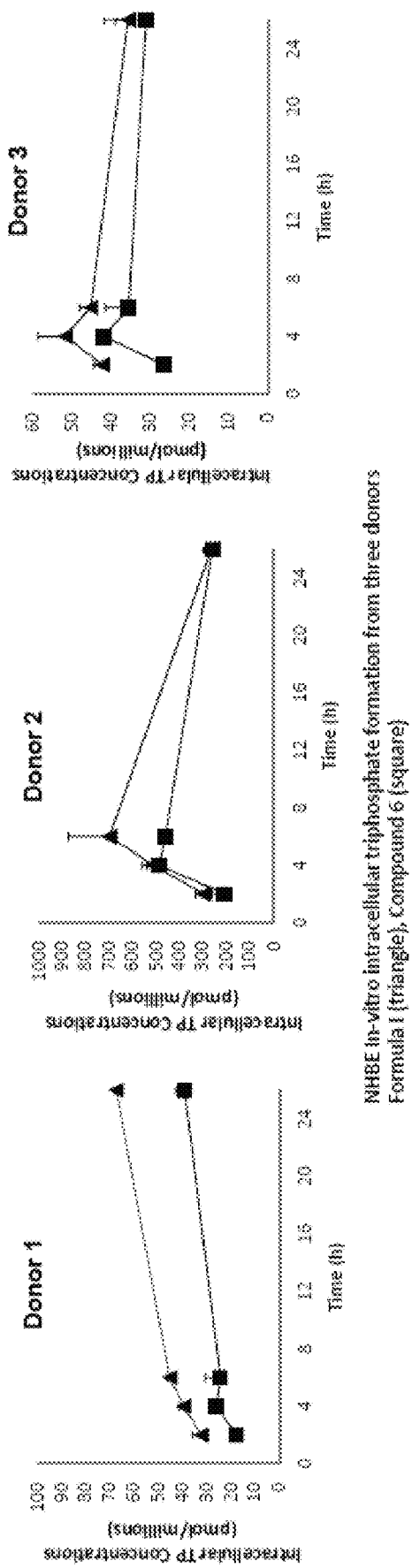
FIG. 1. Shows measurement of NHBE in-vitro intracellular triphosphate formation in three donors with the compound of Formula I and 6.

The description below is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art.

I. GENERAL

The present disclosure provides a 2',3'-hydroxy-4'-cyano nucleoside analogue for the treatment of viral infections, such as Pneumoviridae virus infections, virus infection as well as other viral infections including but not limited to Picornaviridae, Flaviviridae, Filoviridae and other virus infections.

II. DEFINITIONS

A "compound of the present disclosure" refers to the compound of Formula I.

"Pharmaceutically effective amount" refers to an amount of the compound of the present disclosure in a formulation or combination thereof, that provides the desired therapeutic or pharmaceutical result.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

"Prophylaxis" refers to preventing or retarding the progression of clinical illness in patients suffering from a viral infection.

"Respiratory condition" refers to a disease or condition such as a respiratory infection caused by a viral infection, allergic rhinitis, nasal congestion, rhinorrhea, perennial rhinitis, nasal inflammation, asthma of all types, chronic obstructive pulmonary disease (COPD), chronic or acute bronchoconstriction, chronic bronchitis, small airways obstruction, emphysema, chronic eosinophilic pneumonia, adult respiratory distress syndrome, exacerbation of airways hyperreactivity consequent to other drug therapy, pulmonary vascular disease (including pulmonary arterial hypertension), acute lung injury, bronchiectasis, sinusitis, allergic conjunctivitis, idiopathic pulmonary fibrosis or atopic dermatitis, particularly asthma or allergic rhinitis or atopic dermatitis or allergic conjunctivitis.

"Exacerbation of a respiratory condition" refers to exacerbations induced by viral infections. Representative viral infections include, but are not limited to, respiratory syncytial virus (RSV), rhinovirus and metapneumovirus.

"Therapeutically effective amount" or "effective amount" as used herein refers to an amount that is effective to elicit the desired biological or medical response, including the amount of the compound that, when administered to a subject for treating a disease, is sufficient to effect such treatment for the disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of the compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of the compound of the present disclosure within seconds or minutes. In some embodiments, a unit dose of the compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of the compound of the present disclosure. Co-administration of the compound disclosed herein with one or more additional therapeutic agents generally refers to simultaneous or sequential administration of the compound disclosed herein and one or more additional therapeutic agents, such that therapeutically effective amounts of each agent are present in the body of the patient.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds described herein may be prepared and/or formulated as pharmaceutically acceptable salts or when appropriate as a free base. Pharmaceutically acceptable salts are non-toxic salts of a free base form of a compound that possess the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Williams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4^+$ (wherein X is $C_1$-$C_4$ alkyl). Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}O$, $^{17}O$, $^{18}O$, $^{31}P$, $^{32}P$ $^{35}S$ $^{18}F$, $^{36}Cl$, $^{123}I$, and $^{125}I$, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula I, can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers, e.g., chiral carbon and phosphorous atoms, and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

"Racemates" refers to a mixture of enantiomers. The mixture can comprise equal or unequal amounts of each enantiomer.

"Stereoisomer" and "stereoisomers" refer to compounds that differ in the chirality of one or more stereocenters. Stereoisomers include enantiomers and diastereomers. The compounds may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

"Tautomer" refers to alternate forms of a compound that differ in the position of a proton, such as enol-keto and imine-enamine tautomers, or the tautomeric forms of heteroaryl groups containing a ring atom attached to both a ring —NH— and a ring =N— such as pyrazoles, imidazoles, benzimidazoles, triazoles, and tetrazoles.

Unless defined otherwise, all technical and scientific terms used herein have the same meaning as commonly understood by one of ordinary skill in the art.

"Solvate" as used herein refers to the result of the interaction of a solvent and a compound. Solvates of salts of the compounds described herein are also provided. Hydrates of the compounds described herein are also provided.

"Prodrug" as used herein refers to a derivative of a drug that upon administration to the human body is converted to the active drug according to some chemical or enzymatic pathway.

III. COMPOUNDS

The present disclosure provides a compound of Formula I:

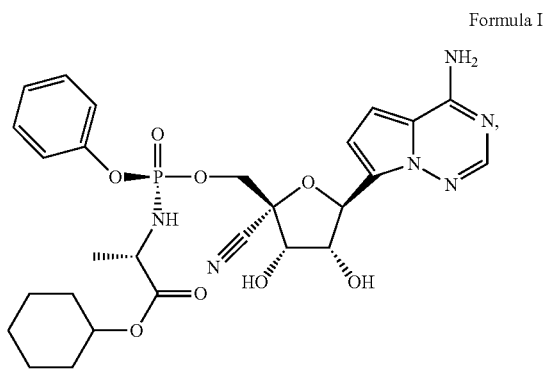 [SMILES: C[C@H](N[P@](=O)(OC[C@@]1(C#N)O[C@@H](c2ccc3c(N)ncnn23)[C@H](O)[C@@H]1O)Oc1ccccc1)C(=O)OC1CCCCC1]

Formula I or a pharmaceutically acceptable salt thereof.

Also falling within the scope herein are the in vivo metabolic products of the compound of Formula I, or the pharmaceutically acceptable salt thereof, described herein, to the extent such products are novel and nonobvious over the prior art. Such products may result for example from the oxidation, reduction, hydrolysis, amidation, esterification and the like of the administered compound, primarily due to enzymatic processes. Accordingly, included are novel and nonobvious compounds produced by a process comprising contacting a compound with a mammal for a period of time sufficient to yield a metabolic product thereof. Such products typically are identified by preparing a radiolabelled (e.g., $^{14}C$ or $^{3}H$) compound, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compound of Formula I even if they possess no antiviral activity of their own.

It is a desirable goal to discover a compound, or a pharmaceutically acceptable salt thereof, having a lower $EC_{50}$ value. The $EC_{50}$ value refers to the concentration of a compound in an assay that achieves 50% of the maximum efficacy. A compound with lower $EC_{50}$ achieves similar efficacy with lower compound concentration relative to a compound with a higher $EC_{50}$. Thus a lower $EC_{50}$ is generally preferred for drug development.

It is additionally desirable to discover a compound, or a pharmaceutically acceptable salt thereof, with high selectivity index (SI). The SI is a ratio that measures the window between cytotoxicity and antiviral activity (AVA) by dividing the given AVA value into the TOX (toxicity) value (AVA/TOX). The higher the SI ratio, the theoretically more effective and safe a drug would be during in vivo treatment for a given viral infection. The ideal drug would be cytotoxic only at very high concentrations and have antiviral activity at very low concentrations, thus yielding a high SI value (high AVA/low TOX) and thereby able to eliminate the target virus at concentrations well below its cytotoxic concentration (Human Herpesviruses HHV-6A, HHV-6B & HHV-7 (Third Edition), Diagnosis and Clinical Management, 2014, Chapter 19, Pages 311-331).

It is also desirable to discover a compound, or a pharmaceutically acceptable salt thereof, that has good physical and/or chemical stability. An increase in overall stability of a compounds can provide an increase in circulation time in the body. With less degradation, a stable compound can be administered in lower doses and still maintain efficacy. Also, with less degradation there are less concerns about by-products from degradation of the compound. Higher stability of the drug means that more drug is available for target cells without being metabolized.

It is further desirable to discover a compound, or a pharmaceutically acceptable salt thereof, that has improved pharmacokinetic and/or pharmacodynamic profiles and long half-life. It is advantageous for a drug to have a moderate or low clearance and a long half-life, as this can lead to a good bioavailability and high systemic exposure. Reducing the clearance and increasing half-life time of a compound could reduce the daily dose required for efficacy and therefore give a better efficacy and safety profile. Thus, improved pharmacokinetic and/or pharmacodynamic profiles and long half-life can provide for better patient compliance.

It is also desirable to develop compounds with improved solubility. Lower solubility compounds are often characterized by poor adsorption and bioavailability. Low solubility compounds are also generally difficult to formulate and face development challenges leading to increase in the development cost and/or time.

It is further desirable to develop prodrug compounds that can undergo selective metabolism in the target cell and/or tissue. Selective metabolism in the target cells/tissues ensures that the active metabolite is delivered to the target cells/tissues, thereby leading to increased efficacy. This can also lead to lower dose requirement and side effects.

Advantageously, the compound of Formula I exhibits improved properties as compared to structurally related compounds described in WO2015/069939 (here after designated as compounds 1 and 2).

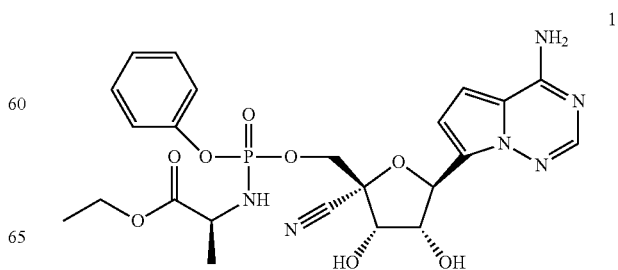

1

-continued

2

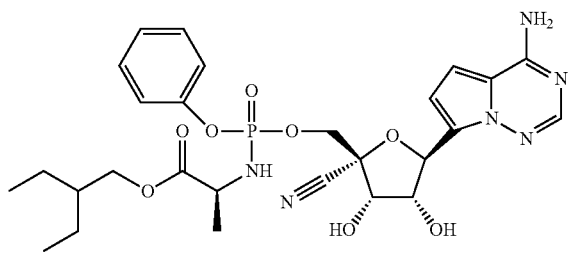

IV. PHARMACEUTICAL FORMULATIONS

In some embodiments, the present disclosure provides a pharmaceutical formulation comprising a therapeutically effective amount of the compound of the present disclosure, or a pharmaceutically acceptable salt thereof (the active ingredient), and a pharmaceutically acceptable carrier or excipient. Also provided herein is a pharmaceutical formulation comprising a therapeutically effective amount of the compound of Formula I, or a pharmaceutically acceptable salt, solvate, and/or ester thereof, and a pharmaceutically acceptable carrier or excipient.

The compound of Formula I described herein is formulated with conventional carriers and excipients, which will be selected in accord with conventional practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10.

While it is possible for the active ingredient to be administered alone it may be preferable to present them as pharmaceutical formulations. The formulations, both for veterinary and for human use, comprise the active ingredient, as above defined, together with one or more acceptable carriers and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations may conveniently be presented in unit dosage form and may be prepared by any of the methods well known in the art of pharmacy. Techniques and formulations generally are found in Remington's Pharmaceutical Sciences (Mack Publishing Co., Easton, PA). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues, e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredient may be employed with either a paraffinic or a water-miscible ointment base. Alternatively, the active ingredient may be formulated in a cream with an oil-in-water cream base.

If desired, the aqueous phase of the cream base may include, for example, at least 30% w/w of a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. In some embodiments, both an oil and a fat may be included. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation include Tween® 60, Span® 80, cetostearyl alcohol, benzyl alcohol, myristyl alcohol, glyceryl monostearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils are used.

Pharmaceutical formulations herein comprise the active ingredient together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, solutions, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions may be in the form of a sterile injectable or intravenous preparations, such as a sterile injectable aqueous or oleaginous suspension. This suspension may be formulated according to the known art using those suitable dispersing or wetting agents and suspending agents which have been mentioned above. The sterile injectable or intravenous preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compound with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by inhalation through the nasal passage or by inhalation through the mouth. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of Pneumoviridae infections as described below.

Another embodiment provides a novel, efficacious, safe, nonirritating and physiologically compatible inhalable composition comprising the compound of Formula I, or a pharmaceutically acceptable salt thereof, suitable for treating Pneumoviridae infections and potentially associated bronchiolitis. Non-limiting exemplary pharmaceutically acceptable salts are inorganic acid salts including hydrochloride, hydrobromide, sulfate or phosphate salts as they may cause less pulmonary irritation. In some embodiments, the inhalable formulation is delivered to the endobronchial space in an aerosol comprising particles with a mass median aerodynamic diameter (MMAD) between about 1 and about 5 µm. In some embodiments, the compound of Formula I is formulated for aerosol delivery using a nebulizer, pressurized metered dose inhaler (pMDI), or dry powder inhaler (DPI).

Non-limiting examples of nebulizers include atomizing, jet, ultrasonic, pressurized, vibrating porous plate, or equivalent nebulizers including those nebulizers utilizing adaptive aerosol delivery technology (Denyer, *J Aerosol medicine Pulmonary Drug Delivery* 2010, 23 Supp 1, S1-S10). A jet nebulizer utilizes air pressure to break a liquid solution into aerosol droplets. An ultrasonic nebulizer works by a piezoelectric crystal that shears a liquid into small aerosol droplets. A pressurized nebulization system forces solution under pressure through small pores to generate aerosol droplets. A vibrating porous plate device utilizes rapid vibration to shear a stream of liquid into appropriate droplet sizes.

In some embodiments, the formulation for nebulization is delivered to the endobronchial space in an aerosol comprising particles with a MMAD predominantly between about 1 µm and about 5 µm using a nebulizer able to aerosolize the formulation of the compound of Formula I into particles of the required MMAD. To be optimally therapeutically effective and to avoid upper respiratory and systemic side effects, the majority of aerosolized particles should not have a MMAD greater than about 5 µm. If an aerosol contains a large number of particles with a MMAD larger than 5 µm, the particles are deposited in the upper airways decreasing the amount of drug delivered to the site of inflammation and bronchoconstriction in the lower respiratory tract. If the MMAD of the aerosol is smaller than about 1 µm, then the particles have a tendency to remain suspended in the inhaled air and are subsequently exhaled during expiration.

When formulated and delivered according to the method herein, the aerosol formulation for nebulization delivers a therapeutically efficacious dose of the compound of Formula I to the site of Pneumoviridae infection sufficient to treat the Pneumoviridae infection. The amount of drug administered must be adjusted to reflect the efficiency of the delivery of a therapeutically efficacious dose of the compound of Formula I. In some embodiments, a combination of the aqueous aerosol formulation with the atomizing, jet, pressurized, vibrating porous plate, or ultrasonic nebulizer permits, depending on the nebulizer, about, at least, 20, to about 90%, for example about 70% delivery of the administered dose of the compound of Formula I into the airways. In some embodiments, at least about 30 to about 50% of the active compound is delivered. In some embodiments, about 70 to about 90% of the active compound is delivered.

In another embodiment, the compound of Formula I or a pharmaceutically acceptable salt thereof, is delivered as a dry inhalable powder. The compound is administered endobronchially as a dry powder formulation to efficacious deliver fine particles of compound into the endobronchial space using dry powder or metered dose inhalers. For delivery by DPI, the compound of Formula I is processed into particles with, predominantly, MMAD between about 1 µm and about 5 µm by milling spray drying, critical fluid processing, or precipitation from solution. Media milling, jet milling and spray-drying devices and procedures capable of producing the particle sizes with a MMAD between about 1 µm and about 5 µm are well known in the art. In one embodiment, excipients are added to the compound of Formula I before processing into particles of the required sizes. In another embodiment, excipients are blended with the particles of the required size to aid in dispersion of the drug particles, for example by using lactose as an excipient.

Particle size determinations are made using devices well known in the art. For example a multi-stage Anderson cascade impactor or other suitable method such as those specifically cited within the US Pharmacopoeia Chapter 601 as characterizing devices for aerosols within metered-dose and dry powder inhalers.

In some embodiments, the compound of Formula I is delivered as a dry powder using a device such as a dry powder inhaler or other dry powder dispersion devices. Non-limiting examples of dry powder inhalers and devices include those disclosed in U.S. Pat. Nos. 5,458,135; 5,740,794; 5,775,320; 5,785,049; 3,906,950; 4,013,075; 4,069,819; 4,995,385; 5,522,385; 4,668,218; 4,667,668; 4,805,811 and 5,388,572. There are two major designs of dry powder inhalers. One design is a metering device in which a reservoir for the drug is place within the device and the patient adds a dose of the drug into the inhalation chamber. The second design is a factory-metered device in which each individual dose has been manufactured in a separate container. Both systems depend on the formulation of the drug into small particles of MMAD from 1 µm and about 5 µm and often involve co-formulation with larger excipient particles such as, but not limited to, lactose. Drug powder is placed in the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs. In some embodiments, the compound of Formula I, or a pharmaceutically acceptable salt thereof, is delivered as a dry powder using either type of dry powder inhaler as described herein, wherein the MMAD of the dry powder, exclusive of any excipients, is predominantly in the range of 1 µm to about 5 µm.

In another embodiment, the compound of Formula I is delivered as a dry powder using a metered dose inhaler.

Non-limiting examples of metered dose inhalers and devices include those disclosed in U.S. Pat. Nos. 5,261,538; 5,544, 647; 5,622,163; 4,955,371; 3,565,070; 3,361,306 and 6,116, 234. In some embodiments, the compound of Formula I, or a pharmaceutically acceptable salt thereof, is delivered as a dry powder using a metered dose inhaler wherein the MMAD of the dry powder, exclusive of any excipients, is predominantly in the range of about 1-5 µm.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Exemplary unit dosage formulations are those containing a daily dose or unit daily sub-dose, as herein above recited, or an appropriate fraction thereof, of the active ingredient.

It should be understood that in addition to the ingredients particularly mentioned above the formulations may include other agents conventional in the art having regard to the type of formulation in question, for example those suitable for oral administration may include flavoring agents.

Further provided are veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

In some embodiments, the compound of Formula I is formulated to provide controlled release pharmaceutical formulations ("controlled release formulations") in which the release of the compound of Formula I is controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day; for example, from about 0.01 to about 10 mg/kg body weight per day. In some embodiments, the effective dose is from about 0.01 to about 5 mg/kg body weight per day; for example typically, from about 0.05 to about 0.5 mg/kg body weight per day. For example, the daily candidate dose for an adult human of approximately 70 kg body weight will range from 1 mg to 1000 mg, for example between 5 mg and 500 mg, and may take the form of single or multiple doses.

V. ROUTES OF ADMINISTRATION

The compound of Formula I (also referred to herein as the active ingredient), can be administered by any appropriate route appropriate. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with for example the condition of the recipient.

The compound of the present disclosure may be administered to an individual in accordance with an effective dosing regimen for a desired period of time or duration, such as at least about one week, at least about two weeks, at least about three weeks, one month, at least about 2 months, at least about 3 months, at least about 6 months, or at least about 12 months or longer. In one variation, the compound is administered on a daily or intermittent schedule for the required duration, up to the individual's life.

The dosage or dosing frequency of the compound of the present disclosure may be adjusted over the course of the treatment, based on the judgment of the administering physician.

The compound may be administered to an individual (e.g., a human) in an effective amount. In some embodiments, the compound is administered once daily.

The compound can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 mg to about 30 mg per day, or such as from about 30 mg to about 300 mg per day.

The compound of the present disclosure may be combined with one or more additional therapeutic agents in any dosage amount of the compound of the present disclosure (e.g., from 1 mg to 1000 mg of compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose. Other therapeutically effective amounts of the compound of the present disclosure are about 100, 125, 150, 175, 200, 225, 250, 275, 300, 325, 350, 375, 400, 425, 450, 475, or about 500 mg per dose. Other therapeutically effective amounts of the compound of the present disclosure are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In some embodiments, a single dose can be administered once every week. A single dose can also be administered once every month.

Other therapeutically effective amounts of the compound of the present disclosure are about 20, 25, 30, 35, 40, 45, 50, 55, 60, 65, 70, 75, 80, 85, 90, 95, or about 100 mg per dose.

The frequency of dosage of the compound of the present disclosure are determined by the needs of the individual patient and can be, for example, once per day or twice, or more times, per day. Administration of the compound continues for as long as necessary to treat the viral infection. For example, the compound can be administered to a human being infected with a virus for a period of from 20 days to 180 days or, for example, for a period of from 20 days to 90 days or, for example, for a period of from 30 days to 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

In one embodiment, pharmaceutical compositions comprising the compound of the present disclosure, or a pharmaceutically acceptable salt thereof, in combination with one or more (e.g., one, two, three, four, one or two, one to three, or one to four) additional therapeutic agents, and a pharmaceutically acceptable excipient are provided.

In one embodiment, kits comprising the compound of the present disclosure, or a pharmaceutically acceptable salt thereof, in combination with one or more (e.g., one, two, three, four, one or two, one to three, or one to four) additional therapeutic agents are provided.

In some embodiments, the compound of the present disclosure, or a pharmaceutically acceptable salt thereof, is combined with one, two, three, four or more additional therapeutic agents. In some embodiments, the compound of the present disclosure, or a pharmaceutically acceptable salt thereof, is combined with two additional therapeutic agents. In other embodiments, the compound of the present disclosure, or a pharmaceutically acceptable salt thereof, is combined with three additional therapeutic agents. In further embodiments, the compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In some embodiments, when the compound of the present disclosure is combined with one or more additional therapeutic agents as described herein, the components of the composition are administered as a simultaneous or sequential regimen. When administered sequentially, the combination may be administered in two or more administrations.

In some embodiments, the compound of the present disclosure is combined with one or more additional therapeutic agents in a unitary dosage form for simultaneous administration to a patient, for example as a solid dosage form for oral administration.

In some embodiments, the compound of the present disclosure is co-administered with one or more additional therapeutic agents.

In order to prolong the effect of the compound of the present disclosure, it is often desirable to slow the absorption of a compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending a compound in an oil vehicle. Injectable depot forms are made by forming microencapsule matrices of a compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly (anhydrides). Depot injectable formulations are also prepared by entrapping a compound in liposomes or microemulsions that are compatible with body tissues.

VI. COMBINATION THERAPY

The compound of Formula I and compositions provided herein are also used in combination with other active therapeutic agents for the treatment of virus infections, such as Pneumoviridae, Picornaviridae, Flaviviridae, or Filoviridae virus infections.

Combination Therapy for the Treatment of Pneumoviridae

The compound and compositions provided herein are also used in combination with other active therapeutic agents. For the treatment of Pneumoviridae virus infections, preferably, the other active therapeutic agent is active against Pneumoviridae virus infections, particularly respiratory syncytial virus infections and/or metapneumovirus infections. Non-limiting examples of these other active therapeutic agents active against RSV are ribavirin, palivizumab, motavizumab, RSV-IGIV (RespiGam®), MEDI-557, A-60444 (also known as RSV604), MDT-637, BMS-433771, ALN-RSVO, ALX-0171 and mixtures thereof. Other non-limiting examples of other active therapeutic agents active against respiratory syncytial virus infections include respiratory syncytial virus protein F inhibitors, such as AK-0529; RV-521, ALX-0171, JNJ-53718678, BTA-585, and presatovir; RNA polymerase inhibitors, such as lumicitabine and ALS-8112; anti-RSV G protein antibodies, such as anti-G-protein mAb; viral replication inhibitors, such as nitazoxanide.

In some embodiments, the other active therapeutic agent may be a vaccine for the treatment or prevention of RSV, including but not limited to MVA-BN RSV, RSV-F, MEDI-8897, JNJ-64400141, DPX-RSV, SynGEM, GSK-3389245A, GSK-300389-1A, RSV-MEDI deltaM2-2 vaccine, VRC-RSVRGPO84-OOVP, Ad35-RSV-FA2, Ad26-RSV-FA2, and RSV fusion glycoprotein subunit vaccine.

Non-limiting examples of other active therapeutic agents active against metapneumovirus infections include sialidase modulators such as DAS-181; RNA polymerase inhibitors, such as ALS-8112; and antibodies for the treatment of Metapneumovirus infections, such as EV-046113.

In some embodiments, the other active therapeutic agent may be a vaccine for the treatment or prevention of metapneumovirus infections, including but not limited to mRNA-1653 and rHMPV-Pa vaccine.

Combination Therapy for the Treatment of Picornaviridae

The compound and compositions provided herein are also used in combination with other active therapeutic agents. For the treatment of Picornaviridae virus infections, preferably, the other active therapeutic agent is active against Picornaviridae virus infections, particularly Enterovirus infections. Non-limiting examples of these other active therapeutic agents are capsid binding inhibitors such as pleconaril, BTA-798 (vapendavir) and other compounds disclosed by Wu, et al. (U.S. Pat. No. 7,078,403) and Watson (U.S. Pat. No. 7,166,604); fusion sialidase protein such as DAS-181; a capsid protein VP1 inhibitor such as VVX-003 and AZN-001; a viral protease inhibitor such as CW-33; a phosphatidylinositol 4 kinase beta inhibitor such as GSK-480 and GSK-533; anti-EV71 antibody.

In some embodiments, the other active therapeutic agent may be a vaccine for the treatment or prevention of Picornaviridae virus infections, including but not limited to EV71 vaccines, TAK-021, and EV-D68 adenovector-based vaccine.

Combination Therapy for Respiratory Infections

Many of the infections of the Pneumoviridae and Picornaviridae viruses are respiratory infections. Therefore, additional active therapeutics used to treat respiratory symptoms and sequelae of infection may be used in combination with the compound of Formula I. The additional agents are preferably administered orally or by direct inhalation. For example, additional therapeutic agents in combination with the compound of Formula I for the treatment of viral respiratory infections include, but are not limited to, bronchodilators and corticosteroids.

Glucocorticoids

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compound of Formula I are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone, AZD-7594, ciclesonide; or a pharmaceutically acceptable salts thereof.

Anti-Inflammatory Agents

Other anti-inflammatory agents working through anti-inflammatory cascade mechanisms are also useful as additional therapeutic agents in combination with the compound of Formula I for the treatment of viral respiratory infections. Applying "anti-inflammatory signal transduction modulators" (referred to in this text as AIS™), like phosphodiesterase inhibitors (e.g., PDE-4, PDE-5, or PDE-7 specific), transcription factor inhibitors (e.g., blocking NFκB through TKK inhibition), or kinase inhibitors (e.g., blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluoro-phenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

β2-adrenoreceptor agonist bronchodilators

Combinations comprising inhaled β2-adrenoreceptor agonist bronchodilators such as formoterol, albuterol or salmeterol with the compound of Formula I are also suitable, but non-limiting, combinations useful for the treatment of respiratory viral infections.

Combinations of inhaled β2-adrenoreceptor agonist bronchodilators such as formoterol or salmeterol with ICS's are also used to treat both the bronchoconstriction and the inflammation (Symbicort® and Advair®, respectively). The combinations comprising these ICS and β2-adrenoreceptor agonist combinations along with the compound of Formula I are also suitable, but non-limiting, combinations useful for the treatment of respiratory viral infections.

Other examples of Beta 2 adrenoceptor agonists are bedoradrine, vilanterol, indacaterol, olodaterol, tulobuterol, formoterol, abediterol, salbutamol, arformoterol, levalbuterol, fenoterol, and TD-5471.

Anticholinergics

For the treatment or prophylaxis of pulmonary bronchoconstriction, anticholinergics are of potential use and, therefore, useful as an additional therapeutic agent in combination with the compound of Formula I for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2- carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo[3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester; revefenacin, glycopyrronium bromide, umeclidinium bromide, tiotropium bromide, aclidinium bromide, bencycloquidium bromide.

Mucolytic Agents

The compound of Formula I and the compositions provided herein may also be combined with mucolytic agents to treat both the infection and symptoms of respiratory infections. A non-limiting example of a mucolytic agent is ambroxol. Similarly, the compound of Formula I may be combined with expectorants to treat both the infection and symptoms of respiratory infections. A non-limiting example of an expectorant is guaifenesin.

Nebulized hypertonic saline is used to improve immediate and long-term clearance of small airways in patients with lung diseases (Kuzik, J. Pediatrics 2007, 266). Thus, the compound of Formula I may also be combined with nebulized hypertonic saline particularly when the Pneumoviridae virus infection is complicated with bronchiolitis. The combination of the compound of Formula I with hypertonic saline may also comprise any of the additional agents discussed above. In one embodiment, nebulized about 3% hypertonic saline is used.

Combination Therapy for the Treatment of COPD

The compound and compositions provided herein are also used in combination with other active therapeutic agents. For the treatment of respiratory exacerbations of COPD, the other active therapeutic agents include other active against COPD. Non-limiting examples of these other active therapeutic agents include anti-IL5 antibodies, such as benralizumab, mepolizumab; dipeptidyl peptidase I (DPP1) inhibitors, such as AZD-7986 (INS-1007); DNA gyrase inhibitor/topoisomerase IV inhibitors, such as ciprofloxacin hydrochloride; MDR associated protein 4/phosphodiesterase (PDE) 3 and 4 inhibitors, such as RPL-554; CFTR stimulators, such as ivacaftor, QBW-251; MMP-9/MMP-12 inhibitors, such as RBx-10017609' Adenosine A1 receptor antagonists, such as PBF-680; GATA 3 transcription factor inhibitors, such as SB-010; muscarinic receptor modulator/nicotinic acetylcholine receptor agonists, such as ASM-024; MARCKS protein inhibitors, such as BIO-11006; kit tyrosine kinase/PDGF inhibitors such as masitinib; phosphodiesterase (PDE) 4 inhibitors, such as roflumilast, CHF-6001; phosphoinositide-3 kinase delta inhibitors, such as nemiralisib; 5-Lipoxygenase inhibitors, such as TA-270; muscarinic receptor antagonist/beta 2 adrenoceptor agonist, such as batefenterol succinate, AZD-887, ipratropium bromide; TRN-157; elastase inhibitors, such as erdosteine; metalloprotease-12 inhibitors such as FP-025; interleukin 18 ligand inhibitors, such as tadekinig alfa; skeletal muscle troponin activators, such as CK-2127107; p38 MAP kinase inhibitors, such as acumapimod; IL-17 receptor modulators, such as CNTO-6785; CXCR2 chemokine antagonists, such as danirixin; leukocyte elastase inhibitors, such as POL-6014; epoxide hydrolase inhibitors, such as GSK-2256294; HNE inhibitors, such as CHF-6333; VIP agonists, such as aviptadil; phosphoinositide-3 kinase delta/gamma inhibitors, such as RV-1729; complement C3 inhibitors, such as APL-1; and G-protein coupled receptor-44 antagonists, such as AM-211.

Other non-limiting examples of active therapeutic agents also include budesonide, adipocell, nitric oxide, PUR-1800, YLP-001, LT-4001, azithromycin, gamunex, QBKPN, sodium pyruvate, MUL-1867, mannitol, MV-130, MEDI-3506, BI-443651, VR-096, OPK-0018, TEV-48107, doxofylline, TEV-46017, OligoG-COPD-5/20, Stempeucel®, ZP-051, lysine acetylsalicylate.

In some embodiments, the other active therapeutic agent may be a vaccine that is active against COPD, including but not limited to MV-130 and GSK-2838497A.

Combination Therapy for the Treatment of Dengue

The compound and compositions provided herein are also used in combination with other active therapeutic agents. For the treatment of Flaviviridae virus infections, preferably, the other active therapeutic agent is active against Flaviviridae virus infections, particularly dengue infections. Non-limiting examples of these other active therapeutic agents are host cell factor modulators, such as GBV-006; fenretinide ABX-220, BRM-211; alpha-glucosidase 1 inhibitors, such as celgosivir; platelet activating factor receptor (PAFR) antagonists, such as modipafant; cadherin-5/Factor Ia modulators, such as FX-06; NS4B inhibitors, such as JNJ-8359; viral RNA splicing modulators, such as ABX-202; a NS5 polymerase inhibitor; a NS3 protease inhibitor; and a TLR modulator.

In some embodiments, the other active therapeutic agent may be a vaccine for the treatment or prevention of dengue, including but not limited to TetraVax-DV, Dengvaxia®, DPIV-001, TAK-003, live attenuated dengue vaccine, tetravalent dengue fever vaccine, tetravalent DNA vaccine, rDEN2delta30-7169; and DENV-1 PIV.

Combination Therapy for the Treatment of Ebola

The compound and compositions provided herein are also used in combination with other active therapeutic agents. For the treatment of Filoviridae virus infections, preferably, the other active therapeutic agent is active against Filoviridae virus infections, particularly Marburg virus, Ebola virus and Cueva virus infections. Non-limiting examples of these other active therapeutic agents are: ribavirin, palivizumab, motavizumab, RSV-IGIV (RespiGam®), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), TKM-Ebola, T-705 monophosphate, T-705 diphosphate, T-705 triphosphate, FGI-106 (1-N,7-N-bis[3-

(dimethylamino)propyl]-3,9-dimethylquinolino[8,7-h]quinolone-1,7-diamine), rNAPc2, OS-2966, brincidofovir, remdesivir;

RNA polymerase inhibitors, such as galidesivir, favipiravir (also known as T-705 or Avigan), JK-05; host cell factor modulators, such as GMV-006; cadherin-5/factor Ia modulators, such as FX-06; and antibodies for the treatment of Ebola, such as REGN-3470-3471-3479 and ZMapp.

Other non-limiting active therapeutic agents active against Ebola include an alpha-glucosidase 1 inhibitor, a cathepsin B inhibitor, a CD29 antagonist, a dendritic ICAM-3 grabbing nonintegrin 1 inhibitor, an estrogen receptor antagonist, a factor VII antagonist HLA class II antigen modulator, a host cell factor modulator, a Interferon alpha ligand, a neutral alpha glucosidase AB inhibitor, a niemann-Pick C1 protein inhibitor, a nucleoprotein inhibitor, a polymerase cofactor VP35 inhibitor, a Serine protease inhibitor, a tissue factor inhibitor, a TLR-3 agonist, a viral envelope glycoprotein inhibitor, and an Ebola virus entry inhibitors (NPC1 inhibitors).

In some embodiments, the other active therapeutic agent may be a vaccine for the treatment or prevention of Ebola, including but not limited to VRC-EBOADC076-00-VP, adenovirus-based Ebola vaccine, rVSV-EBOV, rVSVN4CT1-EBOVGP, MVA-BN Filo+Ad26-ZEBOV regimen, INO-4212, VRC-EBODNA023-00-VP, VRC-EBOADC069-00-VP, GamEvac-combi vaccine, SRC VB Vector, HPIV3/EboGP vaccine, MVA-EBOZ, Ebola recombinant glycoprotein vaccine, Vaxart adenovirus vector 5-based Ebola vaccine, FiloVax vaccine, GOVX-E301, and GOVX-E302.

The compound and compositions provided herein may also be used in combination with phosphoramidate morpholino oligomers (PMOs), which are synthetic antisense oligonucleotide analogs designed to interfere with translational processes by forming base-pair duplexes with specific RNA sequences. Examples of PMOs include but are not limited to AVI-7287, AVI-7288, AVI-7537, AVI-7539, AVI-6002, and AVI-6003.

The compound and compositions provided herein are also intended for use with general care provided to patients with Filoviridae viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen), pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis.

VII. METHODS OF TREATING VIRAL INFECTIONS

The present disclosure provides methods for treating a variety of diseases, such as respiratory syncytial virus (RSV), HRV, hMPV, ebola, Zika, West Nile, Dengue, HCV and HBV using the compound of Formula I.

Pnuemoviridae

In some embodiments, the present disclosure provides methods for treating a Pneumoviridae infection, comprising administering to an individual (e.g., a human) infected with Pneumoviridae virus a therapeutically effective amount the compound of the present disclosure or a pharmaceutically acceptable salt thereof. Pneumoviridae viruses include, but are not limited to, respiratory syncytial virus (RSV) and other Pneumoviridae viruses.

In some embodiments, the present disclosure provides a method of treating a Pneumoviridae virus infection in a human in need thereof, the method comprising administering to the human a therapeutically effective amount of the compound of the present disclosure, or a pharmaceutically acceptable salt thereof. Pneumoviridae viruses include, but are not limited to, respiratory syncytial virus, and human metapneumovirus. In some embodiments, the Pneumoviridae virus infection is a respiratory syncytial virus infection. In some embodiments, the Pneumoviridae virus infection is human metapneumovirus infection.

In some embodiments, the present disclosure provides a method for manufacturing a medicament for treating a Pneumoviridae virus infection in a human in need thereof, characterized in that the compound of the present disclosure, or a pharmaceutically acceptable salt thereof, is used. In some embodiments, the present disclosure provides use of the compound of the present disclosure, or a pharmaceutically acceptable salt thereof, for the manufacture of a medicament for the treatment in a human of a Pneumoviridae virus infection. In some embodiments, the Pneumoviridae virus infection is a respiratory syncytial virus infection. In some embodiments, the Pneumoviridae virus infection is human metapneumovirus infection.

In some embodiments, the present disclosure provides the compound of the present disclosure, or a pharmaceutically acceptable salt thereof, for use in the treatment of a Pneumoviridae virus infection in a human in need thereof. In some embodiments, the Pneumoviridae virus infection is a respiratory syncytial virus infection. In some embodiments, the Pneumoviridae virus infection is human metapneumovirus infection.

In some embodiments, the present disclosure provides methods for treating a RSV infection, comprising administering to an individual (e.g., a human) infected with respiratory syncytial virus a therapeutically effective amount the compound of the present disclosure or a pharmaceutically acceptable salt thereof. Typically, the individual is suffering from a chronic respiratory syncytial viral infection, although it is within the scope of the present disclosure to treat people who are acutely infected with RSV.

In some embodiments, a method of inhibiting RSV replication is provided, comprising administering the compound of the present disclosure, or a pharmaceutically acceptable salt thereof, to an individual (e.g., a human).

In some embodiments, the present disclosure provides a method for reducing the viral load associated with RSV infection, wherein the method comprises administering to an individual (e.g., a human) infected with RSV a therapeutically effective amount of the compound of the present disclosure, or a pharmaceutically acceptable salt thereof, wherein the therapeutically effective amount is sufficient to reduce the RSV viral load in the individual.

As described more fully herein, the compound of the present disclosure can be administered with one or more additional therapeutic agent(s) to an individual (e.g., a human) infected with RSV. The additional therapeutic agent(s) can be administered to the infected individual (e.g., a human) at the same time as the compound of the present disclosure or before or after administration of the compound of the present disclosure.

In some embodiments, the compound of the present disclosure, or a pharmaceutically acceptable salt thereof, for use in treating or preventing a RSV infection is provided. In some embodiments, the compound of the present disclosure, or a pharmaceutically acceptable salt thereof, for the manufacture of a medicament for treating or preventing a RSV infection is provided.

As described more fully herein, the compound of the present disclosure can be administered with one or more additional therapeutic agent(s) to an individual (e.g., a human) infected with RSV. Further, in some embodiments, when used to treat or prevent RSV, the compound of the present disclosure may be administered with one or more (e.g., one, two, three, four or more) additional therapeutic agent(s) selected from the group consisting of RSV combination drugs, RSV vaccines, RSV DNA polymerase inhibitors, immunomodulators toll-like receptor (TLR) modulators, interferon alpha receptor ligands, hyaluronidase inhibitors, respiratory syncytial surface antigen inhibitors, cytotoxic T-lymphocyte-associated protein 4 (ipi4) inhibitors, cyclophilin inhibitors, RSV viral entry inhibitors, antisense oligonucleotide targeting viral mRNA, short interfering RNAs (siRNA) and ddRNAi endonuclease modulators, ribonucelotide reductase inhibitors, RSV E antigen inhibitors, covalently closed circular DNA (cccDNA) inhibitors, farnesoid X receptor agonists, RSV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, RSV replication inhibitors, arginase inhibitors, and other RSV drugs.

Picornaviridae

In some embodiments, the present disclosure provides a method of treating a Picornaviridae virus infection in a human in need thereof, the method comprising administering to the human a therapeutically effective amount of the compound of the present disclosure, or a pharmaceutically acceptable salt thereof. Picornaviridae viruses are eneteroviruses causing a heterogeneous group of infections including herpangina, aseptic meningitis, a common-cold-like syndrome (human rhinovirus infection), a non-paralytic poliomyelitis-like syndrome, epidemic pleurodynia (an acute, febrile, infectious disease generally occurring in epidemics), hand-foot-mouth syndrome, pediatric and adult pancreatitis and serious myocarditis. In some embodiments, the Picornaviridae virus infection is human rhinovirus infection.

In some embodiments, the present disclosure provides a method for manufacturing a medicament for treating a Picornaviridae virus infection in a human in need thereof, characterized in that the compound of the present disclosure, or a pharmaceutically acceptable salt thereof, is used. In some embodiments, the present disclosure provides use of the compound of the present disclosure, or a pharmaceutically acceptable salt thereof, for the manufacture of a medicament for the treatment in a human of a Picornaviridae virus infection. In some embodiments, the Picornaviridae virus infection is human rhinovirus infection.

In some embodiments, the present disclosure provides the compound of the present disclosure, or a pharmaceutically acceptable salt thereof, for use in the treatment of a Picornaviridae virus infection in a human in need thereof. In some embodiments, the Picornaviridae virus infection is human rhinovirus infection.

Flaviviridae

In some embodiments, the present disclosure provides a method of treating a Flaviviridae virus infection in a human in need thereof, the method comprising administering to the human a therapeutically effective amount of the compound of the present disclosure, or a pharmaceutically acceptable salt thereof. Representative Flaviviridae viruses include, but are not limited to, dengue, Yellow fever, West Nile, Zika, Japanese encephalitis virus, Hepatitis C (HCV), and Hepatitis B (HBV). In some embodiments, the Flaviviridae virus infection is a dengue virus infection. In some embodiments, the Flaviviridae virus infection is a Yellow fever virus infection. In some embodiments, the Flaviviridae virus infection is a West Nile virus infection. In some embodiments, the Flaviviridae virus infection is a Zika virus infection. In some embodiments, the Flaviviridae virus infection is a Japanese ensephalitis virus infection. In some embodiments, the Flaviviridae virus infection is a Hepatitis C virus infection. In some embodiments, the Flaviviridae virus infection is a Hepatitis B virus infection.

In some embodiments, the present disclosure provides a method for manufacturing a medicament for treating a Flaviviridae virus infection in a human in need thereof, characterized in that the compound of the present disclosure, or a pharmaceutically acceptable salt thereof, is used. In some embodiments, the present disclosure provides use of the compound of the present disclosure, or a pharmaceutically acceptable salt thereof, for the manufacture of a medicament for the treatment in a human of a Flaviviridae virus infection. In some embodiments, the Flaviviridae virus infection is a dengue virus infection. In some embodiments, the Flaviviridae virus infection is a Yellow fever virus infection. In some embodiments, the Flaviviridae virus infection is a West Nile virus infection. In some embodiments, the Flaviviridae virus infection is a Zika virus infection. In some embodiments, the Flaviviridae virus infection is a Hepatitis C virus infection. In some embodiments, the Flaviviridae virus infection is a Hepatitis B virus infection.

In some embodiments, the present disclosure provides the compound of the present disclosure, or a pharmaceutically acceptable salt thereof, for use in the treatment of a Flaviviridae virus infection in a human in need thereof. In some embodiments, the Flaviviridae virus infection is a dengue virus infection. In some embodiments, the Flaviviridae virus infection is a Yellow fever virus infection. In some embodiments, the Flaviviridae virus infection is a West Nile virus infection. In some embodiments, the Flaviviridae virus infection is a Zika virus infection. In some embodiments, the Flaviviridae virus infection is a Hepatitis C virus infection. In some embodiments, the Flaviviridae virus infection is a Hepatitis B virus infection.

Filoviridae

In some embodiments, the present disclosure provides a method of treating a Filoviridae virus infection in a human in need thereof, the method comprising administering to the human a therapeutically effective amount of the compound of the present disclosure, or a pharmaceutically acceptable salt thereof. Representative Filoviridae viruses include, but are not limited to, ebola and Marburg. In some embodiments, the Filoviridae virus infection is an ebola virus infection.

In some embodiments, the present disclosure provides a method for manufacturing a medicament for treating a Filoviridae virus infection in a human in need thereof, characterized in that the compound of the present disclosure, or a pharmaceutically acceptable salt thereof, is used. In some embodiments, the present disclosure provides use of the compound of the present disclosure, or a pharmaceutically acceptable salt thereof, for the manufacture of a medicament for the treatment in a human of a Filoviridae virus infection. In some embodiments, the Filoviridae virus infection is an ebola virus infection.

In some embodiments, the present disclosure provides the compound of the present disclosure, or a pharmaceutically acceptable salt thereof, for use in the treatment of a Filoviridae virus infection in a human in need thereof. In some embodiments, the Filoviridae virus infection is an ebola virus infection.

VIII. METHODS OF TREATMENT OR PROPHYLAXIS OF AN EXACERBATION OF A RESPIRATORY CONDITION BY A VIRUS INFECTION

The compound of Formula I may also be used for the treatment or prophylaxis of an exacerbation of a respiratory condition by a viral infection in a human in need thereof.

In some embodiments, the present disclosure provides a method for the treatment or prophylaxis of an exacerbation of a respiratory condition by a viral infection in a human in need thereof, the method comprising administering to the human a therapeutically effective amount of the compound of the present disclosure, or a pharmaceutically acceptable salt thereof, wherein the respiratory condition is chronic obstructive pulmonary disease. In some embodiments, the viral infection is caused by respiratory syncytial virus, rhinovirus or metapneumovirus.

In some embodiments, the present disclosure provides a method for the treatment or prophylaxis of an exacerbation of a respiratory condition by a viral infection in a human in need thereof, the method comprising administering to the human a therapeutically effective amount of the compound of the present disclosure, or a pharmaceutically acceptable salt thereof, wherein the respiratory condition is asthma. In some embodiments, the viral infection is caused by respiratory syncytial virus, rhinovirus, enteroviruses or metapneumovirus.

In some embodiments, the present disclosure provides a method for manufacturing a medicament for the treatment or prophylaxis of an exacerbation of a respiratory condition by a viral infection in a human in need thereof, characterized in that the compound of the present disclosure, or a pharmaceutically acceptable salt thereof, is used, wherein the respiratory condition is chronic obstructive pulmonary disease. In some embodiments, the viral infection is caused by respiratory syncytial virus, rhinovirus or metapneumovirus.

In some embodiments, the present disclosure provides a method for manufacturing a medicament for the treatment or prophylaxis of an exacerbation of a respiratory condition by a viral infection in a human in need thereof, characterized in that the compound of the present disclosure, or a pharmaceutically acceptable salt thereof, is used, wherein the respiratory condition is asthma. In some embodiments, the viral infection is caused by respiratory syncytial virus, rhinovirus, enteroviruses or metapneumovirus.

In some embodiments, the present disclosure provides use of the compound of the present disclosure, or a pharmaceutically acceptable salt thereof, for the manufacture of a medicament for the treatment or prophylaxis in a human of an exacerbation of a respiratory condition by a viral infection, wherein the respiratory condition is chronic obstructive pulmonary disease. In some embodiments, the viral infection is caused by respiratory syncytial virus, rhinovirus or metapneumovirus.

In some embodiments, the present disclosure provides use of the compound of the present disclosure, or a pharmaceutically acceptable salt thereof, for the manufacture of a medicament for the treatment or prophylaxis in a human of an exacerbation of a respiratory condition by a viral infection, wherein the respiratory condition is asthma. In some embodiments, the viral infection is caused by respiratory syncytial virus, rhinovirus, enteroviruses or metapneumovirus.

In some embodiments, the present disclosure provides the compound of the present disclosure, or a pharmaceutically acceptable salt thereof, for use in the treatment or prophylaxis of an exacerbation of a respiratory condition by a viral infection in a human in need thereof, wherein the respiratory condition is chronic obstructive pulmonary disease. In some embodiments, the viral infection is caused by respiratory syncytial virus, rhinovirus or metapneumovirus.

In some embodiments, the present disclosure provides the compound of the present disclosure, or a pharmaceutically acceptable salt thereof, for use in the treatment or prophylaxis of an exacerbation of a respiratory condition by a viral infection in a human in need thereof, wherein the respiratory condition is asthma. In some embodiments, the viral infection is caused by respiratory syncytial virus, rhinovirus, enteroviruses or metapneumovirus.

IX. EXAMPLES

Abbreviations

Certain abbreviations and acronyms are used in describing the experimental details.

Although most of these would be understood by one skilled in the art, the Table below contains a list of many of these abbreviations and acronyms.

TABLE 1

List of abbreviations and acronyms.

| Abbreviation | Meaning |
| --- | --- |
| Ac | acetate |
| ACN | acetonitrile |
| DMSO | dimethylsulfoxide |
| DMF | dimethylformamide |
| Et | ethyl |
| EtOAc | ethylacetate |
| HPLC | high performance liquid chromatography |
| LC | liquid chromatography |
| MCPBA | meta-chloroperbenzoic acid |
| Me | methyl |
| m/z | mass to charge ratio |
| MS or ms | mass spectrum |
| Ph | phenyl |
| RT | room temperature |
| TBAF | tetrabutylammonium fluoride |
| TFA | trifluoroacetic acid |
| THF | tetrahydrofuran |
| TMSCl | trimethylsilyl chloride |
| $t_R$ | retention time |
| δ | parts per million referenced to residual non-deuterated solvent peak |

Compounds and intermediates can be subjected to preparatory HPLC (Phenomenex Gemini 10u C18 110 Å AXIA 250×21.2 mm column, 30-70% acetonitrile/water gradient with 0.1% TFA). Some compounds are afforded as the TFA salt following this preparatory HPLC process.

A. Intermediates

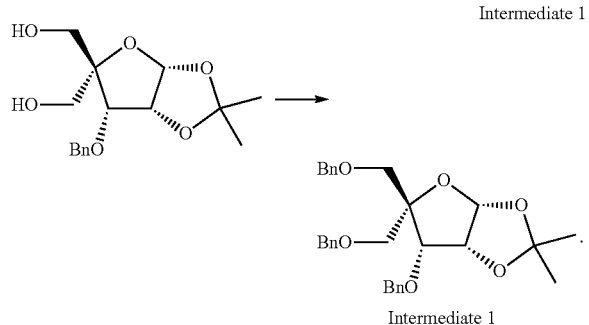

Intermediate 1

To Reactor 1 charge 3-O-benzyl-4-(hydroxymethyl)-1,2-O-isopropylidene-α-D-ribofuranose (125 g, 402 mmol, 1.0 eq). Charge THF (625 mL, 5 Vol) followed by benzyl bromide (106 mL, 2.2 eq). Set jacket to 0° C. Charge NaHMDS (40 wt % in THF, 450 mL, 2.2 eq) in a manner keeping $T_{int}$<10° C. After addition is complete, set jacket to 15° C. and agitate for 60 min. The reaction is monitored by TLC 20% ethyl acetate in 80% hexanes and staining with ceric ammonium molybdate (CAM). Set jacket to 5° C. Dissolve acetic acid (70 mL, 2.5 eq) in water (1 L, 8 Vol). Charge the aqueous solution to the reaction in a manner keeping $T_{int}$<15° C. and allow the phases to separate. Discharge the lower aqueous layer to Reactor 2. Concentrate Reactor 1 contents by ~50%. Charge MTBE (1.25 L, 10 Vol) to Reactor 2. Agitate for 15 min and allow the layers to separate. Discharge the lower aqueous layer and discard. Charge Reactor 2 contents to Reactor 1. Charge 14% brine solution (1 L, 8 vol) to Reactor 1. Agitate for 15 min and discharge the lower aqueous layer. Concentrate the organics by ~50%. Coevaporate the contents with methanol (3×8 Vol). Concentrate the intermediate 1 to ~4 Vol and use as is for the next step.

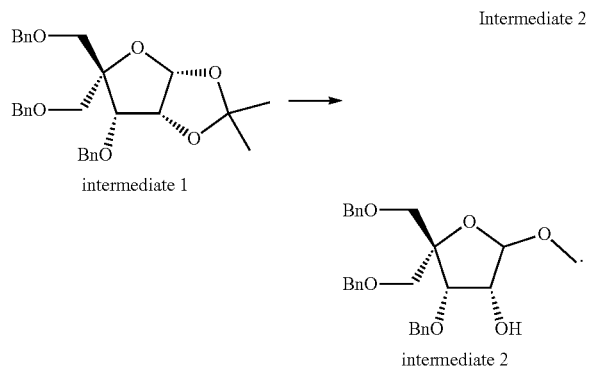

Intermediate 2

To Reactor 1 containing crude intermediate 1 (197 g, 402 mmol, 1 eq), charge methanol (1 L, 5 Vol), 4 M HCl in dioxane (120 mL, 1.2 eq), and conc. sulfuric acid (1.1 mL, 0.05 eq). Agitate at ambient temperature for 2 h. Monitor the reaction by TLC 30% ethyl acetate 70% hexanes and CAM stain. Slowly charge 5 M KOH solution to pH >7 (100 mL, 1.25 eq). Concentrate the reaction mixture to ~2 Vol. Charge ethyl acetate (1 L, 5 Vol). Charge water (1 L, 5 Vol). Agitate for 15 min. Discharge the lower aqueous layer into Reactor 2. Charge ethyl acetate (1 L, 5 Vol) to Reactor 2 and agitate for 15 min. Discharge the lower aqueous layer and discard. Charge remaining Reactor 2 contents to Reactor 1. Concentrate Reactor 1 contents to 3 Vol. Charge MTBE (400 mL, 2 Vol) to Reactor 1. Charge sodium sulfate (400 g, 2 S) and agitate for 15 min. Filter off the solids and wash cake with MTBE (200 mL, 1 Vol). Charge organics to Reactor 1. Concentrate to ~3 Vol. Charge THF (400 mL, 2 Vol) and concentrate to ~3 Vol. Charge THF (400 mL, 2 Vol) and concentrate to ~3 Vol to afford intermediate 2. $R_f$~0.1 and 0.4 in 30% ethyl acetate 70% hexanes.

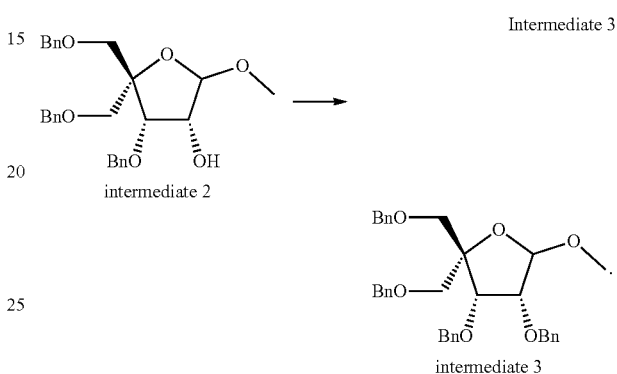

Intermediate 3

To Reactor 1 containing crude intermediate 2 (186 g, 402 mmol) charge THF (1 L, 5 Vol) and benzyl bromide (60 mL, 1.25 eq). Set jacket to 5° C. Charge NaHMDS 40 wt % (245 mL, 1.25 eq) in a manner keeping $T_{int}$<20° C. Set jacket to 15° C. and agitate for 60 min. Monitor reaction progress by TLC 30% ethyl acetate 70% hexanes and CAM stain. Set jacket to 0° C. Take up acetic acid (46 mL, 2 eq) in water (1 L, 5 Vol). Charge the aqueous solution to Reactor 1 in a manner keeping $T_{int}$<15° C. Set jacket to 15° C. and agitate for 15 min. Allow the phases to separate and discharge the lower aqueous layer into Reactor 2. Charge MTBE (1 L, 5 Vol) to Reactor 2 and agitate for 15 min. Concentrate Reactor 1 by ~50%. Allow the phases to separate in reactor 2 and discharge the lower aqueous layer and discard. Charge the Reactor 2 contents into Reactor 1. Charge 14% brine solution (1 L, 5 Vol). Agitate for 15 min. Discharge the lower aqueous layer and discard. Concentrate crude intermediate 3 $R_f$~0.8 in 30% ethyl acetate 70% hexanes to ~1 Vol and use as is for the next step.

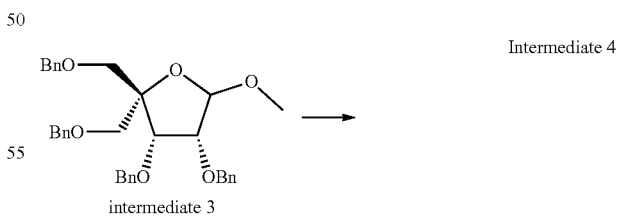

Intermediate 4

To Reactor 1 containing intermediate 3 (222 g, 401 mmol) with the jacket set to 20° C., charge water (222 mL, 1 Vol).

Charge TFA (667 mL, 3 Vol) in a manner keeping $T_{int}$<30° C. Agitate at 20° C. for 24 h. Monitor by TLC 30% ethyl acetate 70% hexanes with CAM stain. Concentrate Reactor 1 contents to ~2 Vol (550 mL solvent removed). Charge MTBE (1.5 L, 7 Vol). Set jacket to 10° C. Charge 5 M NaOH to pH >6 (600 mL, 7.5 Vol) in a manner keeping $T_{Int}$<25° C. Charge 5 wt % NaHCO$_3$ (1.1 L, 5 Vol) in a manner that minimizes outgassing. Agitate for 15 min. Discharge the lower aqueous layer and discard. Charge 14% brine solution (1.1 L, 5 Vol). Agitate for 15 min. Discharge the lower aqueous layer and discard. Concentrate the MTBE layer to ~4.5 Vol and use as is for the next step. Intermediate 4 $R_f$ ~ 0.5 in 30% ethyl acetate 70% hexanes.

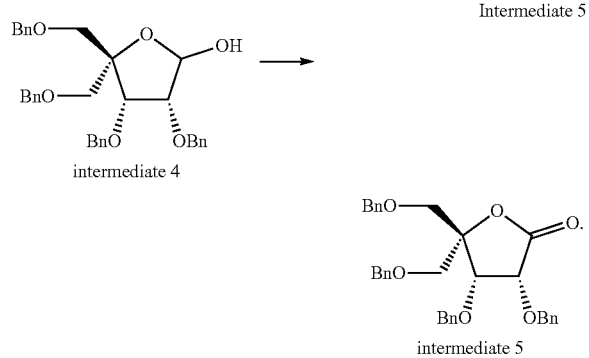

intermediate 4 intermediate 5

To Reactor 1 set at ~5° C. containing crude intermediate 4 (216 g, 401 mmol) in MTBE 4.5 Vol, charge TEMPO (0.6 g, 0.01 eq) and KBr (4.53 g, 0.1 eq). Dissolve K$_2$THPO$_4$*3 H$_2$O (87 g, 1 eq) in water (1.5 Vol). Charge to the reactor. Charge 8.25% bleach solution (425 mL, 1.35 eq) in a manner keeping $T_{int}$<10° C. (~50 min). Set the jacket to 5° C. and agitate for 1h. Monitor the reaction by TLC 30% ethyl acetate 70% hexanes with CAM stain. Dissolve sodium thiosulfate (30 g, 0.5 eq) in water (310 mL, 1.5 vol). Charge to Reactor 1 in a manner keeping $T_{Int}$<15° C. Set jacket to 15° C. Agitate for 15 min. Test for consumption of bleach using KI strips. Discharge the lower aq layer and discard. Charge 1S sodium sulfate and agitate for 15 min. Filter off the solids and wash cake with MTBE 1 Vol. Concentrate to an oil and purify by silica gel chromatography using 25 S silica 0-50% ethyl acetate in hexanes over 45 min to afford 3R,4S)-3,4-bis(benzyloxy)-5,5-bis((benzyloxy)methyl)dihydrofuran-2(3H)-one (intermediate 5). $^1$H NMR (400 MHz, DMSO-d$_6$) δ 7.40-7.24 (m, 18H), 7.24-7.19 (m, 2H), 4.87-4.74 (m, 2H), 4.74-4.68 (m, 2H), 4.61-4.39 (m, 6H), 3.83-3.66 (m, 4H).

Intermediate 6

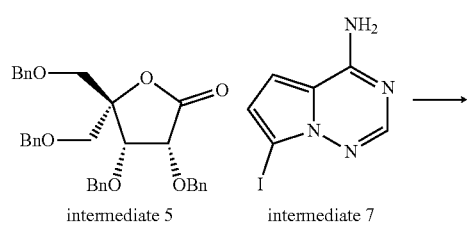

intermediate 5       intermediate 7

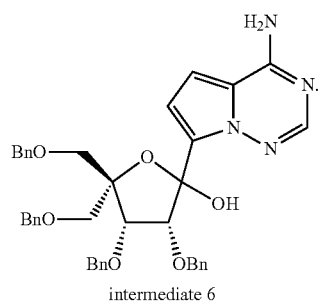

intermediate 6

To Reactor 1 intermediate 7 (50.83 g, 195.5 mmol, 1.11 eq) followed by THF (5 Vol). Set Reactor 1 jacket to 0° C. To Reactor 2 charge intermediate 5 (94.84 g, 176.1 mmol, 1.0 eq), THF (5 Vol), and 0.6 M LaCl$_3$*2LiCl in THF (290 mL, 170 mmol, 1 eq). Agitate Reactor 2 at ambient temperature for 30 min. To Reactor 1, charge TMS-Cl (25.1 mL, 197.2 mmol, 1.12 eq) in a manner keeping $T_{int}$<5° C. Agitate for 15 min. Set Reactor 1 jacket to −10° C., charge 2.0 M PhMgCl in THF (185 mL, 370 mmol, 2.1 eq) in a manner keeping $T_{int}$<0° C. Agitate for 15 min. Set Reactors 1 and 2 jackets to −20° C. To Reactor 1 charge 2.0 M iPrMgCl in THF (100 mL, 199 mmol, 1.13 eq) in a manner keeping $T_{int}$<−15° C. Agitate at −15° C. for 15 min. Transfer the contents of Reactor 1 into Reactor 2 in a manner keeping $T_{int}$<−15° C. Agitate at −15° C. for 60 min. Charge acetic acid (66 mL, 1145 mmol, 6.5 eq) in water (5 Vol) to Reactor 2 in a manner keeping $T_{int}$<20° C. Set Reactor 2 jacket to 20° C. Agitate for 15 min. Separate the layers. To Reactor 2 charge isopropyl acetate (4 Vol) and water (3 Vol). Agitate for 5 min. Separate the layers and wash the organics with 0.5 M HCl (2 Vol). Separate the layers and wash the organics with 2×5 Vol of 10 wt % KHCO$_3$(aq). Wash the organics with 14% brine solution (5 Vol). Separate the layers and dry the organics over sodium sulfate. Filter off the solids and concentrate the liquor to afford intermediate 6 which is telescoped into the next step.

UPLC/MS $t_R$=3.759 and 3.825 min, MS m/z=673.33 [M+1];

UPLC/MS system: Waters Acquity H Class

Column: Waters Acquity BEH 1.7 μM C18 2.1×50 mm

Solvents: Acetonitrile with 0.1% formic acid, Water with 0.1% formic acid

Gradient: 2% ACN 0-0.5 min. 2% ACN-98% ACN 0.5 min-3.0 min. 98% ACN 3 min-4 min. 98% ACN-2% ACN 4 min to 4.5 min. 2% ACN 4.5 min-5 min.

Flow: 0.5 mL/min Mass Range: 100-1200

Alternative synthesis of intermediate 6.

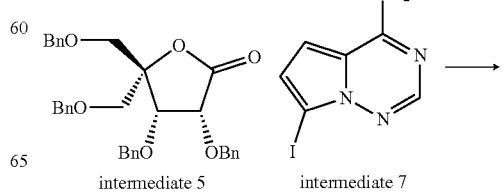

intermediate 5       intermediate 7

-continued

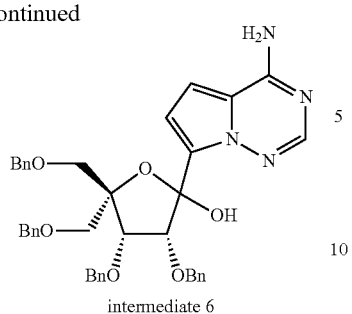

intermediate 6

To Reactor 1 intermediate 7 (5.90 g, 22.7 mmol, 1.11 eq) followed by THF (5 Vol). Set Reactor 1 jacket to 0° C. To Reactor 2 charge anhydrous NdCl$_3$ (5.1 g, 20.4 mmol, 1 eq), TBACl (6.1 g, 22.1 mmol, 1.08 eq) and THF (10 Vol). Set Reactor 2 jacket to 90° C. Distill off 50% of the THF to azeotropically dry the contents. Charge intermediate 5 (11 g, 20.4 mmol, 1.0 eq) to Reactor 2 and agitate at ambient temperature for 30 min. To Reactor 1, charge TMS-Cl (2.9 mL, 22.9 mmol, 1.12 eq) in a manner keeping $T_{int}$<5° C. Agitate for 15 min. Set Reactor 1 jacket to −10° C., charge 2.0 M PhMgCl in THF (22.2 mL, 44.3 mmol, 2.1 eq) in a manner keeping $T_{int}$<0° C. Agitate for 15 min. Set Reactors 1 and 2 jackets to −20° C. To Reactor 1 charge 2.0 M iPrMgCl in THF (11.5 mL, 199 mmol, 1.13 eq) in a manner keeping $T_{int}$<−15° C. Agitate at −15° C. for 15 min. Transfer the contents of Reactor 1 into Reactor 2 in a manner keeping $T_{int}$<−15° C. Agitate at −15° C. for 60 min. Charge acetic acid (66 mL, 1145 mmol, 6.5 eq) in water (5 Vol) to Reactor 2 in a manner keeping $T_{int}$<20° C. Set Reactor 2 jacket to 20° C. Agitate for 15 min. Separate the layers. To Reactor 2 charge isopropyl acetate (4 Vol) and water (3 Vol). Agitate for 5 min. Separate the layers and wash the organics with 0.5 M HCl (2 Vol). Separate the layers and wash the organics with 2×5 Vol of 10 wt % KHCO$_{3(aq)}$. Wash the organics with 14% brine solution (5 Vol). Separate the layers and dry the organics over sodium sulfate. Filter off the solids and concentrate the liquor to afford intermediate 6 which is telescoped into the next step.

UPLC/MS $t_R$=3.759 and 3.825 min, MS m/z=673.33 [M+1]

UPLC/MS system: Waters Acquity H Class

Column: Waters Acquity BEH 1.7 µM C18 2.1×50 mm

Solvents: Acetonitrile with 0.1% formic acid, Water with 0.1% formic acid

Gradient: 2% ACN 0-0.5 min. 2% ACN-98% ACN 0.5 min-3.0 min. 98% ACN 3 min-4 min. 98% ACN-2% ACN 4 min to 4.5 min. 2% ACN 4.5 min-5 min.

Flow: 0.5 mL/min

Mass Range: 100-1200

-continued

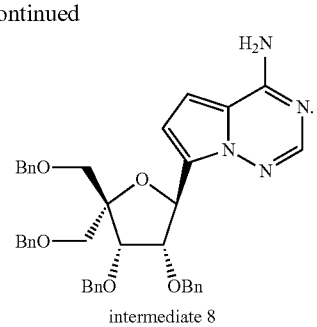

intermediate 8

To a reactor charge intermediate 6 (~118 g, 176 mmol) in DCM (10 Vol). Set jacket to −20° C. Charge triethylsilane (73 mL, 456 mmol, 2.6 eq). Charge boron trifluoride 46.5 mass % in diethyl ether (72 mL, 263.1 mmol, 1.5 eq) in a manner keeping $T_{int}$<−15° C. Agitate for 30 min. Set jacket to 0° C. Charge 5 M NaOH (175 mL, 877 mmol, 5 eq) in a manner keeping $T_{int}$<20° C. Set jacket to 20° C. Charge water (10 Vol). Separate the layers. Concentrate the organics layer. Back extract the aqueous layer with ethyl acetate (2×5 Vol). Combine the organics and wash with 14% brine (8 Vol). Dry the organics over sodium sulfate, filter and concentrate. Intermediate 8 is isolated by silica gel chromatography 50-100% ethyl acetate in hexanes. $^1$H NMR (400 MHz, DMSO-d$_6$) δ 7.83 (s, 1H), 7.71 (brs, 2H), 7.37-7.14 (m, 20H), 6.83 (d, J=4.5 Hz, 1H), 6.61 (d, J=4.4 Hz, 1H), 5.47 (d, J=7.0 Hz, 1H), 4.68 (d, J=11.6 Hz, 1H), 4.61-4.43 (m, 8H), 4.34 (d, J=4.8 Hz, 1H), 3.81-3.64 (m, 3H), 3.62 (d, J=10.0 Hz, 1H).

UPLC/MS $t_R$=3.919 min, MS m/z=657.32 [M+1]

UPLC/MS system: Waters Acquity H Class

Column: Waters Acquity BEH 1.7 µM C18 2.1×50 mm

Solvents: Acetonitrile with 0.1% formic acid, Water with 0.1% formic acid

Gradient: 2% ACN 0-0.5 min. 2% ACN-98% ACN 0.5 min-3.0 min. 98% ACN 3 min-4 min. 98% ACN-2% ACN 4 min to 4.5 min. 2% ACN 4.5 min-5 min.

Flow: 0.5 mL/min

Mass Range: 100-1200

Intermediate 8

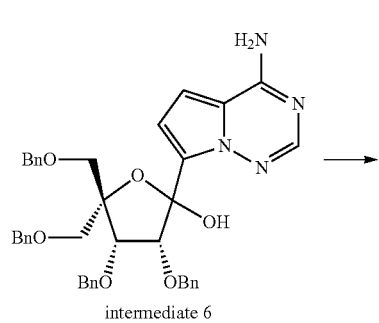

intermediate 6

Intermediate 9

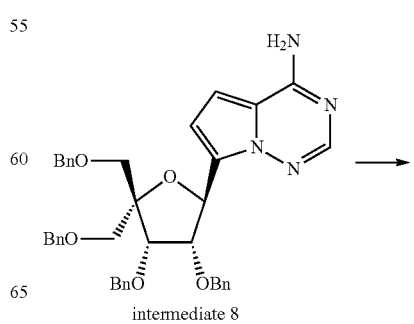

intermediate 8

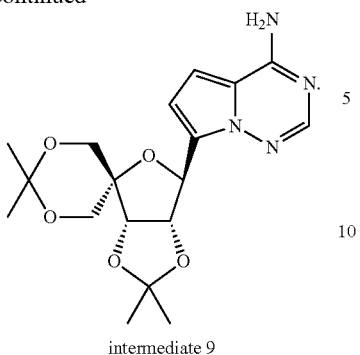

intermediate 9

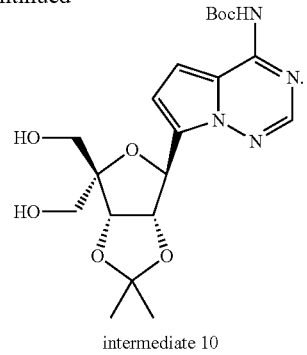

intermediate 10

To a nitrogen purged round bottom flask charge intermediate 8 (21.7 g, 33 mmol, 1 eq). Charge THF (3 Vol), 2,2-dimethoxypropane (3 Vol), and pTsOH (6.6 g, 34.6 mmol, 1.05 eq). Cool in a dry ice bath. Charge 10% Pd/C. Evacuate and backfill with hydrogen 3 times. Agitate at ambient temperature and pressure. Quench with sat NaHCO$_3$ (aq) to pH >7. Filter off the catalyst and wash the cake with methanol (2.5 Vol). Partition between ethyl acetate (10 Vol) and brine (10 Vol). Separate the layers and dry the organics over sodium sulfate. Filter of the solids and concentrate to afford Intermediate 9 that is telescoped into the next step.

UPLC/MS $t_R$=2.580 min, MS m/z=477.14 [M+1]

UPLC/MS system: Waters Acquity H Class

Column: Waters Acquity BEH 1.7 μM C18 2.1×50 mm

Solvents: Acetonitrile with 0.1% formic acid, Water with 0.1% formic acid

Gradient: 2% ACN 0-0.5 min. 2% ACN-98% ACN 0.5 min-3.0 min. 98% ACN 3 min-4 min. 98% ACN-2% ACN 4 min to 4.5 min. 2% ACN 4.5 min-5 min.

Flow: 0.5 mL/min

Mass Range: 100-1200

To a round bottom flask charge intermediate 9 (12.3 g, 32.7 mmol, 1 eq), THF (10 Vol), and di-tert-butyl-dicarbonate (14.4 g, 65.4 mmol, 2.0 eq). Charge DMAP (10.1 g, 81.7 mmol, 2.5 eq) portion-wise to minimize outgassing and exotherm. Agitate for 60 min to generate a mixture of mono and bis-Boc. Concentrate the reaction by ~50%. Charge MTBE (10 vol) and 2.0 M HCl (3.5 Vol). Separate the layers. Back extract aq with ethyl acetate (10 Vol). Combine the organics and wash with sat NaHCO$_3$(aq). Concentrate the organics. Charge methanol (10 Vol) to the crude mixture followed by KOH(s) (3.67 g, 2.0 eq). Agitate until Bis-Boc converted to mono-Boc. Concentrate the reaction. Partition with ethyl acetate (10 Vol) and water (10 Vol). Separate the layers and concentrate. Charge methanol (8 Vol) to the crude followed by pTsOH (6.5 g, 34.2 mmol, 1.05 eq). Agitate at ambient temperature. Quench with 5.25% NaHCO$_3$(aq) (80 mL, 52 mmol, 1.5 eq). Concentrate by ~25% and agitate overnight. Filter off the solids and wash the cake with MTBE (8 Vol). Dry in a vacuum oven to afford intermediate 10. $^1$H NMR (400 MHz, DMSO-d$_6$) δ 10.45 (s, 1H), 8.20 (s, 1H), 7.19 (d, J=4.3 Hz, 1H), 6.95 (d, J=4.7 Hz, 1H), 5.35 (d, J=5.2 Hz, 1H), 5.06 (t, J=5.7 Hz, 1H), 4.79-4.74 (m, 2H), 4.45 (t, J=5.8 Hz, 1H), 3.73-3.46 (m, 3H), 3.40-3.30 (m, 1H), 1.50 (s, 12H), 1.27 (s, 3H).

UPLC/MS $t_R$=2.767 min, MS m/z=437.17 [M+1]

UPLC/MS system: Waters Acquity H Class

Column: Waters Acquity BEH 1.7 μM C18 2.1×50 mm

Solvents: Acetonitrile with 0.1% formic acid, Water with 0.1% formic acid

Gradient: 2% ACN 0-0.5 min. 2% ACN-98% ACN 0.5 min-3.0 min. 98% ACN 3 min-4 min. 98% ACN-2% ACN 4 min to 4.5 min. 2% ACN 4.5 min-5 min.

Flow: 0.5 mL/min

Mass Range: 100-1200

Intermediate 11. (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol Intermediate 10

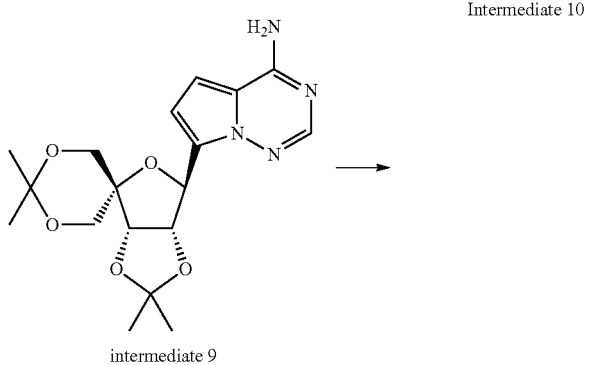

intermediate 9

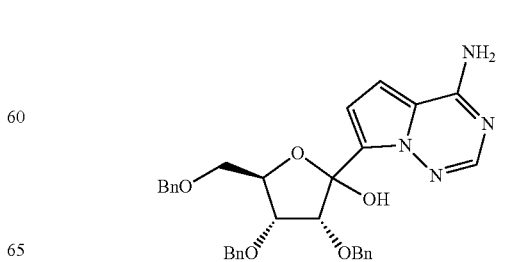

The product was prepared according to WO2015/069939. For example, pages 43-45 of WO2015/069939 provide a process for preparing this compound (identified as compound Id in WO2015/069939). Alternatively, it was prepared as following.

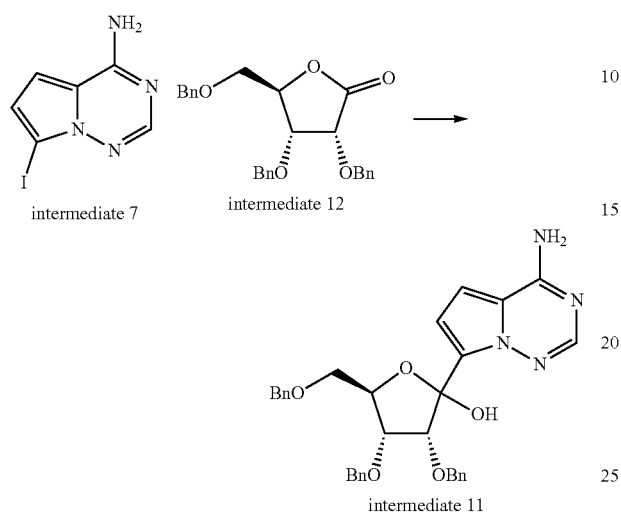

intermediate 7    intermediate 12 intermediate 11

A cylindrical reactor equipped with a retreat-curve overhead agitator, thermocouple, and $N_2$ bubbler was charged anhydrous $NdCl_3$ (60.00 g, 239 mol, 1.00 equiv), n-Bu$_4$NCl (71.51 g, 239 mmol, 1.0 equiv), and THF (900 g). The resulting mixture was concentrated to about 450 mL at ambient pressure under an $N_2$ pad using a 90° C. jacket temperature. THF (500 g) was charged and the distillation was repeated (twice). The mixture was cooled to 22° C. and intermediate 12 ((3R,4R,5R)-3,4-bis(benzyloxy)-5-((benzyloxy)methyl)dihydrofuran-2(3H)-one) (100.02 g, 239 mmol, 1.00 equiv) was charged. After 30 min the mixture was cooled to −20° C. and held. In a separate reaction flask iodopyrrolotriazine intermediate 7 (68.52 g, 264 mmol, 1.10 equiv) and THF (601 g) were combined and cooled to 0° C. TMSCl (28.64 g, 264 mmol, 1.10 equiv) was added slowly and, after about 30 min the mixture was cooled to 10° C. PhMgCl (2.0 M in THF, 270.00 g, 5.18 mmol, 2.17 equiv) was added slowly and the mixture was agitated for about 30 min and cooled to −20° C. i-PrMgCl (2.0 M in THF, 131.13 g, 269 mmol, 1.13 equiv) was added slowly. After about 2 h, the Grignard reaction mixture was transferred into the lactone/NdCl$_3$/n Bu$_4$NCl/THF mixture via cannula and the mixture was agitated at about 20° C. After about 16 h a solution of acetic acid (100 g) in water (440 g) was added and the mixture was warmed to 22° C. $^i$PrOAc (331 g) was added and the layers were separated. The organic layer was washed with 10% KHCO$_3$(aq) (2×500 g) and 10% NaCl(aq) (500 g). The organic layer was concentrated to about 450 mL and $^i$PrOAc (870 g) was charged. The organic mixture was washed with water (2×500 g) and concentrated to about 450 mL. $^i$PrOAc (435 g) was charged and the mixture was concentrated to about 450 mL. The mixture was filtered and residues were rinsed forward with 129 g $^i$PrOAc. The filtrate was concentrated to about 250 mL and MTBE (549 g) was charged and the mixture was adjusted to 22° C. Seed crystals (0.15 g) were charged, followed by n-heptane (230 mL) and the mixture was cooled to 0° C. The solids were isolated by filtration and rinsed forward with an MTBE/n-heptane mixture (113 g/30 g). The resulting solids were dried under vacuum at 35° C. to afford the intermediate 11 (79% yield and 99.92% LC purity).

Intermediate 13. (3aS,4R,6S,6aS)-6-(4-aminopyrrolo[2,1-f][1,2,4]triazin-7-yl)-4-(((tert-butyldimethylsilyl)oxy)methyl)-2,2-dimethyltetrahydrofuro[3,4-d][1,3]dioxole-4-carbonitrile

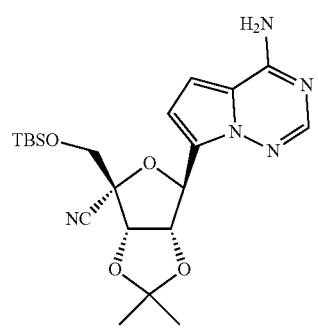 [SMILES: CC1(C)O[C@H]2[C@H](c3ccc4c(N)ncnn34)O[C@](C#N)(CO[Si](C)(C)C(C)(C)C)[C@H]2O1]

The product was prepared according to WO2015/069939. For example, pages 127-138 of WO2015/069939 provide a process for preparing this compound (identified as compound 14k in WO2015/069939).

Alternatively, intermediate 10 was prepared as described above and then converted to intermediate 13 as described in WO2015/069939 (conversion of compound 14f in WO2015/069939 to compound 14k in WO2015/069939, as described on pages 133-138 of WO2015/069939).

Alternatively, intermediate 11 was prepared as described above and then converted to intermediate 13 as described in WO2015/069939 (conversion of compound id in WO2015/069939 to compound 14k in WO2015/069939, as described on pages 45-46 and 127-138 of WO2015/069939).

Intermediate 14. (3aS,4R,6S,6aS)-6-(4-aminopyrrolo[2,1-f][1,2,4]triazin-7-yl)-4-(hydroxymethyl)-2,2-dimethyltetrahydrofuro[3,4-d][1,3]dioxole-4-carbonitrile

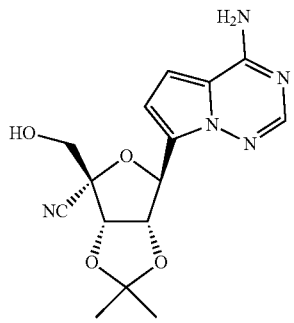 [SMILES: CC1(C)O[C@H]2[C@H](c3ccc4c(N)ncnn34)O[C@](C#N)(CO)[C@H]2O1]

Took up Intermediate 13 (8.41 g, 18.87 mmol) in THF (100 mL). Added TBAF 1.0 M in THF (28.31 mL, 28.31 mmol) in one portion at ambient temperature. Allowed to stir at ambient temperature for 10 min. The reaction was determined to be complete by LCMS. The reaction mixture was quenched with water and the organics were removed under reduced pressure. The crude was partitioned between EtOAc and Water. The layers were separated and the aqueous was washed with EtOAc. The organics were combined and dried over sodium sulfate. The solids were filtered off and the solvent removed under reduced pressure. The crude was purified by silica gel chromatography 120 g column 0-10% CH$_3$OH in CH$_2$Cl$_2$ to afford the product. LC/MS: t$_R$=0.76 min, MS m/z=332.14 [M+1]; LC system: Thermo Accela 1250 UHPLC. MS system: Thermo LCQ Fleet; Column: Kinetex 2.6μ XB-C18 100A, 50×3.00 mm. Solvents: Acetonitrile with 0.1% formic acid, Water with 0.1% formic acid. Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min. $^1$H NMR (400 MHz, DMSO-d$_6$) δ 7.87-7.80 (m, 3H), 6.85 (d, J=4.5 Hz, 1H), 6.82 (d, J=4.5 Hz, 1H), 5.74 (t, J=5.8 Hz, 1H), 5.52 (d, J=4.2 Hz, 1H), 5.24 (dd, J=6.8, 4.2 Hz, 1H), 4.92 (d, J=6.8 Hz, 1H), 3.65 (dd, J=6.1, 1.7 Hz, 2H), 1.61 (s, 3H), 1.33 (s, 3H).

Intermediate 15. (S)-cyclohexyl 2-aminopropanoate hydrochloride

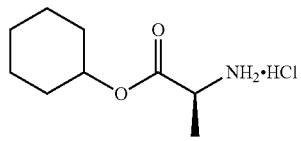

To a mixture of L-alanine (5 g, 56.12 mmol) and cyclohexanol (56 g, 561 mmol) was added TMSCl (20 mL). The resulting mixture was stirred at about 70° C. for about 15 h and concentrated in vacuo at about 80° C., co-evaporated with toluene, dissolved in hexanes, and stirred at about room temperature, during which solid was precipitated. The solid was collected by filtration and the filter cake was washed with 5% EtOAc in hexanes several times, and dried under high vacuum for about 15 h to give the product. $^1$H NMR (400 MHz, Chloroform-d) δ 8.76 (s, 3H), 4.85 (tt, J=8.7, 3.8 Hz, 1H), 4.17 (p, J=6.5 Hz, 1H), 1.84 (dd, J=9.9, 5.5 Hz, 2H), 1.70 (d, J=7.3 Hz, 5H), 1.57-1.42 (m, 3H), 1.32 (m, 3H).

Intermediate 16. (2S)-cyclohexyl 2-(((4-nitrophenoxy)(phenoxy)phosphoryl)amino) propanoate

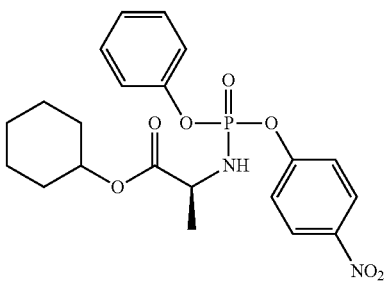 [SMILES: C[C@H](NP(=O)(Oc1ccccc1)Oc1ccc([N+](=O)[O-])cc1)C(=O)OC1CCCCC1]

Intermediate 15 (3.4 g, 16.37 mmol) was dissolved in methylene chloride (45 mL), cooled to −78° C., and phenyl dichlorophosphate (2.45 mL, 16.37 mmol) added quickly. Triethylamine (4.54 mL, 32.74 mmol) was added over 60 min at −78° C. and then 4-nitrophenol (2277 mg, 16.37 mmol) was added in one portion. Triethylamine (2.27 mL, 16.37 mmol) was added over 60 min at −78° C. The resulting mixture was stirred for 2 h at −78° C., diluted with methylene chloride (100 mL), washed with water twice and brine, dried over sodium sulfate, and concentrated in vacuo. The residue was purified by silica gel column chromatography (EtOAc 0 to 20% in hexanes) to give the product. $^1$H NMR (400 MHz, Chloroform-d) δ 8.22 (m, 2H), 7.46-7.30 (m, 4H), 7.29-7.09 (m, 3H), 4.76 (m, 1H), 4.20-4.02 (m, 1H), 3.92 (m, 1H), 1.87-1.64 (m, 4H), 1.54 (m, 2H), 1.46-1.18 (m, 7H). $^{31}$P NMR (162 MHz, Chloroform-d) δ −2.94, −3.00. MS m/z=449 (M+H)$^+$.

B. Compounds

Example 1. Preparation of (2S)-cyclohexyl 2-(((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)amino)propanoate (Formula Ia)

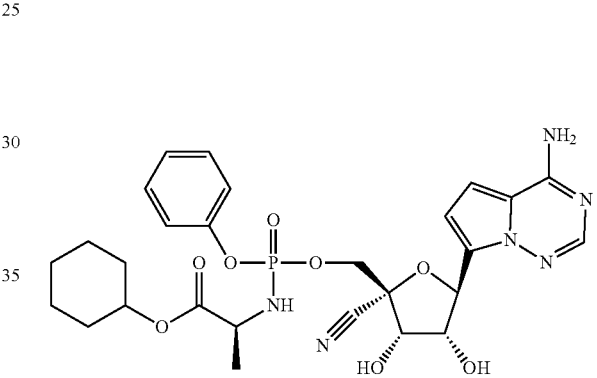

To a mixture of Intermediate 14 (99 mg, 0.30 mmol), Intermediate 16 (201 mg, 0.45 mmol), and MgCl$_2$ (43 mg, 0.45 mmol) in DMF (4 mL) was added N,N-diisopropylethylamine (0.13 mL, 0.75 mmol) dropwise at room temperature. The resulting mixture was stirred at room temperature for 15 h and purified by preparative HPLC (Phenominex Synergi 4u Hydro-RR 80 Å 150×30 mm column, 10-100% acetonitrile/water gradient) to give an intermediate, which was dissolved in ACN (3 mL) and c-HCl (0.1 mL) was added. The resulting mixture was stirred at 50° C. for 2 h, cooled, and purified by preparative HPLC (Phenominex Synergi 4u Hydro-RR 80 Å 150×30 mm column, 10-80% acetonitrile/water gradient) to give the product. $^1$H NMR (400 MHz, Methanol-d4) δ 7.80 (s, 0.5H), 7.78 (s, 0.5H), 7.42-7.05 (m, 5H), 6.84 (m, 1H), 6.73 (m, 1H), 5.50 (m, 1H), 4.64 (m, 2H), 4.57-4.25 (m, 3H), 3.86 (m, 1H), 1.91-1.61 (m, 4H), 1.61-1.09 (m, 9H). $^{31}$P NMR (162 MHz, Methanol-d4) δ 3.3. MS m/z=601 (M+H)$^+$. Separation of the Diastereomers. The product was purified via chiral preparatory HPLC (Chiralpak IA, 150×4.6 mm, Heptane 70% Ethanol 30%).

Example 2. Preparation of cyclohexyl ((R)-(((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate (Formula Ib)

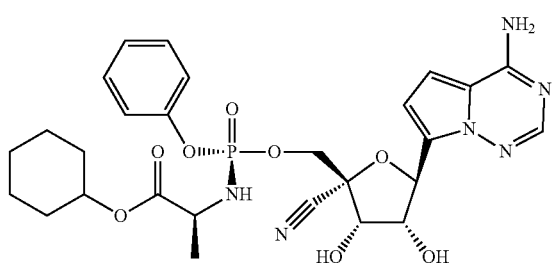 [SMILES: C[C@H](N[P@@](=O)(OC[C@@]1(C#N)O[C@@H](c2ccc3c(N)ncnn23)[C@H](O)[C@@H]1O)Oc1ccccc1)C(=O)OC1CCCCC1]

First Eluting Diastereomer of Example 1: $^1$H NMR (400 MHz, Methanol-$d_4$) δ 7.78 (s, 1H), 7.34-7.23 (m, 2H), 7.19-7.10 (m, 3H), 6.85 (d, J=4.5 Hz, 1H), 6.73 (d, J=4.5 Hz, 1H), 5.51 (d, J=5.0 Hz, 1H), 4.69 (td, J=8.8, 4.2 Hz, 1H), 4.62 (t, J=5.3 Hz, 1H), 4.53-4.44 (m, 2H), 4.36 (dd, J=10.9, 5.2 Hz, 1H), 3.86 (dq, J=9.4, 7.1 Hz, 1H), 1.85-1.62 (m, 4H), 1.58-1.20 (m, 9H). $^{31}$P NMR (162 MHz, Methanol-$d_4$) δ 3.31.

Example 3. Preparation of cyclohexyl ((S)-(((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate (Formula I)

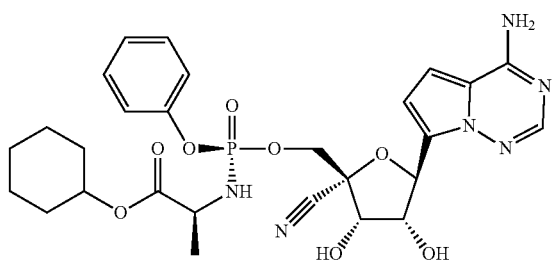 [SMILES: C[C@H](N[P@](=O)(OC[C@@]1(C#N)O[C@@H](c2ccc3c(N)ncnn23)[C@H](O)[C@@H]1O)Oc1ccccc1)C(=O)OC1CCCCC1]

Second Eluting Diastereomer of Example 1: $^1$H NMR (400 MHz, Methanol-$d_4$) δ 7.80 (s, 1H), 7.37-7.27 (m, 2H), 7.26-7.13 (m, 3H), 6.84 (d, J=4.5 Hz, 1H), 6.73 (d, J=4.5 Hz, 1H), 5.49 (d, J=5.0 Hz, 1H), 4.71-4.56 (m, 2H), 4.46 (d, J=5.6 Hz, 1H), 4.45-4.30 (m, 2H), 3.97-3.77 (m, 1H), 1.80-1.61 (m, 4H), 1.55-1.21 (m, 9H). $^{31}$P NMR (162 MHz, Methanol-$d_4$) δ 3.31.

Example 4. Synthesis of isopropyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate (Compound 3)

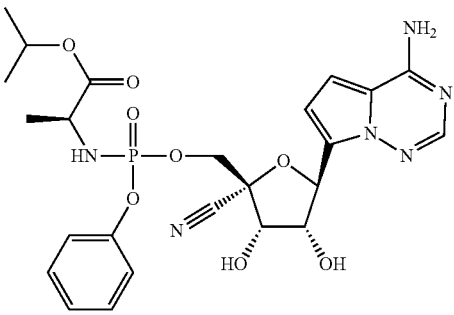 [SMILES: CC(C)OC(=O)[C@H](C)NP(=O)(OC[C@@]1(C#N)O[C@@H](c2ccc3c(N)ncnn23)[C@H](O)[C@@H]1O)Oc1ccccc1]

(2R,3S,4R,5S)-5-(4-aminopyrrolo[2,1-f][1,2,4]triazin-7-yl)-3,4-dihydroxy-2-(hydroxymethyl)tetrahydrofuran-2-carbonitrile was prepared according WO2015/069939. For example, pages 43-54 of WO2015/069939 provide a process for preparing the compound, identified as compound 1 in WO2015/069939.

(2R,3S,4R,5S)-5-(4-aminopyrrolo[2,1-f][1,2,4]triazin-7-yl)-3,4-dihydroxy-2-(hydroxymethyl)tetrahydrofuran-2-carbonitrile (0.149 g, 0.512 mmol) taken up in anhydrous THF and concentrated. The resulting residue was placed under high vacuum for 1.5 hours. The residue was then dissolved in NMP (4 mL) and then THF (1 mL) was added. This solution was cooled in an ice bath and a 1 M solution of tert-BuMgCl in THF (0.767 mL, 0.767 mmol) was added, causing a white precipitate to form. After 5 minutes the cold bath was removed, the mixture was sonicated to disperse the precipitate solids, and the reaction was stirred at room temperature for 10 minutes. A solution of intermediate isopropyl ((4-nitrophenoxy)(phenoxy)phosphoryl)-L-alaninate (0.251 g, 0.614 mmol; WO2011123668) in THF (0.9 mL) was added. The reaction was stirred at room temperature and progress was monitored by LC/MS. After 1 hour 45 minutes the reaction was cooled in an ice bath and quenched by the addition of glacial AcOH (0.25 mL). The ice bath was removed and stirring was continued for 5 minutes at room temperature. Volatiles were removed by evaporation and the product was isolated from the residue by HPLC. $^1$H NMR (400 MHz, Methanol-$d_4$, chemical shift with asterisk (*) denotes shift of associated proton(s) on the $2^{nd}$ isomer present) δ 7.81 (s, 0.41H), 7.79* (s, 0.59H), 7.36-7.12 (m, 5H), 6.85 (m, 1H), 6.74 (m, 1H), 5.50 (m, 1H), 4.97-4.85 (m, 1H), 4.63 (m, 1H), 4.54-4.32 (m, 3H), 3.85 (m, 1H), 1.25 (d, J=7.1 Hz, 2H), 1.20* (d, J=6.3 Hz, 4H), 1.16 (t, J=6.3 Hz, 3H). $^{31}$P NMR (162 MHz, Methanol-$d_4$) δ 3.30 (s). MS m/z=561.03 [M+1].

Example 5. Synthesis of (S)-isopropyl 2-(((S)-(((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)amino)propanoate (Compound 4)

(2R,3S,4R,5S)-5-(4-aminopyrrolo[2,1-f][1,2,4]triazin-7-yl)-3,4-dihydroxy-2-(hydroxymethyl)tetrahydrofuran-2-carbonitrile was prepared as described in Example 4.

Isopropyl ((S)-(4-nitrophenoxy)(phenoxy)phosphoryl)-L-alaninate was prepared as described in Cho et al., J. Med. Chem. 2014, 57, 1812-1825.

(2R,3S,4R,5S)-5-(4-aminopyrrolo[2,1-f][1,2,4]triazin-7-yl)-3,4-dihydroxy-2-(hydroxymethyl)tetrahydrofuran-2-carbonitrile (50 mg, 0.172 mmol) and isopropyl ((S)-(4-nitrophenoxy)(phenoxy)phosphoryl)-L-alaninate (84 mg, 0.206 mmol) were mixed in anhydrous N,N-dimethylformamide (2 mL). Magnesium chloride (36 mg, 0.378 mmol) was added in one portion. The reaction mixture was heated at 50° C. N,N-Diisopropylethylamine (75 µL, 0.43 mmol) was added, and the reaction was stirred for 4.5 hrs at 50° C. The reaction mixture was cooled, diluted with ethyl acetate (30 mL) and washed with 5% aqueous citric acid solution (10 mL) and then brine (10 mL). The organic layer was dried over anhydrous sodium sulfate and concentrated under reduced pressure. The crude was purified via $SiO_2$ column chromatography (4 g $SiO_2$ Combiflash HP Gold Column 0-2-5% methanol/dichloromethane) to afford the product. $^1$H NMR (400 MHz, Methanol-$d_4$) δ 7.79 (s, 1H), 7.36-7.25 (m, 2H), 7.25-7.12 (m, 3H), 6.84 (d, J=4.5 Hz, 1H), 6.73 (d, J=4.5 Hz, 1H), 5.49 (d, J=5.1 Hz, 1H), 4.91-4.84 (m, 1H), 4.62 (dd, J=5.6, 5.0 Hz, 1H), 4.47 (d, J=5.6 Hz, 1H), 4.45-4.30 (m, 2H), 3.85 (dq, J=10.0, 7.1 Hz, 1H), 1.25 (d, J=7.2 Hz, 3H), 1.15 (t, J=6.4 Hz, 6H). $^{31}$P NMR (162 MHz, Methanol-$d_4$) δ 3.31. MS m/z=561.0 [M+1], 559.0 [M−1].

Example 6. Synthesis of (2S)-pentan-3-yl 2-(((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)amino)propanoate (Compound 5)

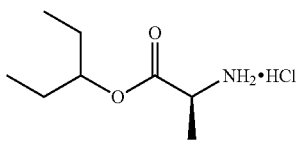

(S)-pentan-3-yl 2-aminopropanoate hydrochloride. To a mixture of L-alaninate (5 g, 56.12 mmol) and 3-hydroxypentane (50 mL) was added TMSCl (20 mL). The resulting mixture was stirred at 70° C. for 15 h and concentrated in rotary evaporator at 80° C. The resulting solid was triturated with 5% EtOAc in hexanes, filtered, and washed with 5% EtOAc in hexanes several times, and dried under high vacuum over night to give the intermediate. $^1$H NMR (400 MHz, Chloroform-d) δ 8.79 (s, 3H), 4.83 (p, J=6.2 Hz, 1H), 4.19 (p, J=6.5 Hz, 1H), 1.72 (d, J=7.2 Hz, 3H), 1.67-1.52 (m, 4H), 0.88 (td, J=7.5, 1.7 Hz, 6H).

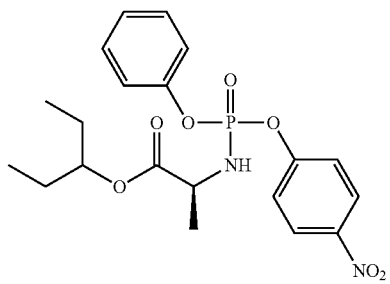 [SMILES: CCC(CC)OC(=O)[C@H](C)NP(=O)(Oc1ccccc1)Oc1ccc([N+](=O)[O-])cc1]

(2S)-pentan-3-yl 2-(((4-nitrophenoxy)(phenoxy)phosphoryl)amino) propanoate. (S)-pentan-3-yl 2-aminopropanoate hydrochloride (1.00 g, 5.11 mmol) was suspended in methylene chloride (15 mL), cooled to −78° C., and phenyl dichlorophosphate (0.76 mL, 5.11 mmol) added quickly. Triethylamine (1.42 mL, 10.22 mmol) was added over 30 min at −78° C. and the resulting mixture was stirred at −78° C. for 30 min. Then 4-nitrophenol (711 mg, 5.11 mmol) was added in one portion and triethylamine (0.71 mL, 5.11 mmol) was added over 30 min at −78° C. The mixture was stirred for 30 min at −78° C., washed with water and brine, dried over sodium sulfate, and concentrated in vacuo. The residue was purified by silica gel column chromatography (EtOAc 0 to 20% in hexanes) to give (2S)-pentan-3-yl 2-(((4-nitrophenoxy)(phenoxy)phosphoryl)amino) propanoate. $^1$H NMR (400 MHz, Chloroform-d) δ 8.22 (m, 2H), 7.46-7.30 (m, 4H), 7.31-7.14 (m, 3H), 4.78 (m, 1H), 4.27-4.04 (m, 1H), 3.98-3.77 (m, 1H), 1.72-1.45 (m, 4H), 1.42 (m, 3H), 0.84 (m, 6H). $^{31}$P NMR (162 MHz, Chloroform-d) δ −2.99, −3.06. MS m/z=437 (M+H)$^+$.

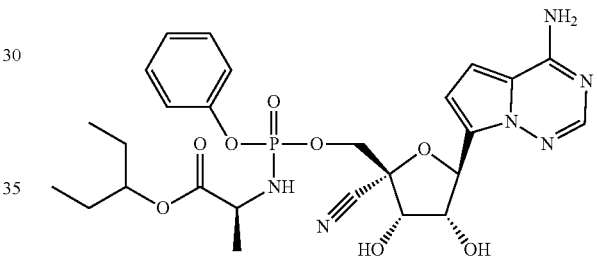

(2S)-pentan-3-yl 2-(((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)amino) propanoate. To a mixture of Intermediate 14 (66 mg, 0.30 mmol), (2S)-pentan-3-yl 2-(((4-nitrophenoxy)(phenoxy)phosphoryl)amino)propanoate (170 mg, 0.39 mmol), and $MgCl_2$ (28 mg, 0.30 mmol) in DMF (3 mL) was added N,N-diisopropylethylamine (0.087 mL, 0.50 mmol) dropwise at room temperature. The resulting mixture was stirred at 60° C. for 15 h and purified by HPLC (ACN 0 to 100% in water) to give an intermediate which, was dissolved in ACN (3 mL) and C—HCl (0.1 mL) was added. The resulting mixture was stirred at 50° C. for 2 h, and purified by preparative HPLC (Phenominex Synergi 4u Hydro-RR 80 Å 150×30 mm column, 5-100% acetonitrile/water gradient) to give the product. $^1$H NMR (400 MHz, Methanol-d4) δ 7.79 (m, 1H), 7.36-7.07 (m, 5H), 6.84 (m, 1H), 6.73 (m, 1H), 5.50 (m, 1H), 4.76-4.59 (m, 2H), 4.54-4.40 (m, 2H), 4.34 (m, 1H), 3.89 (m, 1H), 1.63-1.42 (m, 4H), 1.27 (m, 3H), 0.91-0.75 (m, 6H). $^{31}$P NMR (162 MHz, Methanol-d4) δ 3.37, 3.29. MS m/z=589 (M+H)$^+$.

Example 7. Synthesis of 2-ethylbutyl ((S)-(((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)alaninate (Compound 6)

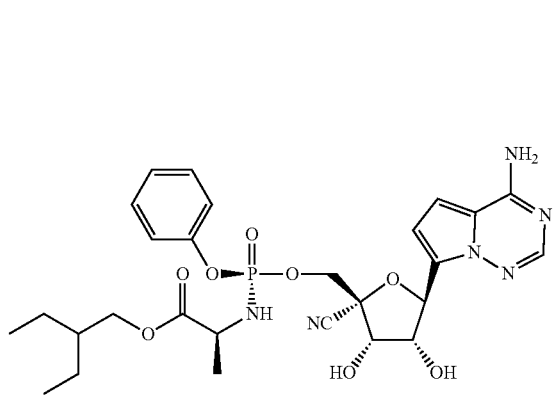 [SMILES: CCC(CC)COC(=O)[C@H](C)N[P@](=O)(OC[C@@]1(C#N)O[C@@H](c2ccc3c(N)ncnn23)[C@H](O)[C@@H]1O)Oc1ccccc1]

2-Ethylbutyl ((S)-(4-nitrophenoxy)(phenoxy)(phosphoryl)-L-alaninate was prepared as described in WO 2016/069825.

To a mixture of Intermediate 14 (700 mg, 2.113 mmol), 2-ethylbutyl ((S)-(4-nitrophenoxy)(phenoxy)(phosphoryl)-L-alaninate (998 mg, 2.218 mmol), and magnesium chloride (302 mg, 3.169 mmol) was added tetrahydrofuran (8.5 mL) at room temperature followed by the addition of N,N-Diisopropylethylamine (0.92 mL, 5.282 mmol). The resulting mixture was stirred at 50° C. for 3 h. The reaction mixture was then concentrated under reduced pressure and the residue obtained was diluted with saturated sodium chloride solution and dichloromethane. The layers were split and the organic layer was dried over anhydrous sodium sulfate, filtered and was concentrated under reduced pressure. The crude residue was purified via SiO$_2$ column chromatography (80 g SiO$_2$ Combiflash HP Gold Column, 100% Dichloromethane-14% Methanol in dichloromethane as eluent). Pure material obtained was dissolved in an anhydrous acetonitrile (10 mL) and was cooled in an ice bath followed by the dropwise addition of concentrated hydrochloric acid (4 mL, 48 mmol). The reaction mixture was stirred at room temperature for 1 h. After 1 h the reaction mixture was cooled in an ice bath and was diluted with water. Neutralized the solution with 3N sodium hydroxide and extracted with dichloromethane. Organic layer was separated, dried over sodium sulfate, filtered and concentrated. The residue obtained was purified by SiO$_2$ column chromatography (40 g SiO$_2$ Combiflash HP Gold Column, 100% Dichloromethane-20% Methanol in dichloromethane) to afford the product. $^1$H NMR (400 MHz, Methanol-d4) δ 7.80 (s, 1H), 7.38-7.29 (m, 2H), 7.27-7.13 (m, 3H), 6.84 (d, J=4.5 Hz, 1H), 6.74 (d, J=4.5 Hz, 1H), 5.49 (d, J=5.0 Hz, 1H), 4.61 (t, J=5.3 Hz, 1H), 4.49-4.29 (m, 3H), 4.04-3.82 (m, 3H), 1.43 (dq, J=12.5, 6.1 Hz, 1H), 1.37-1.23 (m, 7H), 0.84 (td, J=7.5, 1.1 Hz, 6H). $^{31}$P NMR (162 MHz, Acetonitrile-d3) δ 2.73. MS m/z=603 [M+1].

Example 8. Synthesis of 2-ethylbutyl ((R)-(((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate (Compound 7)

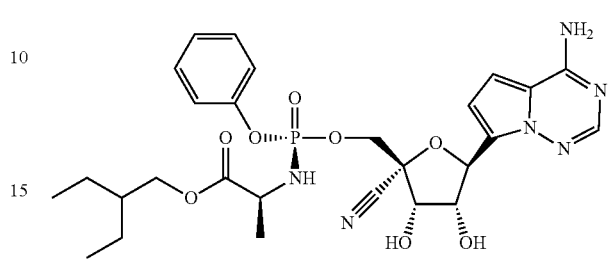

This compound was prepared by resolution of the Sp and Rp diastereomers of Example 34 from WO 2015/069939. Example 34 from WO 2015/069939 was purified via chiral preparatory SFC (Chiralpak AD-H, 30% Ethanol isocratic) to compound 7 as the First Eluting Diastereomer of Example 34 from WO 2015/069939: $^1$H NMR (400 MHz, methanol-d$_4$) δ 7.78 (s, 1H), 7.32-7.24 (m, 2H), 7.19-7.10 (m, 3H), 6.84 (d, J=4.5 Hz, 1H), 6.72 (d, J=4.5 Hz, 1H), 5.51 (d, J=5.0 Hz, 1H), 4.63 (t, J=5.3 Hz, 1H), 4.54-4.43 (m, 2H), 4.36 (m, 1H), 4.07-3.84 (m, 3H), 1.53-1.42 (m, 1H), 1.38-1.24 (m, 7H), 0.86 (t, J=7.5 Hz, 6H). $^{31}$P NMR (162 MHz, methanol-d$_4$) δ 3.26 (s). HPLC: t$_R$=5.068 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

Example 9. Synthesis of ethyl ((S)-(((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate (Compound 8)

Ethyl ((S)-(perfluorophenoxy)(phenoxy)phosphoryl)-L-alaninate

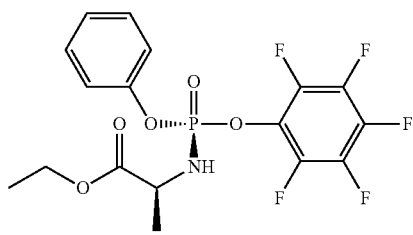 [SMILES: CCOC(=O)[C@H](C)N[P@](=O)(Oc1ccccc1)Oc1c(F)c(F)c(F)c(F)c1F]

To a solution of L-alanine ethyl ester-HCl (631 mg, 2.465 mmol) in DCM (15 mL) was added phenyl phosphorodichloridate (0.368 mL, 2.465 mmol) in one portion at −78° C. and triethylamine (0.68 mL, 4.93 mmol) was added dropwise over 5 min at −78° C. The resulting mixture was stirred for 30 min after removal of dry ice bath and then cooled to −78° C. Pentafluorophenol (454 mg, 2.465 mmol) was added in one portion and triethylamine (0.34 mL, 2.465 mmol) added over 5 min at −78° C. The resulting mixture was stirred for 1h after removal of dry ice bath, then diluted with DCM, washed with brine, concentrated in vacuo, and the resulting residue purified by silica gel column chromatography (EtOAc 0 to 60% in hexanes) to give a diastereomeric mixture, to which diisopropyl ether (4 mL) was added. The suspension was sonicated and filtered. ¹H NMR of the filter cake showed it is 3:1 ratio of mixture. Diisopropyl ether (5 mL) was added to the filter cake and the suspension was heated at 70° C. to a clear solution. Upon removal of heating bath, needle like crystals started to form and after 10 min, the mixture was filtered and the filter cake was dried under high vacuum for 30 min to afford the Sp isomer.

Diastereomeric mixture: ¹H NMR (400 MHz, Chloroform-d) δ 7.43-7.30 (m, 2H), 7.32-7.17 (m, 3H), 4.29-4.11 (m, 3H), 3.94 (m, 1H), 1.52-1.42 (m, 3H), 1.28 (q, J=7.0 Hz, 3H).

Sp isomer: ¹H NMR (400 MHz, Acetonitrile-d3) δ 7.50-7.36 (m, 2H), 7.32-7.21 (m, 3H), 4.75 (t, J=11.5 Hz, 1H), 4.17-3.98 (m, 3H), 1.37 (dd, J=7.1, 1.1 Hz, 3H), 1.22 (t, J=7.1 Hz, 3H). ³¹P NMR (162 MHz, Acetonitrile-d3) δ −0.51. ¹⁹F NMR (376 MHz, Acetonitrile-d3) δ −155.48-−155.76 (m), −162.73 (td, J=21.3, 3.7 Hz), −165.02-−165.84 (m). LCMS m/z=440.5 (M-ethyl+H), $t_R$=1.57 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min.

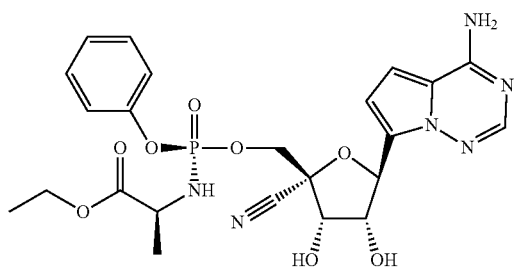 [SMILES: CCOC(=O)[C@H](C)N[P@](=O)(OC[C@@]1(C#N)O[C@@H](c2ccc3c(N)ncnn23)[C@H](O)[C@@H]1O)Oc1ccccc1]

To a mixture of Intermediate 14 (150 mg, 0.45 mmol), ethyl ((S)-(perfluorophenoxy)(phenoxy)phosphoryl)-L-alaninate (298 mg, 0.68 mmol), and MgCl₂ (65 mg, 0.68 mmol) in THF (6 mL) was added N,N-diisopropylethylamine (0.20 mL, 1.13 mmol) dropwise. The resulting mixture was stirred at 50° C. for 2h, cooled, diluted with EtOAc (150 mL), washed with brine (50 mL×2), dried, concentrated in vacuo, redissolved in acetonitrile (6 mL), and c-HCL (0.3 mL) added in ice bath. The resulting mixture was stirred for 1 h in ice bath and 1 h at room temperature, treated with sat NaHCO₃ (2 mL), purified by HPLC (Phenomenex Gemini-NX 10μ C18 110° A 250×30 mm column, 5-70% acetonitrile/water gradient in 25 min run) to afford the product. ¹H NMR (400 MHz, Methanol-d4) δ 7.80 (s, 1H), 7.31 (d, J=7.7 Hz, 2H), 7.25-7.14 (m, 3H), 6.84 (d, J=4.5 Hz, 1H), 6.73 (d, J=4.6 Hz, 1H), 5.49 (d, J=5.1 Hz, 1H), 4.62 (t, J=5.3 Hz, 1H), 4.46 (d, J=5.6 Hz, 1H), 4.40 (dd, J=10.9, 6.2 Hz, 1H), 4.33 (dd, J=10.9, 5.4 Hz, 1H), 4.11-3.98 (m, 2H), 3.87 (dd, J=9.9, 7.1 Hz, 1H), 1.25 (dd, J=7.1, 1.0 Hz, 3H), 1.16 (t, J=7.1 Hz, 3H). ³¹P NMR (162 MHz, Methanol-d4) δ 3.26. LCMS: MS m/z=547.12 [M+1]; $t_R$=0.76 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=4.03 min; HPLC system: Agilent 1290 II; Column: Phenomenex Kinetex C18, 2.6u 110A, 100×4.6 mm; Solvents: A: Water with 0.1% TFA, B: Acetonitrile with 0.1% TFA; Gradient: 2-98% B with 8.5 min gradient at 1.5 mL/min.

C. Biological Examples

Example 10. DENV Pol IC₅₀

A 244 nucleotide secondary structureless heteropolymeric RNA (sshRNA) with sequence 5'-(UCAG)20(UCCAAG)14(UCAG)20-3' (SEQ ID NO: 1) was used as the template with 5'-CUG-3' primer in the DENV2-NS5 polymerase assay. Six two-fold dilutions of compounds starting from 200 nM and no inhibitor control were plated in 96-well plates. 100 nM DENV2 NS5 was preincubated for 5 minutes at room temperature in a reaction mixture containing 40 mM Tris-HCl (pH 7.5), 10 mM NaCl, 3 mM DTT, 0.2 unit/μL RNasin Plus RNase Inhibitor, 200 ng/μL sshRNA, 20 μM CUG and 2 mM MgCl2. Enzyme mix was added to compound dilutions and reactions initiated by the addition of a mixture containing 20 μM of three natural NTP plus 2 μM of analog:base matched competing natural NTP containing 1:100 α-33P-NTP. After 90 minutes at 30° C., 5 μL of the reaction mixtures were spotted on DE81 anion exchange paper. Filter papers were washed three times with Na₂HPO₄ (125 mM, pH 9) for 5 minutes, rinsed with water and ethanol, then air-dried and exposed to phosphorimager. Synthesized RNA was quantified using Typhoon Trio Imager and Image Quant TL Software and reaction rates were calculated by linear regression using GraphPad Prism 5.0. IC₅₀ values were calculated in Prism by non-linear regression analysis using the dose-response (variable slope) equation (four-parameter logistic equation): Y=Bottom+(Top-Bottom)/(1+10^((Log IC₅₀−X)*HillSlope)).

Example 11. RSV RNP Preparation

RSV ribonucleoprotein (RNP) complexes were prepared from a method modified from Mason et al. (Mason, S., Lawetz, C., Gaudette, Y., Do, F., Scouten, E., Lagace, L., Simoneau, B. and Liuzzi, M. (2004) Polyadenylation-dependent screening assay for respiratory syncytial virus RNA transcriptase activity and identification of an inhibitor. Nucleic Acids Research, 32, 4758-4767). HEp-2 cells were plated at a density of 7.1×10⁴ cells/cm² in MEM+10% fetal bovine serum (FBS) and allowed to attach overnight at 37° C. (5% CO₂). Following attachment, the cells were infected with RSV A2 (MOI=5) in 35 mL MEM+2% FBS. At 20 hours post-infection, the media was replaced with MEM+2% FBS supplemented with 2 μg/mL actinomycin D and returned to 37° C. for one hour. The cells were then washed once with PBS and treated with 35 mL of PBS+250 μg/mL lyso-lecithin for one minute, after which all liquid was aspirated. The cells were harvested by scrapping them into 1.2 mL of buffer A [50 mM TRIS acetate (pH 8.0), 100 mM potassium acetate, 1 mM DTT and 2 μg/mL actinomycin D] and lysed by repeated passage through an 18 gauge needle (10 times). The cell lysate was placed in ice for 10 minutes and then centrifuged at 2400 g for 10 minutes at 4° C. The supernatant (S1) was removed and the pellet (P1) was disrupted in 600 μL of Buffer B [10 mM TRIS acetate (pH 8.0), 10 mM potassium acetate and 1.5 mM MgCl₂] supplemented with 1% Triton X-100 by repeated passage through an 18 gauge needle (10 times). The resuspended pellet was placed in ice for 10 minutes and then centrifuged at 2400 g for 10 minutes at 4° C. The supernatant (S2) was removed and the pellet (P2) was disrupted in 600 µL of Buffer B supplemented with 0.5% deoxycholate and 0.1% Tween 40. The resuspended pellet was placed in ice for 10 minutes and then centrifuged at 2400 g for 10 minutes at 4° C. The supernatant (S3) fraction, containing the enriched RSV RNP complexes, was collected and the protein concentration determined by UV absorbance at 280 nm. Aliquoted RSV RNP S3 fractions were stored at −80° C.

Example 12. RSV RNP Assay

Transcription reactions contained 25 µg of crude RSV RNP complexes in 30 µL of reaction buffer [50 mM TRIS-acetate (pH 8.0), 120 mM potassium acetate, 5% glycerol, 4.5 mM $MgCl_2$, 3 mM DTT, 2 mM ethyleneglycol-bis(2-aminoethylether)-tetraacetic acid (EGTA), 50 µg/mL BSA, 2.5 U RNasin (Promega), ATP, GTP, UTP, CTP and 1.5 uCi [α-32P] NTP (3000 Ci/mmol)]. The radiolabeled nucleotide used in the transcription assay was selected to match the nucleotide analog being evaluated for inhibition of RSV RNP transcription. Cold, competitive NTP was added at a final concentration of one-half its Km (ATP=20 µM, GTP=12.5 µM, UTP=6 µM and CTP=2 µM). The three remaining nucleotides were added at a final concentration of 100 µM.

To determine whether nucleotide analogs inhibited RSV RNP transcription, compounds were added using a 6 step serial dilution in 5-fold increments. Following a 90 minute incubation at 30° C., the RNP reactions were stopped with 350 µL of Qiagen RLT lysis buffer and the RNA was purified using a Qiagen RNeasy 96 kit. Purified RNA was denatured in RNA sample loading buffer (Sigma) at 65° C. for 10 minutes and run on a 1.2% agarose/MOPS gel containing 2 M formaldehyde. The agarose gel was dried and exposed to a Storm phosphorimager screen and developed using a Storm phosphorimager (GE Healthcare). The concentration of compound that reduced total radiolabeled transcripts by 50% ($IC_{50}$) was calculated by non-linear regression analysis of two replicates.

Example 13. DENV-2 moDC $EC_{50}$

Human monocyte-derived dendritic cells (moDCs) were derived from CD14+ monocytes (AllCells) cultured in Human Mo-DC Differentiation medium containing GM-CSF and IL-4 (Miltenyi Biotec). On day 7, moDCs were harvested by mechanical disruption, washed and suspended in serum-free RPMI. moDCs were infected with Vero-derived Dengue 2, New Guinea strain (NGC) at a MOI=0.1 for two hours in serum-free RPMI with gentle agitation at 37° C. Cells were washed and resuspended in 10% serum-containing RPMI (Gibco, supplemented with sodium pyruvate, NEAA, Penicillin-Streptomycin). 10^5 cells were plated in triplicate in 96-well plates with compounds dispensed at graded doses (Hewlett-Packard D300 Digital Dispenser). All wells were normalized to 0.25% DMSO. At 48 hours, cells were washed with 1× PBS and all supernatants removed. Total RNA was extracted using RNEasy 96 plates (Qiagen) and used to generate first-strand cDNA using XLT cDNA 5× Supermix (QuantaBio). cDNA was used as a template in a Taqman qPCR duplex reaction specific to DENV2 viral and GAPDH gene expression. $EC_{50}$ values were determined using Prism Graphpad software, with normalization to a positive control and no compound negative control wells.

Example 14. DENV-2 Huh-7 $EC_{50}$

Huh7 (Human hepatocarcinoma 7) cells were maintained in 10% FCS-containing DMEM complete media. On the day of the assay, cells were trypsinized (0.1% Trypsin-EDTA), washed and infected for 2 hours in serum-free DMEM with Dengue serotype 2 New Guinea C (NGC) strain at MOI=0.1 with gentle agitation at 37° C. After 2 hours, cells were washed with serum-free media and suspended in 10% FCS-containing DMEM (Gibco, supplemented with sodium pyruvate, NEAA, Penicillin-Streptomycin). 10=cells were plated in triplicate in 96-well plates with compounds dispensed at graded doses (Hewlett-Packard D300 Digital Dispenser). All wells were normalized to 0.25% DMSO. At 48 hours, cells were washed with 1× PBS and all supernatants removed. Total RNA was extracted using RNEasy 96 plates (Qiagen) and used to generate first-strand cDNA using XLT cDNA 5× Supermix (QuantaBio). cDNA was used as a template in a Taqman qPCR duplex reaction specific to DENV2 viral and GAPDH gene expression. $EC_{50}$ values were determined using Prism Graphpad software, with normalization to a positive control and no compound negative control wells.

Example 15. DENV-2 Huh-7 Rep $EC_{50}$

In 384 well plates (Greiner, Cat #781091), compounds were acoustically transferred at 200 nl per well in a 8 compound (4 replicates) or 40 compound dose response format (3 replicates). For all plates tested, Balapiravir, GS-5734 and NITD008 were included as positive inhibition controls alongside 0% inhibition, DMSO-only negative control wells. Following compound addition, Huh-7 cells containing the DENV2 replicon construct were harvested following standard cell culture procedures and were adjusted to a concentration of 1.25E5 cells/mL in cell culture media composed of cDMEM without genticin. 40 µL of the cell stock was then added to each well for a final cell density of 5,000 cells/well. Cell and compound mixtures were incubated at 37° C./5% $CO_2$ for 48 hours. Prior to harvesting cells, EnduRen Live Cell Substrate (Promega, Cat #E6481) was prepared by suspending 3.4 mg into 100 uL of DMSO to generate a 60 mM stock solution. The stock solution was then diluted 1:200 in pre-warmed cDMEM and 10 uL of this diluted solution was added to each well of the 384 well plates. Plates were then centrifuged at 500 rpm briefly and were placed on a plate shaker for 2 min. Following mixing, plates were incubated at 7° C./5% $CO_2$ for 1.5 hours prior to measuring luminescence on an Envision luminometer. The percentage inhibition of replicon signal was calculated for each tested concentration relative to the 0% and 100% inhibition controls and the $EC_{50}$ value for each compound was determined by 4-parametric non-linear regression as the effective concentration of compound that inhibited replicon signal by 50%.

Example 16. RSV HEp-2 $EC_{50}$

Antiviral activity against RSV is determined using an infectious cytopathic cell protection assay in HEp-2 cells. In this assay, compounds inhibiting viral infection and/or replication produce a cytoprotective effect against the virus-induced cell killing that can be quantified using a cell viability reagent. The techniques used here are novel adaptations of methods described in published literature (Chapman et al., Antimicrob Agents Chemother. 2007, 51(9): 3346-53.).

HEp-2 cells are obtained from ATCC (Manassas, VI) and maintained in MEM media supplemented with 10% fetal bovine serum and penicillin/streptomycin. Cells are passaged twice a week and kept at subconfluent stage. Commercial stock of RSV strain A2 (Advanced Biotechnologies, Columbia, MD) is titered before compound testing to determine the appropriate dilution of the virus stock that generates desirable cytopathic effect in HEp-2 cells.

For antiviral tests, HEp-2 cells are grown in large cell culture flasks to near confluency but not fully so. The compounds to be tested are prediluted in DMSO in 384-well compound dilution plates, either in an 8 or 40 sample per plate standardized dose response format. 3-fold serial dilution increments of each test compound are prepared in the plates and test samples are transferred via acoustic transfer apparatus (Echo, Labcyte) at 100 nL per well into cell culture assay 384-well plates. Each compound dilution is transferred in single or quadruplicate samples into dry assay plates, which are stored until assay is ready to go. The positive and negative controls are laid out in opposite on ends of the plate in vertical blocks (1 column).

Subsequently, an infectious mixture is prepared using an appropriate dilution of virus stock previously determined by titration with cells at a density of 50,000/mL and 20 µL/well is added to test plates w/compounds via automation (uFlow, Biotek). Each plate includes negative and positive controls (16 replicates each) to create 0% and 100% virus inhibition standards, respectively. Following the infection with RSV, testing plates are incubated for 4 days in a 37° C. cell culture incubator. After the incubation, a cell viability reagent, Cell TiterGlo (Promega, Madison, WI) is added to the assay plates, which are incubated briefly, and a luminescent readout is measured (Envision, Perkin Elmer) in all the assay plates. The RSV-induced cytopathic effect, percentage inhibition, is determined from the levels of remaining cell viability. These numbers are calculated for each tested concentration relative to the 0% and 100% inhibition controls, and the $EC_{50}$ value for each compound is determined by non-linear regression as a concentration inhibiting the RSV-induced cytopathic effect by 50%. Various potent anti-RSV tool compounds are used as positive controls for antiviral activity.

Example 17. RSV NHBE $EC_{50}$

Normal human bronchial epithelial (NHBE) cells were purchased from Lonza (Walkersville, MD, Cat #CC-2540) and cultured in Bronchial Epithelial Growth Media (BEGM) (Lonza, Walkersville, MD, Cat #CC-3170). The cells were passaged 1-2 times per week to maintain <80% confluency. The NHBE cells were discarded after 6 passages in culture.

To conduct the RSV A2 antiviral assay, NHBE cells were plated in 96-well plates at a density of 7,500 cells per well in BEGM and allowed to attach overnight at 37° C. Following attachment, 100 µL of cell culture media was removed and 3-fold serially diluted compound was added using a Hewlett-Packard D300 Digital Dispenser. The final concentration of DMSO was normalized to 0.05%. Following compound addition, the NHBE cells were infected by the addition of 100 µL of RSV A2 at a titer of $1 \times 10^{4.5}$ tissue culture infectious doses/mL in BEGM and then incubated at 37° C. for 4 days. The NHBE cells were then allowed to equilibrate to 25° C. and cell viability was determined by removing 100 µL of culture medium and adding 100 µL of Cell-Titer Glo viability reagent. The mixtures were incubated for 10 minutes at 25° C., and the luminescence signal was quantified on an Envision luminescence plate reader.

Example 18. RSV HAE $EC_{50}$

HAE cells are cultured at the air-liquid interface and have an apical side that is exposed to the air and a basal side that is in contact with the medium. Prior to experimentation, HAE were removed from their agar-based shipping packaging and were acclimated to 37° C./5% CO2 overnight in 1 ml of HAE Assay medium (AIR-100-MM, Mattek Corp). HAE were prepared for infection by washing the apical surface twice with 400 µL of PBS (either utilizing direct pipetting methods or by running each transwell through a trough containing PBS) to remove the mucus layer. Apical chambers were drained of PBS and tapped gently onto absorbent material to remove as much PBS as possible. After washing, the cells were transferred to fresh HAE maintenance media containing 4-fold serially diluted compound, delivered to the basal side of the cell monolayer, and apically infected with 100 µL of a 1:600 dilution of RSV A strain A2 1000× stock (ABI, Columbia, MD, Cat #10-124-000) in HAE assay medium for 3 hours at 37° C. in 5% CO2. The virus inoculum was removed and the apical surface of the cells was washed 3 times with PBS using either method previously described. The cells were then cultured in the presence of compound for 3 days at 37° C. Following the incubation, total RNA was extracted from the HAE cells using a MagMAX-96 Viral RNA isolation kit (Applied Biosystems, Foster City, CA, Cat #AM1836) and intracellular RSV RNA was quantified by real-time PCR. Approximately 25 ng of purified RNA was added to a PCR reaction mixture that contained 0.9 µM RSV N Forward and RSV N Reverse primers, 0.2 µM RSV N Probe and 1× Taqman RNA-to-Ct 1-Step Kit (Applied Biosystems, Foster City, CA, Cat #4392938). RNA levels were normalized using a Taqman GAPDH control primer set (Applied Biosystems, Foster City, CA, Cat #402869). Real-Time PCR Primers and Probe Used in the RSV A2 HAE Antiviral Assay: RSV N Forward CATCCAGCAAATACACCATCCA (SEQ ID NO: 2), RSV N Reverse TTCTGCACATCATAATTAG-GAGTATCAA (SEQ ID NO: 3), RSV N Probe FAM-CGGAGCACAGGAGAT-BHQ (SEQ ID NO: 4).

Example 19. HRV16 HeLa $EC_{50}$

H1-HeLa cells, cultured in complete DMEM medium containing 10% heat-inactivated FBS and 1% Penicillin/Streptomycin, were seeded in 96 well plates at 3000 cells/well one day prior to compound dosing and infection. The antiviral activity of each compound was measured in triplicate. Compounds were added directly to the cell cultures in serial 3-fold dilutions using the HP300 digital dispenser (Hewlett Packard, Palo Alto, CA) immediately prior to infection. The plates were transferred to BSL-2 containment and the appropriate dilution of virus stock, previously determined by titration and prepared in cell culture media, was added to test plates containing cells and serially diluted compounds. Each plate included 6 wells of infected untreated cells and 6 wells of uninfected cells that served as 0% and 100% virus inhibition control, respectively. Following the infection, test plates were incubated for 96 h in a tissue culture incubator set to 33° C./5% $CO_2$. Following incubation, the H1-HeLa cells were removed from incubation and allowed to equilibrate to 25° C. Cell viability was determined by removing 100 µL of culture medium and adding 100 µL of Cell-Titer Glo viability reagent. The mixtures were incubated on a shaker for 10 minutes at 25° C., and the luminescence signal was quantified on an Envision luminescence plate reader. The percentage inhibition of virus infection was calculated for each tested concentration relative to the 0% and 100% inhibition controls and the $EC_{50}$ value for each compound was determined by 4-parametric non-linear regression as the effective concentration of compound that inhibited cytopathic effect by 50%.

Example 20. HRV1A HeLa $EC_{50}$

H1-HeLa cells, cultured in complete RPMI 1640 medium containing 10% heat-inactivated FBS and 1% Penicillin/Streptomycin, were seeded in 96 well plates at 5000 cells/well one day prior to compound dosing and infection. The antiviral activity of each compound was measured in triplicate. Compounds were added directly to the cell cultures in serial 3-fold dilutions using the HP300 digital dispenser (Hewlett Packard, Palo Alto, CA) immediately prior to infection. The plates were transferred to BSL-2 containment and 100 μL of 1/4000 dilution of HRV1a virus stock was added to each well containing cells and serially diluted compounds. Each plate included 6 wells of infected untreated cells and 6 wells of cells containing 5 M Rupintrivir that served as 0% and 100% virus inhibition control, respectively. Following the infection, test plates were incubated for 96 h in a tissue culture incubator set to 37° C./5% $CO_2$. Following incubation, the H1-HeLa cells were removed from incubation and allowed to equilibrate to 25° C. Cell viability was determined by removing 100 μL of culture medium and adding 100 μL of Cell-Titer Glo viability reagent. The mixtures were incubated on a shaker for 10 minutes at 25° C., and the luminescence signal was quantified on an Envision luminescence plate reader. The percentage inhibition of virus infection was calculated for each tested concentration relative to the 0% and 100% inhibition controls and the $EC_{50}$ value for each compound was determined by 4-parametric non-linear regression as the effective concentration of compound that inhibited cytopathic effect by 50%.

Example 21. HRV14 HeLa $EC_{50}$

H1-HeLa cells, cultured in complete RPMI 1640 medium containing 10% heat-inactivated FBS and 1% Penicillin/Streptomycin, were seeded in 96 well plates at 5000 cells/well one day prior to compound dosing and infection. The antiviral activity of each compound was measured in triplicate. Compounds were added directly to the cell cultures in serial 3-fold dilutions using the HP300 digital dispenser (Hewlett Packard, Palo Alto, CA) immediately prior to infection. The plates were transferred to BSL-2 containment and 100 μL of 1/4000 dilution of HRV14 virus stock was added to each well containing cells and serially diluted compounds. Each plate included 6 wells of infected untreated cells and 6 wells of cells containing 5 M Rupintrivir that served as 0% and 100% virus inhibition control, respectively. Following the infection, test plates were incubated for 96 h in a tissue culture incubator set to 37° C./5% $CO_2$. Following incubation, the H1-HeLa cells were removed from incubation and allowed to equilibrate to 25° C. Cell viability was determined by removing 100 μL of culture medium and adding 100 μL of Cell-Titer Glo viability reagent. The mixtures were incubated on a shaker for 10 minutes at 25° C., and the luminescence signal was quantified on an Envision luminescence plate reader. The percentage inhibition of virus infection was calculated for each tested concentration relative to the 0% and 100% inhibition controls and the $EC_{50}$ value for each compound was determined by 4-parametric non-linear regression as the effective concentration of compound that inhibited cytopathic effect by 50%.

Example 22. HRVc15 and HRVc25 HeLa $EC_{50}$

First, HRV replicon RNA is prepared. 5ug of DNA Template (HRVc15 or HRVc25) is linearized with 2 μL of MluI enzyme in NEB buffer-3 in a final volume of 25 μL for 3 hours at 37° C. Following incubation, linearized DNA is purified on a PCR purification column and the following in vitro transcription is performed using the following conditions: 10 μL of RiboMAX Express T7 2× buffer, 1-8 μL of linear DNA template (1 μg), 0-7 μL nuclease free water, 2 μL enzyme mix T7 express. The final volume of 20 μL is mixed and incubated at 37° C. for 30 min. Following incubation, 1 μL of RQ1 RNase free DNase is added and the mixture is incubated at 37° C. for 15 min. The resulting RNA is then purified with the MegaClear Kit (Gibco Life Technologies Cat #11835-030) and is eluted two times with 50 μL of elution buffer at 95° C. H1-HeLa cells cultured in complete RPMI 1640 media containing 10% heat-inactivated FBS and 1% Penicillin/Streptomycin are seeded into T-225 flasks at a concentration of 2E6 cells/flask a day prior to transfection and are incubated at 37° C./5% $CO_2$ overnight. On the day of transfection, cells are trypsinized following standard cell culture protocols and are washed two times with PBS. Following washes, cells are resuspended at a concentration of 1E7 cells/mL in PBS and the suspension is stored on wet ice. Electroporation is used to introduce replicon RNA into the H1-HeLa cells. A final volume of 10 μL containing 10 μg of replicon c15 or 1 μg of c25 replicon RNA, respectively, are pipetted into a 4 mm electroporation cuvette. The H1-HeLa cell stock is mixed by gently swirling and 0.5 mL of the cell stock previously prepared is transferred into the cuvette containing the replicon RNA. The combined solution is flicked to mix. Following mixing, cells are immediately electroporated using the following settings: 900V, 25 uF, infinite resistance, 1 pulse. Cuvettes are rested on ice for 10 min. Following the 10 min incubation, add 19 mL of ambient temperature, phenol red-free and antiobiotic-free RPMI 1640 containing 10% heat-inactivated FBS per electroporation. 150 μL (4E4 cells) of the electroporated cell suspension are seeded per well into a 96 well clear-bottom, white cell culture plate, and are incubated at 25° C. for 30 min. Compounds were added directly to the cell cultures in serial 3-fold dilutions using the HP300 digital dispenser (Hewlett Packard, Palo Alto, CA) and were tested in triplicate. Following the addition of compounds, plates are incubated at 33° C. for 48 hrs. Replicon activity is then measured by a Renilla-Glo Luciferase Assay system. Prior to signal quantification, plates are removed from incubators and are allowed to equilibrate to 25° C. after 50 uL is removed from each well. Following manufacturer's protocol, a 1:100 dilution of *Renilla*-Glo substrate to buffer is prepared and 100 uL of the Renill-Glo luciferase mix is added to each well. Plates are then incubated for 20 min at 25° C. under gentle agitation and luciferase signal are determined with a 0.1 second detection setting using an EnVision luciferase quantification reader. The percentage inhibition of replicon inhibition was calculated for each tested concentration relative to the 0% and 100% inhibition controls included in the experiments and the $EC_{50}$ value for each compound was determined by 4-parametric non-linear regression as the effective concentration of compound that inhibited luciferase signal by 50%.

Example 23. HCV Rep 1B and 2A $EC_{50}$ and $CC_{50}$

Compounds were serially diluted in ten steps of 1:3 dilutions in 384-well plates. All serial dilutions were performed in four replicates per compound within the same 384-well plate. An HCV protease inhibitor ITMN-191 at 100 µM was added as a control of 100% inhibition of HCV replication while puromycin at 10 mM was included as a control of 100% cytotoxicity. To each well of a black polystyrene 384-well plate (Greiner Bio-one, Monroe, NC), 90 µL of cell culture medium (without Geneticin) containing 2000 suspended HCV replicon cells was added with a Biotek Flow workstation. For compound transfer into cell culture plates, 0.4 µL of compound solution from the compound serial dilution plate was transferred to the cell culture plate on a Biomek FX workstation. The DMSO concentration in the final assay wells was 0.44%. The plates were incubated for 3 days at 37° C. with 5% $CO_2$ and 85% humidity. The HCV replicon assay was a multiplex assay, able to assess both cytotoxicity and antireplicon activity from the same well. The $CC_{50}$ assay was performed first. The media in the 384-well cell culture plate was aspirated, and the wells were washed four times with 100 µL of PBS each, using a Biotek ELX405 plate washer. A volume of 50 µL of a solution containing 400 nM calcein AM (Anaspec, Fremont, CA) in 1×PBS was added to each well of the plate with a Biotek Flow workstation. The plate was incubated for 30 min at room temperature before the fluorescence signal (excitation 490 nm, emission 520 nm) was measured with a Perkin-Elmer Envision plate reader. The $EC_{50}$ assay was performed in the same wells as the $CC_{50}$ assay. The calcein-PBS solution in the 384-well cell culture plate was aspirated with a Biotek ELX405 plate washer. A volume of 20 µL of Dual-Glo luciferase buffer (Promega, Madison, WI) was added to each well of the plate with a Biotek Flow Workstation. The plate was incubated for 10 min at room temperature. A volume of 20 µL of a solution containing a 1:100 mixture of Dual-Glo Stop & Glo substrate (Promega, Madison, WI) and Dual-Glo Stop & Glo buffer (Promega, Madison, WI) was added to each well of the plate with a Biotek Flow Workstation. The plate was then incubated at room temperature for 10 min before the luminescence signal was measured with a Perkin-Elmer Envision Plate Reader.

Example 24. Inhibition of Human Mitochondrial RNA Polymerase (POLRMT)

All reaction mixtures contained 50 mM Tris-HCl buffer (pH 8.0), 0.2 mg/ml BSA, 2 mM DTT, 0.05 mg/ml activated fish sperm DNA, 10 mM MgCl2, 1.3 µCi [$\alpha$-$^{33}$P]dTTP (3,000 Ci/mmol), and 2 µM each of dATP, dGTP, and TTP. The optimal enzyme concentrations were chosen to be in the linear range of enzyme concentration ([E]) versus activity, and the reaction time was selected to ensure that 10% of the substrate was consumed. All reactions were run at 37° C. The inhibition of mitochondrial RNA polymerase (POLRMT) was evaluated using 20 nM POLRMT preincubated with 20 nM template plasmid (pUC18-LSP) containing POLRMT light-strand promoter region and mitochondrial transcription factor A (mtTFA) (100 nM) and mt-TFB2 (20 nM) in buffer containing 10 mM HEPES (pH 7.5), 20 mM NaCl, 10 mM DTT, 0.1 mg/ml BSA, and 10 mM $MgCl_2$. The reactions were heated to 32° C. and initiated by adding 2.5 µM each of the four natural NTPs and 1.5 µCi of [$^{33}$P]GTP. After incubation for 30 min at 32° C., the reactions were spotted on DE81 paper before being processed for quantification.

Example 25. Single Nucleotide Incorporation by Human Mitochondrial RNA Polymerase (POLRMT)

A mixture of MTCN buffer (50 mM MES, 25 mM Tris-HCl, 25 mM CAPS, and 50 mM NaCl, pH 7.5), 200 nM 5'-$^{32}$P-R12/D18, 10 mM $MgCl_2$, 1 mM DTT, and 376 nM POLRMT was preincubated at 30° C. for 1 min. The reaction was started by addition of 500 µM (final) natural NTP or NTP analogs. At selected time points, the reaction mixture was removed and quenched with gel loading buffer containing 100 mM EDTA, 80% formamide, and bromophenol blue, and heated at 65° C. for 5 min. The samples were run on a 20% polyacrylamide gel (8 M urea), and the product formation was quantified using Typhoon Trio Imager and Image Quant TL Software (GE Healthcare, Piscataway, NJ). The rate of single nucleotide incorporation by mt RNA pol was calculated by fitting the product formation using the single exponential equation: $[R13]=A(1-e^{-kt})$, where [R13] represents the amount (in nM) of the elongated product formed, t represents the reaction time, k represents the observed rate, and A represents the amplitude of the exponential.

TABLE 2

Activity of the compound of Formula I against RSV and HRV.

| RSV HEp-2 $EC_{50}$ | RSV NHBE $EC_{50}$ | RSV HAE $EC_{50}$ | HRV16 HeLa $EC_{50}$ | HRV1A HeLa $EC_{50}$ | HRV14 HeLa $EC_{50}$ | HRV15 Rep $EC_{50}$ | HRV25 Rep $EC_{50}$ |
|---|---|---|---|---|---|---|---|
| 88 | 124 | 23 | 227 | 8 | 78 | 9 | 7 |

All values in nM.

TABLE 3

Activity of the compound of Formula I against dengue virus.

| DENV Huh7 $EC_{50}$ | DENV Huh7 REP $EC_{50}$ | DENV moDC $EC_{50}$ |
|---|---|---|
| 1633 | 2937 | >6194 |

All values in nM.

TABLE 4

Activity of the compound of Formula I against HCV.

| HCV Rep 1B $EC_{50}$ | HCV Rep 2A $EC_{50}$ |
|---|---|
| 793 | 1268 |

All values in nM

TABLE 5

Comparative RSV potency of the compound of Formula I and compounds 1 and 2.

| Compound | RSV Hep2-384 $EC_{50}$ | RSV NHBE $EC_{50}$ | RSV HAE $EC_{50}$ |
|---|---|---|---|
| Formula I | 88 | 124 | 23 |
| 1 | 352 | 549 | — |
| 2 | 69 | 75 | 186 |

All values in nM.

TABLE 6

Comparative HRV potency of the compound of Formula I and compounds 1 and 2.

| Compound | HRV16 HeLa $EC_{50}$ | HRV1A HeLa $EC_{50}$ | HRV14 HeLa $EC_{50}$ | HRV15 Rep $EC_{50}$ | HRV25 Rep $EC_{50}$ |
|---|---|---|---|---|---|
| Formula I | 227 | 8 | 78 | 9 | 7 |
| 1 | 959 | 409 | 1000 | — | — |
| 2 | 164 | 97 | 171 | 21 | — |

All values in nM.

TABLE 7

Comparative dengue and HCV potency of the compound of Formula I and compounds 1 and 2.

| Compound | DENV huh7 Rep $EC_{50}$ | HCV Rep 1B $EC_{50}$ | HCV Rep 2A $EC_{50}$ |
|---|---|---|---|
| Formula I | 2937 | 793 | 1268 |
| 1 | 73429 | — | — |
| 2 | 5535 | 2776 | 1826 |

All values in nM.

As seen in Tables 5-7, the compound of Formula I is more potent in RSV antiviral assays (Hep-2 and NHBE) relative to the compound 1 (about 4.0 and 4.4 more potent respectively). The compound of Formula I is also more potent against HRV (in HRV16 HeLa, HRV1A HeLa, and HRV14 HeLa assays) relative to the compound 1 (about 4.2, 51.1, and 12.8 times more potent respectively). Likewise, the compound of Formula I is more potent against dengue (in Denv huh7 Rep assay) than the compound 1 (about 25.0 times more potent).

Similarly, the compound of Formula I also exhibits higher anti-RSV activity relative to the compound 2 in the HAE assay (Mirabelli, C. et al J. Antimicrob. Chemother. 2018, 73, 1823-1829) (about 8.1 times more potent). The compound of Formula I is also more potent in multiple HRV antiviral assays (in HRV1A HeLa, HRV14 HeLa, and HRV15 Rep assays) compared to the compound 2 (about 12.1 times more potent in HRV1A HeLa assay, about 2.2 times more potent in HRV14 HeLa assay, and about 2.3 times more potent in HRV15 Rep assays). The compound of Formula I is additionally more potent in a dengue antiviral assay (about 1.9 times more potent in DENV huh7 Rep assay). Likewise, the compound of Formula I is more potent relative to compound 2 in HCV antiviral assays (about 3.5 times in HCV Rep 1B and 1.4 times in HCV Rep 2A).

Example 26. RSV Potency of the Compound of Formula I in Comparison to Structurally Related Compounds 3-5

The compound of Formula I is characterized by, among other things, a cyclohexyl group at the ester group (position indicated by an * in the structure below).

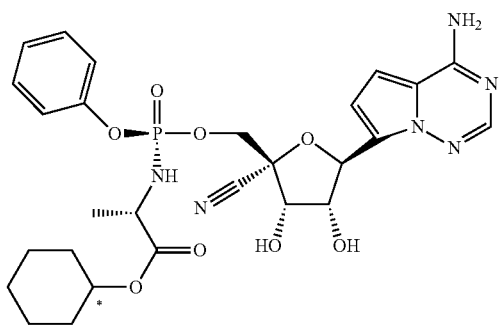

Formula I

The potency of the compound of Formula I and compounds 3-5 (structures shown below) was measured according to the assays described above. The structures of compounds 3-5 are comparable to the compound of Formula I, except that they lack a cyclic ring at the branched ester (position indicated by an * in the structures below). The results of these experiments are summarized in the Table 8 below.

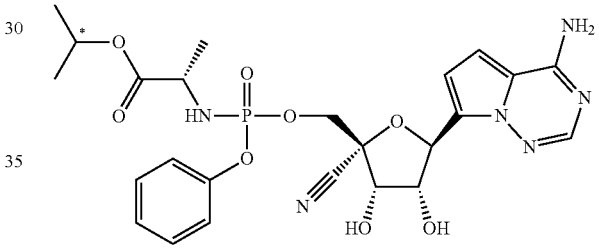

3

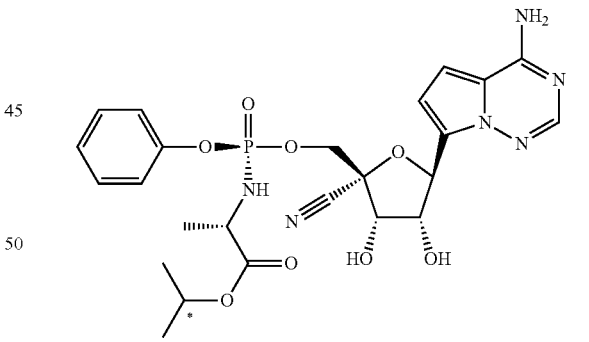

4

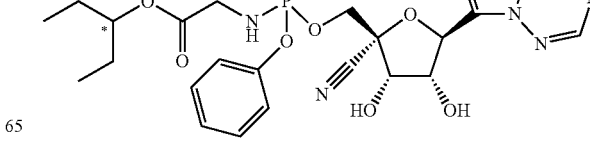

5

TABLE 8

RSV comparative potency of the compound of Formula I and compounds 1-3.

| Compound | RSV Hep-2 EC$_{50}$ | RSV NHBE EC$_{50}$ | HRV16 HeLa EC$_{50}$ | HRV1A HeLa EC$_{50}$ | HRV14 HeLa EC$_{50}$ |
|---|---|---|---|---|---|
| Formula I | 88 | 124 | 227 | 8 | 78 |
| 3 | 463 | 1150 | 1418 | 735 | 1807 |
| 4 | 342 | 879 | 965 | — | — |
| 5 | 1744 | 1239 | 3128 | 1625 (n = 1) | 3431 (n = 1) |

All values in nM.

As seen, in the Table 8 above, the compound of Formula I is more potent in RSV and HRV antiviral assays relative to the compounds 3 (about 5 times in RSV Hep-2 assay, about 9.3 times in RSV NHBE assay, about 6.2 times in HRV16 HeLa assay, about 91.9 times in HRV1A HeLa assay, and about 23.2 times in HRV14 HeLa assay), 4 (about 3.9 times in RSV Hep-2 assay, about 7.1 times in RSV NHBE assay, about 4.3 times in HRV16 Hela assay), and 5 (about 19.8 times in RSV Hep-2 assay, about 10.0 times in RSV NHBE assay, about 13.8 times in HRV16 HeLa assay, about 203.1 times in HRV1A HeLa assay, and about 44.0 times in HRV14 HeLa assay), each of which lack the cyclic cyclohexyl group at the branched ester. Accordingly, the compound of Formula I exhibits improved properties as compared to compounds 3-5, having a branched alkyl group, but lacking the cyclohexyl group, at the ester group.

Example 27. Potency of the Compound of Formula I in Comparison to the Compounds of Formula Ia, Formula Ib, and Compounds 2, 6, 7, and 8

The potency of the compound of Formula I, as well as structurally related compounds of Formula Ia and Formula Ib, and compounds 2, 6, 7, and 8 was measured according to the assays described above. The structures of the compounds of Formula Ia, Formula Ib, 6, 7, and 8 are shown below and the results are summarized in the Table 9 below.

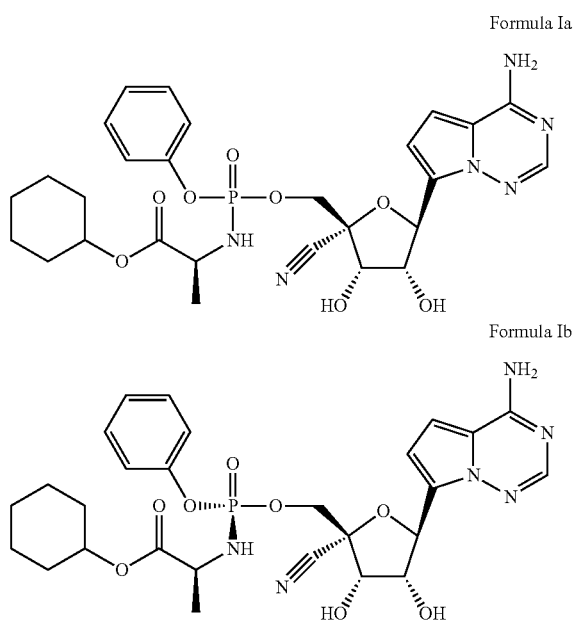

Formula Ia

Formula Ib

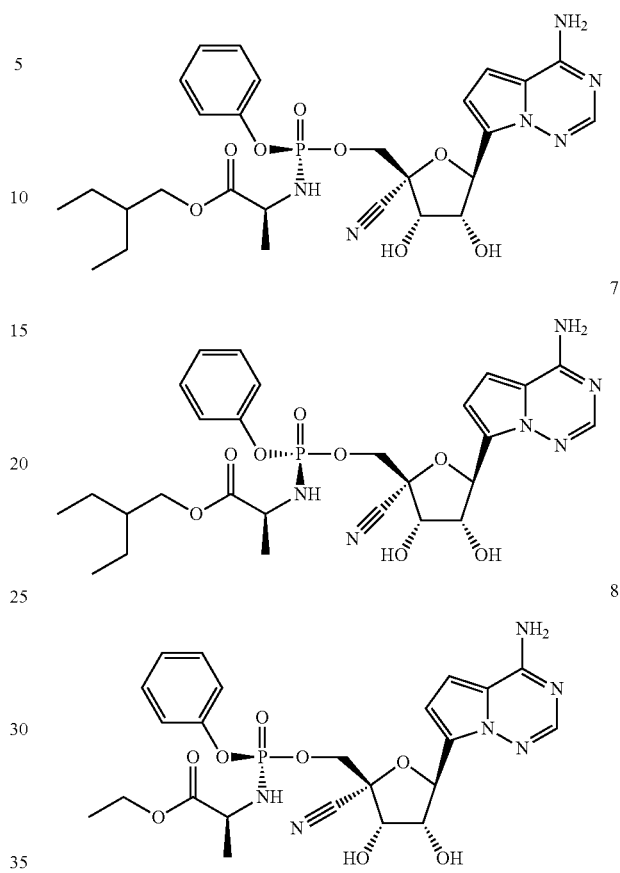

6

7

8

TABLE 9

RSV and HRV comparative potency of the compound of Formula I, Formula Ia, Formula Ib, and compounds 2, 6, 7, and 8.

| Compound | P Stereochemistry | RSV HEp-2 EC$_{50}$ | RSV NHBE EC$_{50}$ | RSV HAE EC$_{50}$ | HRV16 HeLa EC$_{50}$ | HRVc15 Rep EC$_{50}$ |
|---|---|---|---|---|---|---|
| Formula Ia | mix | 96 | 76 | | 510 | |
| Formula I | S | 88 | 124 | 23 | 227 | 9 |
| Formula Ib | R | 2735 | 630 | | 654 | |
| 2 | mix | 69 | 75 | 186 | 164 | 21 |
| 6 | S | 26 | 127 | 110 | 135 | 17 |
| 7 | R | 124 | 91 | | 183 | |
| 8 | S | 91 | 932 | | 678 | |

All values in nM.

The EC$_{50}$ data in Table 9 above shows that the compound of Formula I, with S stereochemistry at the P, is significantly more potent than the compound of Formula Ib, which has an R stereocenter at the P, in both RSV and HRV assays. Specifically, the compound of Formula I is 31.1 times more potent than the compound of Formula Ib in RSV HEp-2 assay and 5.1 more potent in RSV NHBE assay. Likewise, the compound of Formula I is 2.9 times more potent than the compound of Formula Ib in HRV16 HeLa assay.

By contrast, the potency of compounds 6 and 7, which also differ only in the stereochemistry at the P (compound 6 has S and compound 7 has R stereochemistry at the P), are not as differentiated as compounds of Formula I and Formula Ib. Compound 6 is only 4.8 times more potent than compound 7 in RSV HEp-2 assay and 1.4 times more potent in in HRV16 HeLa assay. In RSV NHBE assay, the compound 6 is only 0.7 times as potent as compound 7.

Example 28. HEp-2 and MT-4 Cytotoxicity Assays

Cytotoxicity of the compound of Formula I and compounds 1, 2, and 6 was determined in uninfected cells using the cell viability reagent in a similar fashion as described before for other cell types (Cihlar et al., Antimicrob Agents Chemother. 2008, 52(2):655-65.). HEp-2 (1.5 ×103 cells/well) and MT-4 (2×103 cells/well) cells were plated in 384-well plates and incubated with the appropriate medium containing 3-fold serially diluted compound ranging from 15 nM to 100,000 nM. Cells were cultured for 4-5 days at 37° C. Following the incubation, the cells were allowed to equilibrate to 25° C., and cell viability was determined by adding Cell-Titer Glo viability reagent. The mixture was incubated for 10 min, and the luminescence signal was quantified using an Envision plate reader. Untreated cell and cells treated at 2 μM puromycin (Sigma, St. Louis, MO) serve as 100% and 0% cell viability control, respectively. The percent of cell viability was calculated for each tested compound concentration relative to the 0% and 100% controls and the $CC_{50}$ value was determined by non-linear regression as a compound concentration reducing the cell viability by 50%.

Example 29. NHBE and SAEC Cytotoxicity Assays

Normal human bronchial epithelial (NHBE) cells were purchased from Lonza (Walkersville, MD, Cat #CC-2540) and cultured in Bronchial Epithelial Growth Media (BEGM) (Lonza, Walkersville, MD, Cat #CC-3170). The cells were passaged 1-2 times per week to maintain <80% confluency per manufacturer's protocol. The NHBE cells were discarded after 5 passages in culture.

Human Small Airway Epithelial cells (SAEC) were purchased from Lonza (Walkersville, MD, Cat #CC-2547) and cultured in supplemented Small Airway Epithelial Cell Growth Medium (SAGM) (lonza, Walkersville, MD, Cat #CC-3118). The cells were passaged 1-2 times per week to maintain <80% confluency per manufacturer's protocol. The SAEC cells were discarded after 5 passages in culture.

To determine the 50% cytotoxic concentration ($CC_{50}$) of the compound of Formula I and compounds 1, 2 and 6, NHBE or SAEC cells were plated in clear bottom, black-walled 96-well plates at a density of 10,000 cells per well in 200 μL BEGM or SAGM and allowed to attach overnight at 37° C. Following attachment, 3-fold serially diluted compound was added using a Hewlett-Packard D300 Digital Dispenser (Hewlett Packard, Palo Alto, CA) in triplicate. The final concentration of DMSO was normalized to 1.0%. Following compound addition, NHBE or SAEC cells were incubated at 37° C. for 5 days. The NHBE or SAEC cells were then allowed to equilibrate to 25° C. and cell viability was determined by removing 100 μL of culture medium and adding 100 μL of Cell-Titer Glo viability reagent (Promega, Madison, WI). The mixtures were incubated for 10 minutes at 25° C., and the luminescence signal was quantified on an Envision luminescence plate reader (PerkinElmer, Waltham, MA). Percent viability values were determined by normalization to 1.0% DMSO-only control wells with background luminescent signal subtracted out.

Example 30. PHH Cytotoxicity Assay

Three-fold serial dilutions of the compound of Formula I and compounds 1, 2 and 6 were prepared in duplicate in 96-well plates starting at a concentration of 50 or 100 μM. Fresh human hepatocytes were ordered in a 96-well plate format from BioIVT (Baltimore, Maryland, Cat #F/M91565) with a Matrigel overlay or Invitrogen (Durham, North Carolina, Cat #HMFY96) with a Geltrex overlay. Donor profiles were limited to 4-65-year old with minimal alcohol consumption. PHH cells were allowed to recover 4-24 hours in complete medium with added supplement supplied by the vendor at 37° C. in a 5% $CO_2$ incubator with 90% humidity before treated with compounds. Serial-diluted compounds and complete medium were replaced (130 μL/well) daily for 5 days, with final amount of DMSO equal to 0.5%. On Day 5, medium was removed from the assay plates and cell viability was determined by the addition of 100 μL Cell-Titer Glo viability reagents (Promega, Madison, WI, Cat #G7573) added to each well. Following 5-10 minutes incubation at room temperature, luminescence signal was quantified on a Victor Luminescence plate reader (Perkin-Elmer, Waltham, MA).

Example 31. PRPT Cytotoxicity Assay

The PRPT cytotoxicity assays on the compound of Formula I and compounds 1, 2 and 6 were conducted using the following protocol.

Cryopreserved human primary renal proximal tubule epithelial cells (PRPTEC), were obtained from LifeLine Cell Technology (Frederick, MD, Cat #FC-0013) and isolated from the tissue of human kidney. The cells were cultured with RenaLife completed medium (LifeLine, Frederick, MD, Cat #LL-0025) in T75 flask for 3 to 4 days from cryopreserved vial, before the cells were seeded to assay plates after 90% confluence. PRPTEC cells were plated at a density of 5×103 cells per well in collagen coated 96-well plate with a final volume of 160 mL per well. On next day, the compound was added to cell plates directly using HP D300 Dispenser (Hewlett-Packard, Palo Alto, CA) with program starting at 200 fold lower than the compound stock concentration, and 1:3 fold dilution in duplicates with constant amount of DMSO equal to 0.5%. After 5-day incubation, culture medium was removed, cell viability was measured by addition of 100 mL per well of CellTiter Glo viability reagent (Promega, Madison, WI, Cat #G7573) and the luminescence signal was quantified on a Luminescence plate reader (Perkin-Elmer, Waltham, MA).

Example 32. GALHEPG2 Cytotoxicity Assay

The compound of Formula I and compounds 1, 2 and 6 were tested in a high-throughput 384-well assay format for cytotoxicity in galactose-adapted HepG2 cells (human liver carcinoma cell line).

Cells were diluted in media (DMEM (11966), 10% FBS, 1% NEAA, 0.2% Galactose, 1% Pyruvate, 1% Glutamax, 1% PSG) to 16.6K cells/mL and plated at 90 uL/well into 384 well poly-D-lysine coated assay plates and placed in an incubator at 37° C. and 5% CO2. Compounds were serially diluted (1:3) in 100% DMSO in 384-well plates in quadruplicate. DMSO and 2 mM Puromycin were included as negative and positive controls respectively. 24 hours after cell plating, a 384 channel pipettor was used to transfer 0.4 uL from the compound plate to the assay plate. Assay plates were returned to the incubator. After 5 days, assay plates were washed with 80 uL/well of PBS before addition of 20 uL of Cell Titer Glo. Assay plates were read on the Envision plate reader. $CC_{50}$ values were defined as the compound concentration that results in 50% inhibition of growth, as

Example 33. GALPC3 Cytotoxicity Assay

Compounds were tested in a high-throughput 384-well assay format for cytotoxicity in galactose-adapted PC3 cells (human prostate cancer cell line). Cells were diluted in media (DMEM (11966), 10% FBS, 1% NEAA, 0.2% Galactose, 1% Pyruvate, 1% Glutamax, 1% PSG) to 16.6K cells/mL and plated at 90 uL/well into 384 well poly-D-lysine coated assay plates and placed in an incubator at 37° C. and 5% $CO_2$. Compounds were serially diluted (1:3) in 100% DMSO in 384-well plates in quadruplicate. DMSO and 2 mM Puromycin were included as negative and positive controls respectively. 24 hours after cell plating, a 384 channel pipettor was used to transfer 0.4 uL from the compound plate to the assay plate. Assay plates are returned to the incubator. After 5 days, assay plates are washed with 80 uL/well of PBS before addition of 20 uL of Cell Titer Glo. Assay plates are read on the Envision plate reader. $CC_{50}$ values are defined as the compound concentration that results in 50% inhibition of growth, as measured in luminescence signal. $CC_{50}$ values were calculated in Accord (on-line tool) using a one-site dose-response model to generate sigmoidal curve fits.

Example 34. Huh-7 Cytotoxicity Assay

Compounds were tested in a high-throughput 384-well assay format for cytotoxicity in Huh7 cells (Hepatocarcinoma cell line). Cells were diluted in media (DMEM (15-018-CM), 10% FBS, 1% NEAA, 1% PSG) to 16.6K cells/mL and plated at 90 uL/well into 384 well poly-D-lysine coated assay plates and placed in an incubator at 37° C. and 5% CO2. Compounds were serially diluted (1:3) in 100% DMSO in 384-well plates in quadruplicate. DMSO and 2 mM Puromycin were included as negative and positive controls respectively. 24 hours after cell plating, a 384 channel pipettor was used to transfer 0.4 uL from the compound plate to the assay plate. Assay plates were returned to the incubator. After 5 days, assay plates were washed with 80 uL/well of PBS before addition of 20 uL of Cell Titer Glo. Assay plates were read on the Envision plate reader. $CC_{50}$ values were defined as the compound concentration that results in 50% inhibition of growth, as measured in luminescence signal. $CC_{50}$ values were calculated in Accord (on-line tool) using a one-site dose-response model to generate sigmoidal curve fits.

Example 35. MRC5 Cytotoxicity Assay

Compounds were tested in a high-throughput 384-well assay format for cytotoxicity in MRC5 cells (human fetal lung fibroblast cell line). Cells were diluted in media (MEM (10-010-CM), 10% FBS, 1% PSG) to 16.6K cells/mL and plated at 90 uL/well into 384 well poly-D-lysine coated assay plates and placed in an incubator at 37° C. and 5% $CO_2$. Compounds were serially diluted (1:3) in 100% DMSO in 384-well plates in quadruplicate. DMSO and 2 mM Puromycin were included as negative and positive controls respectively. 24 hours after cell plating, a 384 channel pipettor was used to transfer 0.4 uL from the compound plate to the assay plate. Assay plates were returned to the incubator. After 5 days, assay plates were washed with 80 uL/well of PBS before addition of 20 uL of Cell Titer Glo. Assay plates were read on the Envision plate reader. $CC_{50}$ values were defined as the compound concentration that results in 50% inhibition of growth, as measured in luminescence signal. $CC_{50}$ values were calculated in Accord (on-line tool) using a one-site dose-response model to generate sigmoidal curve fits.

Example 36. NRVM Neonatal Rat Cardiomyocyte Cytotoxicity Assay

Compounds were tested in a high-throughput 384-well assay format for cytotoxicity against freshly harvested neonatal rat cardiomyocytes (NRVM). Cells were diluted in media (DMEM+10% FBS+1% PSG+1% NEAA) to 25,000 cells/mL, plated at 90 ul per well in 384 well cell assay plates and incubated overnight at 37° C. and 5% $CO_2$ before compound addition. Compounds were prepared by serial dilution (1:3) in 100% DMSO in 384-well plates in quadruplicate. 400 nL/well of compound were transferred into cell assay plates via Biocel (Agilent Technologies). DMSO and 2 mM Puromycin were included as negative and positive controls respectively. After 5 days, plates are washed 1× w/100 ul/well PBS with Biotek plate washer, and 20 uL of Cell Titer Glo was added to each well. Plates were incubated 10 min and read on EnVision reader (Perkin Elmer). $CC_{50}$ values were defined as the compound concentration that results in 50% inhibition of growth, as measured in luminescence signal. $CC_{50}$ values were calculated in Accord (on-line tool) using a one-site dose-response model to generate sigmoidal curve fits.

Example 37. PBMC Cytotoxicity Assay

Compounds were tested in a high-throughput 384-well assay format for cytotoxicity in cryopreserved human PBMCs. Compounds were serially diluted (1:3) in 100% DMSO in 384-well plates in quadruplicate. An acoustic dispenser was used to transfer 310 nL of compound into assay plates. DMSO and 2 mM Puromycin were included as negative and positive controls respectively. Cells were diluted in media (RPMI+10% FBS+1% PSG+10 mM Hepes+1% Pyruvate+0.1% BMe) to 72K cells/mL and allowed to rest for 4 hours in an incubator at 37° C. and 5% $CO_2$ before plating into prespotted assay plates at 70 uL/well. After 5 days, 25 uL of Cell Titer Glo was added to the assay plates. $CC_{50}$ values were defined as the compound concentration that results in 50% inhibition of growth, as measured in luminescence signal. $CC_{50}$ values were calculated in Accord (on-line tool) using a one-site dose-response model to generate sigmoidal curve fits.

TABLE 10

Comparative cytotoxicity of the compound of Formula I and compounds 1, 2, 6, and 8

| Comp. | $CC_{50}$ HEp-2 | $CC_{50}$ MT4 | $CC_{50}$ NHBE | $CC_{50}$ SAEC | $CC_{50}$ GALHEPG2 | $CC_{50}$ GALPC3 |
|---|---|---|---|---|---|---|
| Formula I | >100000 | 56212.2 | >40088.3 | 122900 | >88888.9 | >44444.4 |
| 1 | >91486.2 | 52373.7 | >50000 | — | >44444.4 | — |
| 2 | >95436.2 | >43709.5 | 29105.2 | 28300 | >44444.4 | — |

TABLE 10-continued

Comparative cytoxicity of the compound of Formula I and compounds 1, 2, 6, and 8

| | | | | | |
|---|---|---|---|---|---|
| 6 | >94960.5 | 38830.1 | 24378 | 27200 | >88888.9 | >83510.8 |
| 8 | >100000 | 28291.4 | | | | |

| Comp. | $CC_{50}$ HUH7 | $CC_{50}$ MRC5 | $CC_{50}$ NRVM | $CC_{50}$ PBMC | $CC_{50}$ PHH | $CC_{50}$ PRPT |
|---|---|---|---|---|---|---|
| Formula I | >88888.9 | >44444.4 | 27728.8 | >31555.2 | 21170.5 | >84410.1 |
| 1 | >44444.4 | >44444.4 | >44444.4 | 18171.6 | — | — |
| 2 | >44444.4 | >44444.4 | >44444.4 | 4648.39 | — | 23799.4 |
| 6 | 17193.7 | >88351.4 | 8094.81 | 4790.88 | 14057.3 | 42263.7 |
| 8 | | | | | | |

All values in nM.

The above Table indicates that the compound of Formula I exhibits a better secondary cytotoxicity profile across multiple cell lines (NHBE, SAEC, Huh-7, NRVM, PBMC, PHH, and PRPT) compared to compounds 1, 2, 6, and 8.

Example 38. Plasma Stability Assay

For plasma stability, the compounds were incubated at 2 µM in cynomolgus monkey or human plasma for up to 4 h at 37° C. At desired time points, an aliquot from the incubation was quenched by addition of 9 volumes of 100% acetonitrile supplemented with internal standard. Following the last collection, samples were centrifuged at 3000 g for 30 min and supernatants were transferred to a new plate containing an equal volume of water for analysis by liquid chromatography coupled to triple quadrupole mass spectrometry (LC-MS/MS). Data (analyte to internal standard peak area ratio) were plotted on a semi log scale and fitted using an exponential fit. The half-life ($T_{1/2}$) was determined assuming first order kinetics.

Example 39. Stability Assay in S9 Fractions

For S9 stability, the compounds were incubated at 2 µM in cynomolgus monkey or human hepatic S9 fractions for up to 90 min at 37° C. in the presence of NADPH and UDPGA (Phase I and Phase II cofactor, Sigma-Aldrich). At desired time points following compound addition, samples were quenched with 9 volumes of an aqueous solution containing internal standard, 50% acetonitrile and 25% methanol. Sample plates were centrifuged at 3000 g for 30 min, and 10 µL of the resulting solution was analyzed by LC-MS/MS. Data (analyte to internal standard peak area ratio) were plotted on a semi log scale and fitted using an exponential fit. The half-life ($T_{1/2}$) was determined assuming first order kinetics.

TABLE 11

Stability (HepS9 and plasma) of the compound of Formula I in comparison to compounds 1, 2, 6, 7, and 8.

| Compound | Hum HepS9 $t_{1/2}$ (min) | Cyno HepS9 $t_{1/2}$ (min) | Hum Plasma $t_{1/2}$ (min) | Cyno Plasma $t_{1/2}$ (min) |
|---|---|---|---|---|
| Formula I | 31 | 26 | 483 | 444 |
| 1 | 12 | — | 667 | — |
| 8 | 2 | — | 361 | — |
| 2 | 12 | 3 | 152 | 289 |
| 6 | 7 | 2 | 131 | 257 |
| 7 | 6 | 2 | 233 | 178 |

The data in the above Table shows that the compound of Formula I has a higher half-life (human and cyno hepS9 as well as human and cyno plasma) than the compounds of, 2, 6, and 7.

Example 40. Thermodynamic Solubility Assay

The thermodynamic solubility of compounds were determined at room temperature in phosphate buffered saline solution (pH 7.4) and 10 mM hydrochloric acid (pH 2.0). Excess solid compound was used to saturate aqueous samples of the compounds. The tubes were placed on an agitator set at 1000 rpm and remained under constant agitation for four days. Following agitation, it was confirmed that excess solids were present in all tubes. The tubes were centrifuged at 10,000 rpm for 5 minutes to remove excess solids and the supernatant was transferred to a new vial. Concentration analysis was determined by UPLC and quantified against internal standards.

TABLE 12

Thermodynamic solubility of the compound of Formula I and compounds 5 and 6.

| Compound | pH 2 Solubility (µg/mL) | pH 7 Solubility (µg/mL) |
|---|---|---|
| Formula I | 4115 | 131 |
| 2 | 3720 | 18 |
| 6 | 3793 | 16 |

As seen in the Table above, the compound of Formula I has a higher solubility, both at pH 2 and 7, than compounds 2 and 6.

Example 41. NHBE In-Vitro Intracellular Triphosphate Formation

In-vitro intracellular triphosphate formation was measured for the compound of Formula I and compound 6 using the following protocol. Normal human bronchial airway epithelial cells (NHBEs) (0.25 million cells/well) were continuously incubated with 10 µM of compound for 26 hours. At select time points (2, 4, 6, and 26 h), the extracellular medium was removed from the well and the cells were washed twice with 2 mL of ice-cold 0.9% normal saline and extracted into 0.5 mL ice-cold 70% methanol containing 100 nM 2-chloro-adenosine-5'-triphosphate (Sigma-Aldrich, St. Louis, MO) as an internal standard. Samples were stored overnight at −20° C. to facilitate nucleotide extraction, centrifuged at 15,000×g for 15 minutes and then supernatant was transferred to clean tubes for drying in a MiVac Duo concentrator (Genevac, Gardiner, NY). Dried samples were then reconstituted in mobile phase A containing 3 mM ammonium formate (pH 5.0) with 10 mM dimethylhexylamine (DMHA) in water for analysis by LC-MS/MS. The results of these experiments are shown in FIG. 1.

Example 42. PBMC In-Vitro Intracellular Triphosphate Formation Assay

In-vitro intracellular triphosphate formation was measured for the compound of Formula I and compounds 2 and 6 using the following protocol. Freshly-isolated PBMC's were derived from a healthy donor and were suspended to a concentration of 5 million cells/mL in culture medium (RPMI 1164 containing L-glutaimine) prior to the start of the experiment. 10 mL aliquots of PBMCs were transferred to 50 mL conical tubes with loosened caps and compounds were added to a final concentration of 2 µM. 1 mL aliquots were then transferred to the wells of a 24-well plate per sample. The PBMC-compound mixtures were incubated for 2 hours at 37° c./5% $CO_2$ under gentle agitation. Following incubation, PBMCs were spun at 5000 RPM for 3 min and supernatants were aspirated without disturbing the cell pellet. For samples undergoing immediate analysis, samples were resuspended in pre-cooled 1× Tris-buffered saline and were transferred to 1.5 mL conical tubes containing 0.5 mL of nyosil M25. Samples/Oil aliquots were then spun for 1 min at 13,000 RPM. Following centrifugation, all media was aspirated from the tubes without disturbing the oil layer. Water was added on top of the oil layer and the spinning/aspiration process was repeated followed by an additional water wash. After the second wash step, all oil and water was removed and the cell pellet was snap frozen on dry ice and stored at −80° C. until further processing. Samples not undergoing immediate analysis were washed 2× with serum-free culture medium, resuspended in 1 mL of culture medium and incubated at 37c/5% $CO_2$ until they were processed by the aforementioned protocol. Each PBMC sample was treated with 500 µL of dry ice-cold extraction buffer (70% methanol, containing 0.5 µM chloro-adenosine triphosphate as internal standard). The above solution was vortexed for 5 minutes, then centrifuged at 20,000×g for 20 minutes. Supernatant was transferred to clean 1.5 mL eppendorf vials and loaded onto a centrifuging evaporator. Once dry, samples were reconstituted with 80 µL of mobile phase A, centrifuged at 20,000×g for 20 minutes and supernatants transferred to HPLC injection vials for analysis. An aliquot of 10 µL was injected into a Sciex 6500 LC/MS/MS system. Standard calibration curves for PBMC were constructed based on pmol of compound per sample. The value from each sample was then divided by the total number of cells in the sample to yield pmol per million cells. Micromolar concentrations were then derived using an intracellular volume of 0.2 µL per cell. The results of these experiments are shown in FIG. 2.

Figure 2:
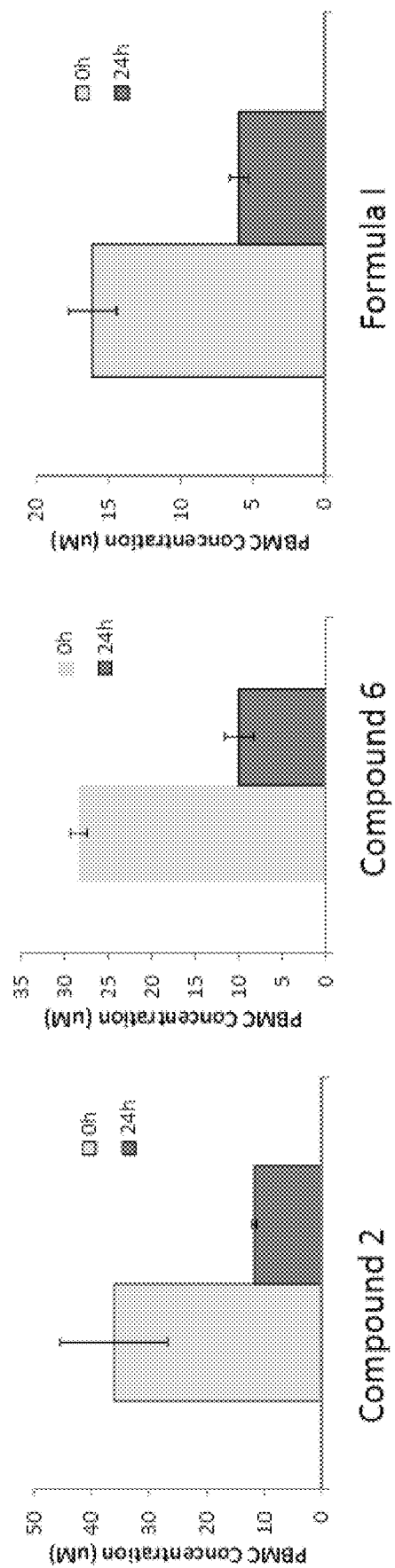
FIG. 2. Shows measurement of in-vitro intracellular triphosphate formation in PBMC with the compound of Formula I and compounds 2 and 6.

As seen in FIGS. 1 and 2, the compound of Formula I exhibits equal to or better in-vitro intracellular NTP (nucleotide triphosphate) formation in NHBEs but lower in PBMCs as compared to compound 2 and/or 6. This suggests that the compound of Formula I undergoes more selective metabolism in NHBEs (target cell type) relative to PBMCs compared to compound 2 and/or 6.

Example 43. Animal Pharmacokinetics Assay

Animal PK studies for the compound of Formula I and 6 were conducted using the following protocol. Animals weighing 3 to 6 kg were used for the in-life portion of the studies. Test articles were dosed intravenously by a constant rate infusion over 30 minutes as an aqueous solution of 12% captisol in water pH 3 at 10 mg/kg of body weight to male Cynomolgus monkeys. Plasma samples were collected at 0.25, 0.5, 1, 1.5 2, 4, 8, and 24 hr post-administration and PBMC samples were collected at 2 and 24 hr post-administration.

Blood samples (approximately 1 mL) were collected into pre-chilled collection tubes containing $K_2EDTA$ and were centrifuged at 4° C. to separate plasma. For PBMC collection, approximately 8 mL of blood samples were collected at room temperature into CPT vacutainer tubes containing sodium heparin for isolation. At each terminal collection, animals were anesthetized and lungs were harvested while animals are alive. Collected lungs were flash-frozen in liquid nitrogen immediately following removal.

The plasma samples from pharmacokinetic studies were subject to protein precipitation by addition of acetonitrile to final concentrations of 75% containing 5-iodotubericidin as internal standards. Analytes in plasma samples were separated on a 4 m 150×2 mm Synergi Max-RP column (Phenomenex, Torrance, CA) using mobile phase containing 0.2% formic acid and a linear gradient from 2% to 100% acetonitrile at a flow rate of 250 µL/min over 7 min. Eight points standard curves prepared in blank plasma covered concentrations from 5.1 to 5000 nM and showed linearity in excess of an R2 value of 0.99. Separately prepared quality control samples of 120 and 3,000 nM in plasma were analyzed at the beginning and end of each sample set to ensure accuracy and precision within 20%.

Each PBMC sample was treated with 500 µL of extraction buffer containing 67 mM ethylenediamine tetraacetic acid (EDTA) in 70% methanol, with 0.5 µM chloro-adenosine triphosphate as internal standard. The extraction buffer was cooled on dry ice. The above solution was vortexed for 5 minutes, then centrifuged at 20,000×g for 20 minutes. Supernatant was transferred to clean 1.5 mL eppendorf vials and loaded onto a centrifuging evaporator. Once dry, samples were reconstituted with 80 µL of 1 mM ammonium phosphate buffer (pH =7), centrifuged at 20,000×g for 20 minutes and supernatants transferred to HPLC injection vials for analysis. An aliquot of 10 µL was injected into an API 5000 LC/MS/MS system. In order to calculate intracellular concentration of metabolites, the total number of cells in each sample was determined using total DNA counting methods (Benech, et al. Peripheral Blood Mononuclear Cell Counting Using a DNA-detection-based Method. 2004 July 1; 330 (1): 172-4). Standard calibration curves for PBMC were constructed based on pmol of compound per sample. The value from each sample was then divided by the total number of cells in the sample to yield pmol per million cells. Micromolar concentrations were then derived using an intracellular volume of 0.2 µL per cell.

Lung samples were prepared by sectioning into smaller pieces and distributing into pre-weighed 15 mL conical tubes, which were kept on dry ice. The ice-cold extraction buffer (0.1% KOH and 67 mM ethylenediamine tetraacetic acid in 70% methanol containing 0.5 µM chloro-adenosine triphosphate as the internal standard, ~2 mL) was added into ~0.5 g of each lung sample. The mixtures were promptly homogenized using an Omni-Tip TH™ with disposable, hard tissue homogenizer probes (Omni International). Aliquots of the homogenate were filtered by using 0.2 µm 96-well polypropylene filter plate (Varian Captiva™). The filtrates were evaporated to dryness and reconstituted with an equal volume of 1 mM ammonium phosphate buffer (pH=7) prior to LC-MS/MS analysis.

The nucleoside triphosphate quantification used ion pairing nucleotide detection LC-MS/MS method. Analytes were separated by a 2.5 m 2.0×50 mm Luna C18 column (Phenomenex, Torrance, CA) using an ion pairing buffer containing 3 mM ammonium phosphate (pH 5) with 10 mM dimethylhexylamine (DMH) and a multistage linear gradient from 10% to 50% acetonitrile at a flow rate of 160 µL/min over 11 min. Seven points standard curves prepared in blank matrices covered concentrations from 24.0 to 17,500 nM and showed linearity in excess of an $R^2$ value of 0.99.

Figure 3:
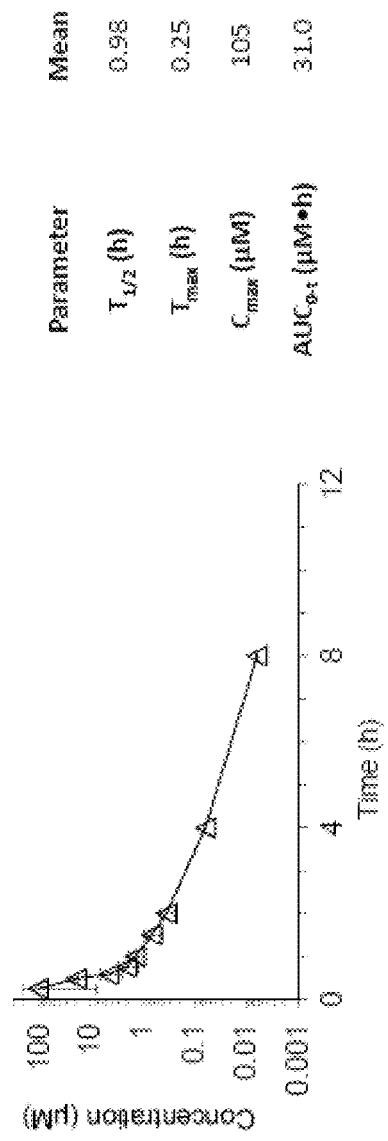
FIG. 3. Shows cynomologous monkey pharmacokinetic data for the compound of Formula I and compound 6.
Figure 3:
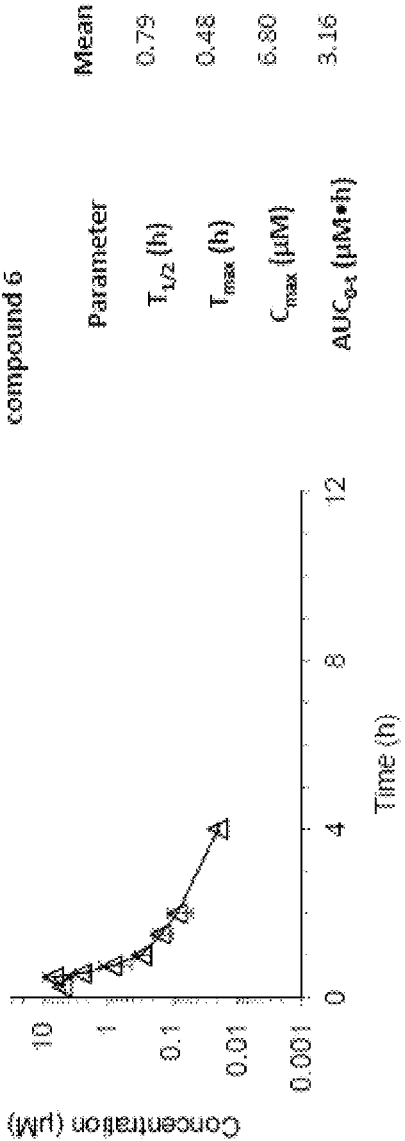

The results of these experiments are shown in FIG. 3 and in the Table below.

TABLE 13

Mean lung and PBMC triphosphate concentrations following a 30 minute intravenous infusion of the compound of Formula I and compound 6 at 10 mg/kg to male cynomolgus monkeys (mean, n = 2).

| Compound infused | Tissue | 2 h | 24 h |
|---|---|---|---|
| Formula I | Lung (nmol/g tissue) | 2.88 | 2.01 |
| Formula I | PBMC (µM) | 61.3 | 27.1 |
| 6 | Lung (nmol/g tissue) | 2.25 | 1.29 |
| 6 | PBMC (µM) | 169 | 22.4 |

As seen, the compound of Formula I exhibits higher lung NTP concentration and lower PBMC NTP concentration in cyno PK studies. This indicates that, compared to the compound 6, the compound of Formula I undergoes more selective metabolism in lung tissue relative to the PBMCs.

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of Formula I:

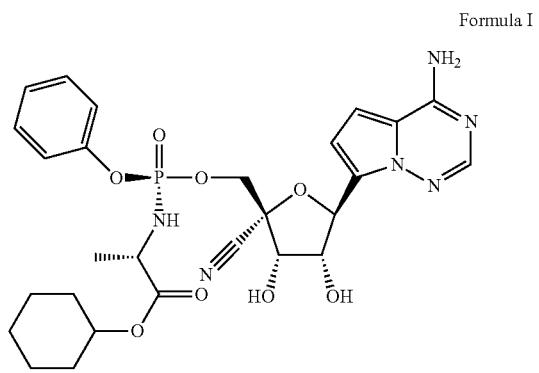 [SMILES: C[C@H](N[P@](=O)(OC[C@@]1(C#N)O[C@@H](c2ccc3c(N)ncnn23)[C@H](O)[C@@H]1O)Oc1ccccc1)C(=O)OC1CCCCC1]

Formula I or a pharmaceutically acceptable salt thereof.

2. A pharmaceutical formulation comprising a therapeutically effective amount of the compound of claim 1, or a pharmaceutically acceptable salt thereof, and a pharmaceutically acceptable carrier or excipient.

3. A method of treating a Pneumoviridae virus infection in a human in need thereof, the method comprising administering to the human a therapeutically effective amount of the compound of claim 1, or a pharmaceutically acceptable salt thereof, wherein the Pneumoviridae virus infection is a respiratory syncytial virus infection.

4. A method of treating a Picornaviridae virus infection in a human in need thereof, the method comprising administering to the human a therapeutically effective amount of the compound of claim 1, or a pharmaceutically acceptable salt thereof, wherein the Picornaviridae virus infection is human rhinovirus infection.

5. A method for the treatment or prophylaxis of an exacerbation of a respiratory condition by a viral infection in a human in need thereof, the method comprising administering to the human a therapeutically effective amount of the compound of claim 1, or a pharmaceutically acceptable salt thereof, wherein the respiratory condition is chronic obstructive pulmonary disease, and wherein the infection is caused by a respiratory syncytial virus or rhinovirus.

6. A method for the treatment or prophylaxis of an exacerbation of a respiratory condition by a viral infection in a human in need thereof, the method comprising administering to the human a therapeutically effective amount of the compound of claim 1, or a pharmaceutically acceptable salt thereof, wherein the respiratory condition is asthma, and wherein the infection is caused by respiratory syncytial virus or rhinovirus.

7. A compound having the structure:

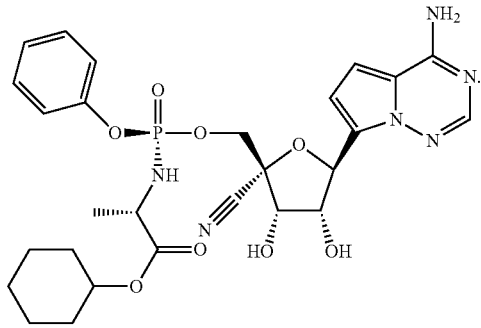 [SMILES: C[C@H](N[P@](=O)(OC[C@@]1(C#N)O[C@@H](c2ccc3c(N)ncnn23)[C@H](O)[C@@H]1O)Oc1ccccc1)C(=O)OC1CCCCC1]

8. A pharmaceutical composition comprising a compound having the structure:
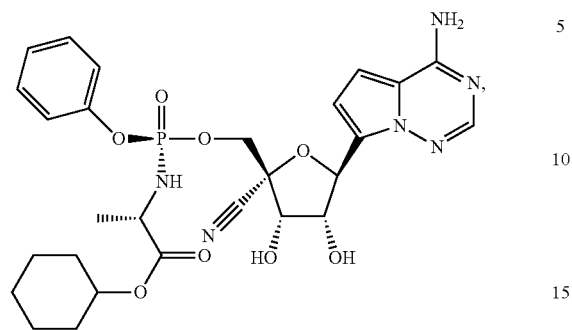
and a pharmaceutically acceptable excipient.
* * * * *

SEQUENCE LISTING

<160> NUMBER OF SEQ ID NOS: 4

<210> SEQ ID NO 1
<211> LENGTH: 244
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 1
ucagucaguc agucagucag ucagucaguc agucagucag ucagucaguc agucagucag      60
ucagucaguc agucagucag uccaagucca aguccaaguc caaguccaag uccaagucca     120
aguccaaguc caaguccaag uccaagucca aguccaaguc caagucaguc agucagucag     180
ucagucaguc agucagucag ucagucaguc agucagucag ucagucaguc agucagucag     240
ucag                                                                  244

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 2
catccagcaa atacaccatc ca                                              22

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttctgcacat cataattagg agtatcaa                                        28

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
cggagcacag gagat                                                      15
```